(12) United States Patent
Klinguer-Hamour

(10) Patent No.: US 9,090,686 B2
(45) Date of Patent: Jul. 28, 2015

(54) ANTIBODIES FOR THE TREATMENT OF HIV

(75) Inventor: Christine Klinguer-Hamour, Groisy (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 791 days.

(21) Appl. No.: 12/913,300

(22) Filed: Oct. 27, 2010

(65) Prior Publication Data

US 2011/0088104 A1 Apr. 14, 2011

Related U.S. Application Data

(63) Continuation-in-part of application No. PCT/EP2010/055863, filed on Apr. 29, 2010.

(60) Provisional application No. 61/173,680, filed on Apr. 29, 2009.

(30) Foreign Application Priority Data

Apr. 29, 2009 (EP) ..................................... 09159076

(51) Int. Cl.
| | | |
|---|---|---|
| *A61K 39/395* | (2006.01) | |
| *C07K 16/28* | (2006.01) | |
| *C07K 16/24* | (2006.01) | |
| *A61K 31/439* | (2006.01) | |
| *A61K 45/00* | (2006.01) | |
| *A61K 39/00* | (2006.01) | |

(52) U.S. Cl.
CPC .............. *C07K 16/24* (2013.01); *A61K 31/439* (2013.01); *A61K 39/3955* (2013.01); *A61K 45/00* (2013.01); *C07K 16/2866* (2013.01); *A61K 2039/505* (2013.01); *C07K 2316/96* (2013.01); *C07K 2317/24* (2013.01); *C07K 2317/56* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,585,089 | A | 12/1996 | Queen et al. |
| 5,639,641 | A | 6/1997 | Pedersen et al. |
| 5,693,761 | A | 12/1997 | Queen et al. |
| 5,844,094 | A * | 12/1998 | Hudson et al. ............. 530/387.3 |
| 5,877,293 | A | 3/1999 | Adair et al. |
| 5,886,152 | A | 3/1999 | Nakatani et al. |
| 6,054,297 | A | 4/2000 | Carter et al. |
| 6,180,370 | B1 | 1/2001 | Queen et al. |

FOREIGN PATENT DOCUMENTS

| | | |
|---|---|---|
| EP | 0 451 216 B1 | 10/1991 |
| EP | 0 566 647 B1 | 10/1993 |
| EP | 0 682 040 B1 | 11/1995 |
| EP | 0 939 127 A3 | 9/1999 |

OTHER PUBLICATIONS

Bendig, Methods: A Companion to Methods in Enzymology, vol. 8, p. 83-93, 1995.*
Colman, Research in Immunology, vol. 145, p. 33-36, 1994.*
Paul, Fundamental Immunology, Third Edition, p. 292-295, 1993.*
Rudikoff, Proceedings of the National Academy of Sciences, U.S.A., vol. 79, p. 1979-1983, 1982.*
Johnson, Antibody Engineering: Methods and Protocols, p. 11-25, 2004.*
Carter, Nature Reviews: Immunology, vol. 6, p. 343-357, 2006.*
Klein, Proceedings of the National Academy of Sciences, vol. 106, No. 18, p. 7385-7390, 2009.*
Stewart, J.M. "Solid Phase Synthesis," pp. 71-95. (1984) ISBN 0-935940.
Andradas, C. et al., "The Orphan G Protein-Coupled Receptor GPR55 Promotes Cancer Cell Proliferation Via ERK," *Oncogene*, 30:245-52 (2011).
Angel, S. et al., "A Single Amino Acid Substitution Abolishes the Heterogeneity of Chimeric Mouse/Human (IgG4) Antibody," *Mol. Immunol.*, 30:105-08 (1993).
Angers, S. et al., "Detection of $\beta_2$-Adrenergic Receptor Dimerization in Living Cells Using Bioluminescence Resonance Energy Transfer (BRET)," *PNAS*, 97:3684-89 (2000).
Bebbington, C.R. et al., "High-Level Expression of a Recombinant Antibody From Myeloma Cells Using a Glutamine Synthetase Gene As an Amplifiable Selectable Marker," *Biotech.*, 10:169-75 (1992).
Bès, C. et al., "PIN-bodies: A New Class of Antibody-Like Proteins With CD4 Specificity Derived From the Protein Inhibitor of Neuronal Nitric Oxide Synthase," *Biochem. and Biophys. Res. Comm.*, 343:334-44 (2006).
Bès, C. et aL, "Efficient CD4 Binding and Immunosuppressive Properties of the 13B8.2 Monoclonal Antibody Are Displayed by Its CDR-H1-derived Peptide CB1," *FEBS Letters*, 508:67-74 (2001).
Bhatia, B. et al., "Mitogenic Sonic Hedgehog Signaling Drives E2F1-Dependent Lipogenesis in Progenitor Cells and Medulloblastoma," *Oncogene*, 30:410-22 (2011).
Bian, X-W., et al., "Preferential Expression of Chemokine Receptor CXCR4 by Highly Malignant Human Gliomas and Its Association with Poor Patient Survival," *Neurosurgery*, 61:570-79 (2007).
Glennie, M. et al., "Preparation and Performance of Bispecific F(ab'γ) Antibody Containing Thioether-Linked Fab'γ Fragments," *J. Immunol.*, 139:2367-75 (1987).

(Continued)

*Primary Examiner* — Mark Halvorson
*Assistant Examiner* — Michael D Allen
(74) *Attorney, Agent, or Firm* — Finnegan, Henderson, Farabow, Garrett & Dunner, L.L.P.

(57) ABSTRACT

The present invention relates to novel isolated antibodies, or the derivatives or antigen binding fragments of same, capable of binding to CXCR4 but also of inducing conformational changes of the CXCR4 homodimers and able to inhibit HIV-1 primary isolate replication in PBMC. More particularly, the present invention relates to the 515H7 and 301aE5 monoclonal antibodies, specific to the CXCR4 protein, as well as their use for the treatment of HIV infection. Pharmaceutical compositions comprising such antibodies and a process for the selection of such antibodies are also covered.

45 Claims, 18 Drawing Sheets

(56) References Cited

OTHER PUBLICATIONS

Holl, V. et al, "Involvement of FcγR I (CD64) in the Mechanism of HIV-1 Inhibition by Polyclonal IgG Purified from Infected Patients in Cultured Monocyte-Derived Macrophages," *J. Immunol.*, 173:6274-83 (2004).

Holliger, P. et al., "Engineering Antibodies for the Clinic," *Cancer and Metastasis Rev.*, 18:411-19 (1999).

Jones, P.T. et al., "Replacing the Complementarity-Determining Regions in a Human Antibody With Those From a Mouse," *Nature*, 321:522-25 (1986).

Juarez, J. et al., "Chemokines and their Receptors as Therapeutic Targets: The Role of the SDF-1/CXCR4 Axis," *Curr. Pharm. Des.*, 10:1245-59 (2004).

Juarez, J. et al., "Effects of Inhibitors of the Chemokine Receptor CXCR4 on Acute Lymphoblastic Leukemia Cells in Vitro," *Leukemia*, 17:1294-300 (2003).

Kaas, Q. et al., "IMGT Colliers de Perles: Standardized Sequence-Structure Representations of the IgSF and MhcSF Superfamily Domains," *Curr. Bioinfor.*, 2:21-30 (2007).

Kaas, Q. et al., "IMGT/3Dstructure-DB and IMGT/StructuralQuery, a Database and a Tool for Immunoglobulin, T Cell Receptor and MHC Structural Data," *Nucleic Acids Res. Database Issue*, 32:D208-10 (2004).

Kabat, E. et al., "Identical V Region amino Acid Sequences and Segments of Sequences in Antibodies of Different Specificities: Relative Contributions of $V_H$ and $V_L$ Genes, Minigenes, and Complementarity-Determining Regions to Binding of Antibody-Combining Sites," *J. Immunol.*, 147:1709-19 (1991).

Kohl, A. et al., "Designed to be Stable: Crystal Structure of a Consensus Ankyrin Repeat Protein," *PNAS*, 100:1700-05 (2003).

Köhler, G. et aL, "Continuous Cultures of Fused Cells Secreting Antibody of Predefined Specificity," *Nature*, 256:495-97 (1975).

Lefranc, M-P. et al., "IMGT Unique Numbering for Immunoglobulin and T Cell Receptor Variable Domains and Ig Superfamily V-like Domains," *Devl. & Compar. Immunol.*, vol. 27, 55-77 (2003).

Lefranc, M-P. et al., "Unique Database Numbering System for Immunogenetic Analysis," *Immunol. Today*, vol. 18, 509 (1997).

Lefranc, M-P. "The IMGT Unique Numbering for Immunoglobulins, T-Cell Receptors, and Ig-Like Domains," *The Immunologist*, 7:132-36 (1999).

Merchant, A.M. et al., "An Efficient Route to Human Bispecific IgG," *Nature Biotech.*, 16:677-81 (1998).

Mondor, I. et al., "Interactions Among HIV gp120, CD4, and CXCR4: Dependence on CD4 Expression Level, gp120 Viral Origin, Conservation of the gp120 COOH- and $NH_2$-Termini and V1/V2 and V3 Loops, and Sensitivity to Neutralizing Antibodies," *Virol.*, 248:394-405 (1998).

Mountain, A. et al., "Engineering Antibodies for Therapy," *Biotech. and Gen. Eng. Rev.*, 10:1-142 (1992).

Needleman, S.B. et al., "A General Method Applicable to the Search for Similarities in the Amino Acid Sequence of Two Proteins," *J. Mol. Biol.*, 48:443-53 (1970).

Nicaise, M. et al., "Affinity Transfer by CDR Grafting on a Nonimmunoglobulin Scaffold," *Protein Sci.*, 13:1882-91 (2004).

Park, H.D. et al., "Pancreatic Adenocarcinoma Upregulated Factor Promotes Metastasis by Regulating TLR/CXCR4 Activation," *Oncogene*, 30:201-11 (2011).

Park, S.S. et al., "Generation and Characterization of a Novel Tetravalent Bispecific Antibody that Binds to Hepatitis B Virus Surface Antigens," *Mol Immunol.*, 37:1123-30 (2000).

Pearson, W.R. et al., "Improved Tools for Biological Sequence Comparison," *PNAS*, 85:2444-48 (1988).

Repp, R. et al. "G-CSF-Stimulated PMN in Immunotherapy of Breast Cancer with a Bispecific Antibody to FcγRI and to HER-2/neu (MDX-210)," *J. of Hematother* 4:415-21 (1995).

Rey-Cuille, M-A. et al., "Conserved CXCR4 Usage and Enhanced Replicative Capacity of HIV-2/287, an Isolate Highly Pathogenic in *Macaca nemestrina*," *AIDS*, 15:2349-57 (2001).

Riechmann, L. et al., "Reshaping Human Antibodies for Therapy," *Nature*, 332:323-27 (1988).

Ruiz, M. et al., "IMGT Gene Identification and Colliers de Perles of Human Immunoglobulins with Known 3D Structures," *Immunogenet.*, 53:857-83 (2002).

Singer, I.I. et al., "Optimal Humanization of 1B4, an Anti-CD18 Murine Monoclonal Antibody, Is Achieved by Correct Choice of Human V-Region Framework Sequences," *J. Immunol.*, 150:2844-57 (1993).

Skerra, A. "Engineered Protein Scaffolds for Molecular Recognition," *J. Mol. Recognit.*, 13:167-87 (2000).

Skerra, A. "Anticalins: A New Class of Engineered Ligand-Binding Proteins with Antibody-Like Properties," *Rev. Mole. Biotech.*, 74:257-75 (2001).

Smith, T. et al., "Comparison of Biosequences," *Advan. Appl. Math.*, 2:482-89 (1981).

Staerz, U.D. et al., "Hybrid Hybridoma Producing a Bispecific Monoclonal Antibody that can Focus Effector T-cell Activity," *PNAS*, 83:1453-57 (1986).

Strizki, J.M. et al., "A Monoclonal Antibody (12G5) Directed Against CXCR-4 Inhibits Infection with the Dual-Tropic Human Immunodeficiency Virus Type 1 Isolate HIV-$1_{89.6}$ but Not the T-Tropic Isolate HIV-$1_{HxB1}$," *J. Virol.*, 71:5678-83 (1997).

Suresh, M.R. et al., "Bispecific Monoclonal Antibodies from Hybrid Hybridomas," *Meth. in Enzymol.*, 121:210-28 (1986).

Tanaka, R. et al., "Unique Monoclonal Antibody Recognizing the Third Extracellular Loop of CXCR4 Induces Lymphocyte Agglutination and Enhances Human Immunodeficiency Virus Type 1-Mediated Syncytium Formation and Productive Infection," *J. Virol.*, 75:11534-43 (2001).

Tatusova, T.A. et al., "BLAST 2 Sequences, A New Tool for Comparing Protein and Nucleotide Sequences," *FEMS Microbiol. Ltrs.*, 174:247-50 (1999).

Verhoeyen, M. et al., "Engineering of Antibodies," *BioEssays*, 8:74-78 (1988).

Verhoeyen, M. et al., "Reshaping Human Antibodies: Grafting an Antilysozyme Activity," *Science*, 239:1534-36 (1988).

Zhao, Q et al., "Development of a Cell-Based Enzyme-Linked Immunosorbent Assay for High-Throughput Screening of HIV Type 1 Entry Inhibitors Targeting the Coreceptor CXCR4," *AIDS Res. And Hum. Retrovir.*, 19:947-55 (2003).

Zlotnik, A. et al., "Chemokines: A New Classification System and Their Role in Immunity," *Immunity*, 12:121-27 (2000).

International Search Report for International Application No. PCT/EP2010/055863, dated Aug. 5, 2010.

\* cited by examiner

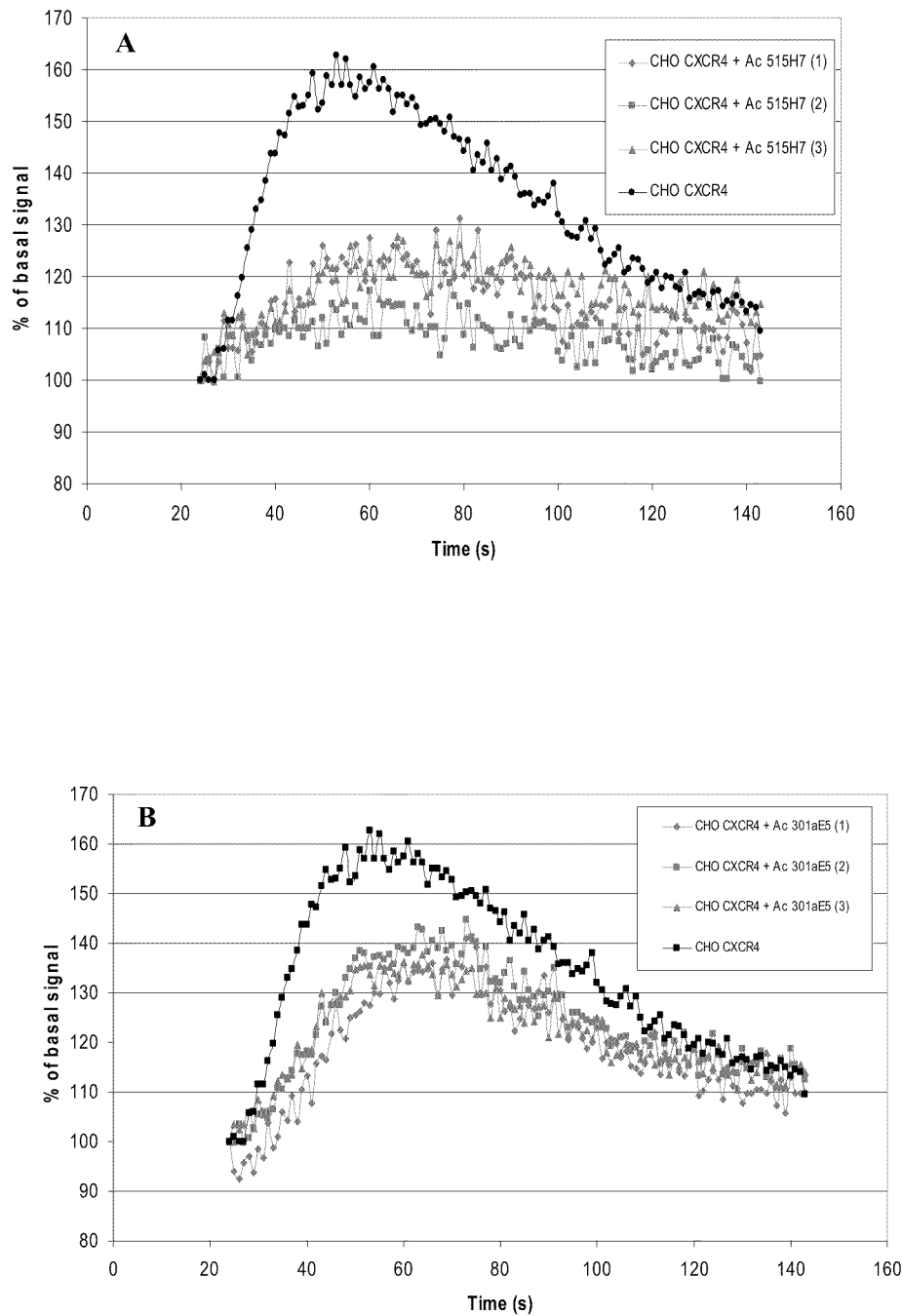
FIGURE 6A et 6B

```
                    FR1-IMGT              CDR1-IMGT         FR2-IMGT            CDR2-IMGT
                    (1-26)                (27-38)           (39-55)             (56-65)

1         10        20        30              40        50          60
                  .........|.........|......   ...|........   .|.........|.....   ....|.....
515H7 VH          EVNLVESGG.GLVQPGGSLRLSCATS   GFTF....TDNY   MSWVRQPPGKALEWLGF   IRNKANGYTT
IGHV3-49*04       EVQLVESGG.GLVQPGRSLRLSCTAS   GFTF....GDYA   MSWVRQAPGKGLEWVGF   IRSKAYGGTT

VH1               EVQLVESGG.GLVQPGRSLRLSCTAS   GFTF....TDNY   MSWVRQAPGKGLEWVGF   IRNKANGYTT
VH1 D76N          EVQLVESGG.GLVQPGRSLRLSCTAS   GFTF....TDNY   MSWVRQAPGKGLEWVGF   IRNKANGYTT

FR3-IMGT                    CDR3-IMGT     FR4-IMGT
                                  (66-104)                    (105-115)     (116-125)

70        80        90        100
                     ....|.........|.........|.........|....
515H7 VH             DYSASVR.GRFTISRDNSQSILYLQMNALRAEDSATYYC   ARDVGSNYFDYW   GQGTTLTVSS
IGHV3-49*04          EYAASVK.GRFTISRDDSKSIAYLQMNSLKTEDTAVYYC   TR
IGHJ4*01                                                                    YFDYW   GQGTLVTVSS

VH1                  EYAASVK.GRFTISRDDSKSIAYLQMNSLKTEDTAVYYC   ARDVGSNYFDYW   GQGTLVTVSS
VH1 D76N             EYAASVK.GRFTISRDNSKSIAYLQMNSLKTEDTAVYYC   ARDVGSNYFDYW   GQGTLVTVSS
```

Figure 17

```
                    FR1-IMGT              CDR1-IMGT         FR2-IMGT            CDR2-IMGT
                    (1-26)                (27-38)           (39-55)             (56-65)

1         10        20        30              40        50          60
                  .........|.........|......   ...|.......    .|.........|.....   ....|.....
515H7 VL          DIVMSQSPSSLAVSAGEKVTMSCKSS   QSLFNSRTRKNY   LAWYQQKPGQSPKLLIY   WA.......S
IGKV4-1*01        DIVMTQSPDSLAVSLGERATINCKSS   QSVLYSSNNKNY   LAWYQQKPGQPPKLLIY   WA.......S
VL Var2           DIVMTQSPSSLAVSLGERATMSCKSS   QSLFNSRTRKNY   LAWYQQKPGQSPKLLIY   WA.......S
VL Var2.1         DIVMTQSPDSLAVSLGERATMSCKSS   QSLFNSRTRKNY   LAWYQQKPGQPPKLLIY   WA       S
VL Var2.2         DIVMTQSPDSLAVSLGERATMSCKSS   QSLFNSRTRKNY   LAWYQQKPGQPPKLLIY   WA       S
VL Var2.3         DIVMTQSPDSLAVSLGERATMSCKSS   QSLFNSRTRKNY   LAWYQQKPGQPPKLLIY   WA       S

FR3-IMGT                    CDR3-IMGT     FR4-IMGT
                                  (66-104)                    (106-113)     (114-123)

70        80        90        100
                     ....|.........|.........|.........|....
515H7 VL             ARDSGVP.ARFTGSG..SETYFTLTISRVQAEDLAVYYC   MQSFNLRT   FGQGTKVEIK
IGKV4-1*01           TRESGVP.DRFSGSG..SGTDFTLTISSLQAEDVAVYYC
IGKJ1*01                                                     WT         FGQGTKVEIK
VL Var2              ARDSGVP.ARFTGSG..SETYFTLTISRVQAEDLAVYYC   MQSFNLRT   FGQGTKVEIK
VL Var2.1            ARDSGVP DRFSGSG   SETYFTLTISRVQAEDLAVYYC   MQSFNLRT   FGQGTKVEIK
VL Var2.2            ARDSGVP DRFTGSG   SETYFTLTISRVQAEDVAVYYC   MQSFNLRT   FGQGTKVEIK
VL Var2.3            ARDSGVP DRFTGSG   SETYFTLTISSLQAEDLAVYYC   MQSFNLRT   FGQGTKVEIK
```

Figure 18

SEQUENCE LISTING

```
<160> NUMBER OF SEQ ID NOS: 98

<210> SEQ ID NO 1
<211> LENGTH: 12
<212> TYPE: PRT
<213> ORGANISM: Mus musculus

<400> SEQUENCE: 1
```

```
Gln Ser Leu Phe Asn Ser Arg Thr Arg Lys Asn Tyr
1               5                   10
```

<210> SEQ ID NO 2
<211> LENGTH: 3
<212> TYPE: PRT
<213> ORGANISM: Mus musculus

<400> SEQUENCE: 2

```
Trp Ala Ser
1
```

<210> SEQ ID NO 3
<211> LENGTH: 8
<212> TYPE: PRT
<213> ORGANISM: Mus musculus

<400> SEQUENCE: 3

```
Met Gln Ser Phe Asn Leu Arg Thr
1               5
```

<210> SEQ ID NO 4
<211> LENGTH: 8
<212> TYPE: PRT
<213> ORGANISM: Mus musculus

<400> SEQUENCE: 4

```
Gly Phe Thr Phe Thr Asp Asn Tyr
1               5
```

<210> SEQ ID NO 5
<211> LENGTH: 10
<212> TYPE: PRT
<213> ORGANISM: Mus musculus

<400> SEQUENCE: 5

```
Ile Arg Asn Lys Ala Asn Gly Tyr Thr Thr
1               5                   10
```

<210> SEQ ID NO 6
<211> LENGTH: 11
<212> TYPE: PRT
<213> ORGANISM: Mus musculus

<400> SEQUENCE: 6

```
Ala Arg Asp Val Gly Ser Asn Tyr Phe Asp Tyr
1               5                   10
```

<210> SEQ ID NO 7
<211> LENGTH: 112
<212> TYPE: PRT
<213> ORGANISM: Mus musculus

<400> SEQUENCE: 7

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Asp Ser Gly Val
    50                  55                  60
```

```
Pro Ala Arg Phe Thr Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gly Gly Thr Lys Leu Glu Ile Lys
            100                 105                 110

<210> SEQ ID NO 8
<211> LENGTH: 120
<212> TYPE: PRT
<213> ORGANISM: Mus musculus

<400> SEQUENCE: 8

Glu Val Asn Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Asn
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Arg Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Val Gly Ser Asn Tyr Phe Asp Tyr Trp Gly Gln
            100                 105                 110

Gly Thr Thr Leu Thr Val Ser Ser
        115                 120

<210> SEQ ID NO 9
<211> LENGTH: 17
<212> TYPE: PRT
<213> ORGANISM: Mus musculus

<400> SEQUENCE: 9

Lys Ser Ser Gln Ser Leu Phe Asn Ser Arg Thr Arg Lys Asn Tyr Leu
1               5                   10                  15

Ala

<210> SEQ ID NO 10
<211> LENGTH: 7
<212> TYPE: PRT
<213> ORGANISM: Mus musculus

<400> SEQUENCE: 10

Trp Ala Ser Ala Arg Asp Ser
1               5

<210> SEQ ID NO 11
<211> LENGTH: 5
<212> TYPE: PRT
<213> ORGANISM: Mus musculus

<400> SEQUENCE: 11

Asp Asn Tyr Met Ser
1               5

<210> SEQ ID NO 12
<211> LENGTH: 19
```

```
<212> TYPE: PRT
<213> ORGANISM: Mus musculus

<400> SEQUENCE: 12

Phe Ile Arg Asn Lys Ala Asn Gly Tyr Thr Thr Asp Tyr Ser Ala Ser
1               5                   10                  15

Val Arg Gly

<210> SEQ ID NO 13
<211> LENGTH: 9
<212> TYPE: PRT
<213> ORGANISM: Mus musculus

<400> SEQUENCE: 13

Asp Val Gly Ser Asn Tyr Phe Asp Tyr
1               5

<210> SEQ ID NO 14
<211> LENGTH: 36
<212> TYPE: DNA
<213> ORGANISM: Mus musculus

<400> SEQUENCE: 14
cagagtctgt tcaacagtcg aacccgaaag aactac                          36

<210> SEQ ID NO 15
<211> LENGTH: 9
<212> TYPE: DNA
<213> ORGANISM: Mus musculus

<400> SEQUENCE: 15 tgggcatcc                                                         9

<210> SEQ ID NO 16
<211> LENGTH: 24
<212> TYPE: DNA
<213> ORGANISM: Mus musculus

<400> SEQUENCE: 16
atgcaatctt ttaatcttcg gacg                                       24

<210> SEQ ID NO 17
<211> LENGTH: 24
<212> TYPE: DNA
<213> ORGANISM: Mus musculus

<400> SEQUENCE: 17
gggttcacct tcactgataa ctac                                       24

<210> SEQ ID NO 18
<211> LENGTH: 30
<212> TYPE: DNA
<213> ORGANISM: Mus musculus

<400> SEQUENCE: 18
attagaaaca aagctaatgg ttacacaaca                                 30

<210> SEQ ID NO 19
<211> LENGTH: 33
<212> TYPE: DNA
<213> ORGANISM: Mus musculus

<400> SEQUENCE: 19
```

```
gcaagagatg tcggttccaa ctactttgac tac                                   33

<210> SEQ ID NO 20
<211> LENGTH: 336
<212> TYPE: DNA
<213> ORGANISM: Mus musculus

<400> SEQUENCE: 20
gacattgtga tgtcacagtc tccatcctcc ctggctgtgt cagcaggaga gaaggtcact      60
atgagctgca aatccagtca gagtctgttc aacagtcgaa cccgaaagaa ctacttggct     120
tggtaccagc agaagccagg gcagtctcct aaactgctga tctactgggc atccgctagg     180
gattctgggg tccctgctcg cttcacaggc agtggatctg agacatattt cactctcacc     240
atcagccgtg tgcaggctga agacctggca gtttattact gcatgcaatc ttttaatctt     300
cggacgttcg gtggaggcac caagctggaa atcaaa                               336

<210> SEQ ID NO 21
<211> LENGTH: 360
<212> TYPE: DNA
<213> ORGANISM: Mus musculus

<400> SEQUENCE: 21
gaggtgaacc tggtggagtc tggaggaggc ttggtacagc ctgggggttc tctgagactc      60
tcctgtgcaa cttctgggtt caccttcact gataactaca tgagttgggt ccgccagcct     120
ccaggaaagg cacttgagtg gttgggcttt attagaaaca agctaatgg ttacacaaca     180 gactacagtg catctgtgag gggtcggttc accatctcaa gagataattc ccaaagcatc     240
ctctatcttc aaatgaacgc cctgagagcc gaagacagtg ccacttatta ctgtgcaaga     300
gatgtcggtt ccaactactt tgactactgg ggccaaggca ccactctcac agtctcctca     360

<210> SEQ ID NO 22
<211> LENGTH: 51
<212> TYPE: DNA
<213> ORGANISM: Mus musculus

<400> SEQUENCE: 22
aaatccagtc agagtctgtt caacagtcga acccgaaaga actacttggc t              51

<210> SEQ ID NO 23
<211> LENGTH: 21
<212> TYPE: DNA
<213> ORGANISM: Mus musculus

<400> SEQUENCE: 23
tgggcatccg ctagggattc t                                               21

<210> SEQ ID NO 24
<211> LENGTH: 15
<212> TYPE: DNA
<213> ORGANISM: Mus musculus

<400> SEQUENCE: 24
gataactaca tgagt                                                      15

<210> SEQ ID NO 25
<211> LENGTH: 57
<212> TYPE: DNA
<213> ORGANISM: Mus musculus

<400> SEQUENCE: 25
```

```
tttattagaa acaaagctaa tggttacaca acagactaca gtgcatctgt gagggt        57
```

<210> SEQ ID NO 26
<211> LENGTH: 27
<212> TYPE: DNA
<213> ORGANISM: Mus musculus

<400> SEQUENCE: 26

```
gatgtcggtt ccaactactt tgactac                                        27
```

<210> SEQ ID NO 27
<211> LENGTH: 352
<212> TYPE: PRT
<213> ORGANISM: Homo sapiens

<400> SEQUENCE: 27

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val

```
                305                 310                 315                 320
Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
                340                 345                 350
```

<210> SEQ ID NO 28
<211> LENGTH: 356
<212> TYPE: PRT
<213> ORGANISM: Homo sapiens

<400> SEQUENCE: 28

```
Met Ser Ile Pro Leu Pro Leu Gln Ile Tyr Thr Ser Asp Asn Tyr
1               5                   10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Ile
                35                  40                  45

Tyr Ser Ile Ile Phe Leu Thr Gly Ile Val Gly Asn Gly Leu Val Ile
        50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
                100                 105                 110

Cys Lys Ala Val His Val Ile Tyr Thr Val Asn Leu Tyr Ser Ser Val
                115                 120                 125

Leu Ile Leu Ala Phe Ile Ser Leu Asp Arg Tyr Leu Ala Ile Val His
        130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
                180                 185                 190

Phe Tyr Pro Asn Asp Leu Trp Val Val Val Phe Gln Phe Gln His Ile
                195                 200                 205

Met Val Gly Leu Ile Leu Pro Gly Ile Val Ile Leu Ser Cys Tyr Cys
        210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
                260                 265                 270

Ile Ile Lys Gln Gly Cys Glu Phe Glu Asn Thr Val His Lys Trp Ile
                275                 280                 285

Ser Ile Thr Glu Ala Leu Ala Phe Phe His Cys Cys Leu Asn Pro Ile
        290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335
```

Lys Arg Gly Gly His Ser Ser Val Ser Thr Glu Ser Glu Ser Ser
            340                 345                 350

Phe His Ser Ser
        355

<210> SEQ ID NO 29
<211> LENGTH: 360
<212> TYPE: PRT
<213> ORGANISM: Homo sapiens

<400> SEQUENCE: 29

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 30
<211> LENGTH: 8
<212> TYPE: PRT
<213> ORGANISM: Mus musculus

<400> SEQUENCE: 30

Lys Gln Ser Tyr Asn Leu Arg Thr
1               5

<210> SEQ ID NO 31
<211> LENGTH: 8
<212> TYPE: PRT
<213> ORGANISM: Mus musculus

<400> SEQUENCE: 31

Gly Phe Ser Leu Thr Asp Tyr Gly
1               5

<210> SEQ ID NO 32
<211> LENGTH: 7
<212> TYPE: PRT
<213> ORGANISM: Mus musculus

<400> SEQUENCE: 32

Ile Trp Gly Asp Gly Thr Thr
1               5

<210> SEQ ID NO 33
<211> LENGTH: 10
<212> TYPE: PRT
<213> ORGANISM: Mus musculus

<400> SEQUENCE: 33

Ala Arg Gly Arg Gln Phe Gly Phe Asp Tyr
1               5                   10

<210> SEQ ID NO 34
<211> LENGTH: 112
<212> TYPE: PRT
<213> ORGANISM: Mus musculus

<400> SEQUENCE: 34

Asp Ile Val Met Ser Gln Ser Pro Ser Ser Leu Ala Val Ser Ala Gly
1               5                   10                  15

Glu Lys Val Thr Met Arg Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Phe Trp Ala Ser Ile Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 35

```
<211> LENGTH: 116
<212> TYPE: PRT
<213> ORGANISM: Mus musculus

<400> SEQUENCE: 35

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Tyr Trp Val Arg Gln Pro Pro Gly Lys Gly Leu Glu Trp Leu
        35                  40                  45

Gly Met Ile Trp Gly Asp Gly Thr Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Thr Leu Gln Thr Asp Asp Thr Ala Arg Tyr Tyr Cys Ala
                85                  90                  95

Arg Gly Arg Gln Phe Gly Phe Asp Tyr Trp Gly Gln Gly Thr Thr Leu
            100                 105                 110

Thr Val Ser Ser
            115

<210> SEQ ID NO 36
<211> LENGTH: 7
<212> TYPE: PRT
<213> ORGANISM: Mus musculus

<400> SEQUENCE: 36

Trp Ala Ser Ile Arg Glu Ser
1               5

<210> SEQ ID NO 37
<211> LENGTH: 8
<212> TYPE: PRT
<213> ORGANISM: Mus musculus

<400> SEQUENCE: 37

Lys Gln Ser Tyr Asn Leu Arg Thr
1               5

<210> SEQ ID NO 38
<211> LENGTH: 5
<212> TYPE: PRT
<213> ORGANISM: Mus musculus

<400> SEQUENCE: 38

Asp Tyr Gly Val Tyr
1               5

<210> SEQ ID NO 39
<211> LENGTH: 16
<212> TYPE: PRT
<213> ORGANISM: Mus musculus

<400> SEQUENCE: 39

Met Ile Trp Gly Asp Gly Thr Thr Asp Tyr Asn Ser Ala Leu Lys Ser
1               5                   10                  15

<210> SEQ ID NO 40
<211> LENGTH: 8
<212> TYPE: PRT
<213> ORGANISM: Mus musculus
```

<400> SEQUENCE: 40

Gly Arg Gln Phe Gly Phe Asp Tyr
1               5

<210> SEQ ID NO 41
<211> LENGTH: 36
<212> TYPE: DNA
<213> ORGANISM: Mus musculus

<400> SEQUENCE: 41
cagagtctgt tcaacagtag aacccgaaag aactac                             36

<210> SEQ ID NO 42
<211> LENGTH: 24
<212> TYPE: DNA
<213> ORGANISM: Mus musculus

<400> SEQUENCE: 42
aagcaatctt ataatcttcg gacg                                          24

<210> SEQ ID NO 43
<211> LENGTH: 24
<212> TYPE: DNA
<213> ORGANISM: Mus musculus

<400> SEQUENCE: 43
gggttctcat taaccgacta tggt                                          24

<210> SEQ ID NO 44
<211> LENGTH: 21
<212> TYPE: DNA
<213> ORGANISM: Mus musculus

<400> SEQUENCE: 44 atatgggtg atggaaccac a                                              21

<210> SEQ ID NO 45
<211> LENGTH: 30
<212> TYPE: DNA
<213> ORGANISM: Mus musculus

<400> SEQUENCE: 45
gccaggggta gacagttcgg gtttgactac                                    30

<210> SEQ ID NO 46
<211> LENGTH: 336
<212> TYPE: DNA
<213> ORGANISM: Mus musculus

<400> SEQUENCE: 46
gacattgtga tgtcacagtc tccatcctcc ctggctgtgt cagcaggaga gaaggtcact    60
atgaggtgca atccagtca gagtctgttc aacagtagaa cccgaaagaa ctacttggct   120
tggtaccaac agaaaccagg gcagtctcct aaactgctga tcttctgggc atccattagg   180
gaatctgggg tccctgatcg cttcacaggc agtggatctg ggacagattt cactctcacc   240
atcagcagtg tgcaggctga agacctggca gtttattact gcaagcaatc ttataatctt   300
cggacgttcg gtggaggcac caagctggaa atcaaa                            336

<210> SEQ ID NO 47
<211> LENGTH: 348

<212> TYPE: DNA
<213> ORGANISM: Mus musculus

<400> SEQUENCE: 47

```
caggtgcagc tgaaggagtc tgggcctggc ctggtggcgc cctcacagag cctgtccatc    60
acatgcaccg tctcagggtt ctcattaacc gactatggtg tatactgggt tcgccagcct   120
ccaggaaagg gtctggagtg gctgggaatg atatggggtg atggaaccac agactataat   180
tcagctctca aatccagact gagcatcagt aaggacaact ccaagagcca agttttctta   240
aaaatgaaca ctctgcaaac tgatgacaca gccaggtatt actgtgccag gggtagacag   300
ttcgggtttg actactgggg ccaaggcacc acgctcacag tctcctca               348
```

<210> SEQ ID NO 48
<211> LENGTH: 51
<212> TYPE: DNA
<213> ORGANISM: Mus musculus

<400> SEQUENCE: 48

```
aaatccagtc agagtctgtt caacagtaga acccgaaaga actacttggc t            51
```

<210> SEQ ID NO 49
<211> LENGTH: 21
<212> TYPE: DNA
<213> ORGANISM: Mus musculus

<400> SEQUENCE: 49

```
tgggcatcca ttagggaatc t                                             21
```

<210> SEQ ID NO 50
<211> LENGTH: 24
<212> TYPE: DNA
<213> ORGANISM: Mus musculus

<400> SEQUENCE: 50

```
aagcaatctt ataatcttcg gacg                                          24
```

<210> SEQ ID NO 51
<211> LENGTH: 15
<212> TYPE: DNA
<213> ORGANISM: Mus musculus

<400> SEQUENCE: 51

```
gactatggtg tatac                                                    15
```

<210> SEQ ID NO 52
<211> LENGTH: 48
<212> TYPE: DNA
<213> ORGANISM: Mus musculus

<400> SEQUENCE: 52

```
atgatatggg gtgatggaac cacagactat aattcagctc tcaaatcc                48
```

<210> SEQ ID NO 53
<211> LENGTH: 24
<212> TYPE: DNA
<213> ORGANISM: Mus musculus

<400> SEQUENCE: 53

```
ggtagacagt tcgggtttga ctac                                          24
```

<210> SEQ ID NO 54

<211> LENGTH: 359
<212> TYPE: PRT
<213> ORGANISM: Mus musculus

<400> SEQUENCE: 54

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser Gln Leu Lys Ser Gly Ser Gly
        115                 120                 125

Ser Glu Ser Lys Ser Thr Asp Ile Val Met Thr Gln Ser Pro Ser Ser
130                 135                 140

Leu Ala Val Ser Leu Gly Glu Arg Ala Thr Met Ser Cys Lys Ser Ser
145                 150                 155                 160

Gln Ser Leu Phe Asn Ser Arg Thr Arg Lys Asn Tyr Leu Ala Trp Tyr
                165                 170                 175

Gln Gln Lys Pro Gly Gln Ser Pro Lys Leu Leu Ile Tyr Trp Ala Ser
            180                 185                 190

Ala Arg Asp Ser Gly Val Pro Ala Arg Phe Thr Gly Ser Gly Ser Glu
        195                 200                 205

Thr Tyr Phe Thr Leu Thr Ile Ser Arg Val Gln Ala Glu Asp Leu Ala
    210                 215                 220

Val Tyr Tyr Cys Met Gln Ser Phe Asn Leu Arg Thr Phe Gly Gln Gly
225                 230                 235                 240

Thr Lys Val Glu Ile Lys Thr Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu His His His His His His
        355
```

<210> SEQ ID NO 55
<211> LENGTH: 1077
<212> TYPE: DNA

<213> ORGANISM: Mus musculus

<400> SEQUENCE: 55

```
gaggtgcagc tggtggagtc tgccggagga ctggtgcagc ccggcagaag cctgagactg      60
agctgcaccg ccagcggctt caccttcacc gacaactaca tgtcctgggt gcgccaggcc     120
cctggaaagg cctggaatgg ggtgggcttc atccggaaca aggccaacgg ctacaccaca     180
gagtacgccg ccagcgtgaa gggccggttc accatcagcc gggacgacag caagagcatt     240
gcctacctgc agatgaacag cctgaaaacc gaggacaccg ccgtgtacta ctgcgccagg     300
gacgtgggca gcaactactt cgactactgg ggccagggca cactggtgac cgtgtctagc     360
caattgaaaa gcagcggcag cggtagcgaa agcaagtcga ccgacatcgt gatgacccag     420
agccccagca gcctggccgt gtctctgggc gagcgggcca ccatgagctg caagagcagc     480
cagagcctgt tcaacagccg gacccggaag aactacctgg cctggtatca gcagaagccc     540
ggccagtccc ccaagctgct gatctactgg gccagcgcca gagatagcgg cgtgcccgct     600
cgctttaccg gcagcggcag cgagacctac ttcaccctga ccatcagccg ggtgcaggcc     660
gaggacctcg ccgtgtacta ctgcatgcag agcttcaacc tgcggacctt cggccagggc     720
accaaggtgg agatcaagac cgtacggtg gccgctccca gcgtgttcat cttccccca      780
agcgacgagc agctgaagag cggcaccgcc agcgtggtgt gtctgctgaa caacttctac     840
cccagggagg ccaaggtgca gtggaaggtg acaacgccc tgcagagcgg caacagccag     900
gagagcgtca ccgagcagga cagcaaggac tccacctaca gcctgagcag caccctgacc     960
ctgagcaagg ccgactacga aagcacaag gtgtacgcct gtgaggtgac ccaccagggc    1020
ctgtccagcc ccgtgaccaa gagcttcaac aggggcgagc accatcatca ccaccat      1077
```

<210> SEQ ID NO 56
<211> LENGTH: 446
<212> TYPE: PRT
<213> ORGANISM: Mus musculus

<400> SEQUENCE: 56

```
Glu Val Asn Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Asn
             20                  25                  30

Tyr Met Ser Trp Val Arg Gln Pro Gly Lys Ala Leu Glu Trp Leu
         35                  40                  45

Gly Phe Ile Arg Asn Lys Ala Asn Gly Tyr Thr Thr Asp Tyr Ser Ala
     50                  55                  60

Ser Val Arg Gly Arg Phe Thr Ile Ser Arg Asp Asn Ser Lys Ser Ile
 65                  70                  75                  80

Leu Tyr Leu Gln Met Asn Ala Leu Arg Ala Glu Asp Ser Ala Thr Tyr
                 85                  90                  95

Tyr Cys Ala Arg Asp Val Gly Ser Asn Tyr Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 57
<211> LENGTH: 446
<212> TYPE: PRT
<213> ORGANISM: Mus musculus

<400> SEQUENCE: 57

Glu Val Asn Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Asn
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Arg Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95
```

```
Tyr Cys Ala Arg Asp Val Gly Ser Asn Tyr Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 58
<211> LENGTH: 445
<212> TYPE: PRT
<213> ORGANISM: Mus musculus

<400> SEQUENCE: 58

Glu Val Asn Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Asn
            20                  25                  30
```

```
Tyr Met Ser Trp Val Arg Gln Pro Gly Lys Ala Leu Glu Trp Leu
        35                  40                  45
Gly Phe Ile Arg Asn Lys Ala Asn Gly Tyr Thr Thr Asp Tyr Ser Ala
 50                  55                  60
Ser Val Arg Gly Arg Phe Thr Ile Ser Arg Asp Asn Ser Gln Ser Ile
 65                  70                  75                  80
Leu Tyr Leu Gln Met Asn Ala Leu Arg Ala Glu Asp Ser Ala Thr Tyr
                 85                  90                  95
Tyr Cys Ala Arg Asp Val Gly Ser Asn Tyr Phe Asp Tyr Trp Gly Gln
                100                 105                 110
Gly Thr Thr Leu Thr Val Ser Ser Ala Ser Thr Lys Gly Pro Ser Val
                115                 120                 125
Phe Pro Leu Ala Pro Cys Ser Arg Ser Thr Ser Glu Ser Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Asn Phe Gly Thr Gln Thr Tyr Thr Cys Asn Val Asp His Lys
                195                 200                 205
Pro Ser Asn Thr Lys Val Asp Lys Thr Val Glu Arg Lys Cys Cys Val
                210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Gln Phe Asn Trp Tyr Val Asp Gly Val Glu Val His Asn Ala Lys Thr
                275                 280                 285
Lys Pro Arg Glu Glu Gln Phe Asn Ser Thr Phe Arg Val Val Ser Val
                290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
                340                 345                 350
Ser Arg Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly
                435                 440                 445
```

<210> SEQ ID NO 59
<211> LENGTH: 219
<212> TYPE: PRT
<213> ORGANISM: Mus musculus

<400> SEQUENCE: 59

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Asp Ser Gly Val
    50                  55                  60

Pro Ala Arg Phe Thr Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 60
<211> LENGTH: 1341
<212> TYPE: DNA
<213> ORGANISM: Mus musculus

<400> SEQUENCE: 60
gaagtgaacc tggtggagtc tggcggcgga ctggtgcagc tggggggcag cctgagactg      60
agctgcgcca cctccggctt caccttcacc gacaactaca tgagctgggt gcgccagccc     120
cctggcaagg ccctggaatg gctgggcttc atccggaaca aggccaacgg ctacaccacc     180
gactacagcg ccagcgtgcg gggcagattc accatcagcc gggacaacag ccagagcatc     240
ctgtacctgc agatgaacgc cctgcgggcc gaggacagcg ccacctacta ctgtgcccgg     300
gacgtgggca gcaactactt cgactactgg ggccagggca ccacactgac cgtgtccagc     360
gccagcacca agggcccaag cgtgttcccc ctggccccct gctccagaag caccagcgag     420
agcacagccg ccctgggctg cctggtgaag gactacttcc ccgagcccgt gaccgtgtcc     480
tggaacagcg gagccctgac cagcggcgtg cacaccttcc cgccgtgct gcagagcagc     540 ggcctgtaca gcctgagcag cgtggtgacc gtgcccagca gcagcctggg caccaagacc     600
tacacctgta acgtggacca caagcccagc aacaccaagg tggacaagag ggtggagagc     660

```
aagtacggcc caccctgccc cagctgccca gcccccgagt tcctgggcgg acccagcgtg     720
ttcctgttcc cccccaagcc caaggacacc ctgatgatca gcagaacccc cgaggtgacc     780
tgtgtggtgg tggacgtgtc ccaggaggac cccgaggtcc agttcaactg gtacgtggac     840
ggcgtggagg tgcacaacgc caagaccaag cccagagagg agcagtttaa cagcacctac     900
cgggtggtgt ccgtgctgac cgtgctgcac caggactggc tgaacggcaa agagtacaag     960
tgtaaggtct ccaacaaggg cctgccaagc agcatcgaaa agaccatcag caaggccaag    1020
ggccagccta gagagcccca ggtctacacc ctgccaccca gccaagagga gatgaccaag    1080
aaccaggtgt ccctgacctg tctggtgaag ggcttctacc caagcgacat cgccgtggag    1140
tgggagagca acggccagcc cgagaacaac tacaagacca cccccccagt gctggacagc    1200
gacggcagct tcttcctgta cagcaggctg accgtggaca gtccagatg gcaggagggc    1260 aacgtcttta gctgctccgt gatgcacgag gccctgcaca accactacac ccagaagagc    1320
ctgagcctgt ccctgggctg a                                              1341

<210> SEQ ID NO 61
<211> LENGTH: 1341
<212> TYPE: DNA
<213> ORGANISM: Mus musculus

<400> SEQUENCE: 61
gaagtgaacc tggtggagtc tggcggcgga ctggtgcagc ctgggggcag cctgagactg      60
agctgcgcca cctccggctt caccttcacc gacaactaca tgagctgggt gcgccagccc     120
cctggcaagg ccctggaatg gctgggcttc atccggaaca aggccaacgg ctacaccacc     180
gactacagcg ccagcgtgcg gggcagattc accatcagcc gggacaacag ccagagcatc     240
ctgtacctgc agatgaacgc cctgcgggcc gaggacagcg ccacctacta ctgtgcccgg     300
gacgtgggca gcaactactt cgactactgg ggccagggca ccactgac cgtgtccagc      360 gccagcacca agggcccaag cgtgttcccc ctggccccct gctccagaag caccagcgag     420
agcacagccg ccctgggctg cctggtgaag gactacttcc ccgagcccgt gaccgtgtcc     480
tggaacagcg gagccctgac cagcggcgtg cacaccttcc ccgccgtgct gcagagcagc     540
ggcctgtaca gcctgagcag cgtggtgacc gtgcccagca gcagcctggg caccaagacc     600
tacacctgta acgtggacca caagcccagc aacaccaagg tggacaagag ggtggagagc     660
aagtacggcc cacccctgccc ccctgccca gcccccgagt tcctgggcgg acccagcgtg    720
ttcctgttcc cccccaagcc caaggacacc ctgatgatca gcagaacccc cgaggtgacc    780
tgtgtggtgg tggacgtgtc ccaggaggac cccgaggtcc agttcaactg gtacgtggac    840
ggcgtggagg tgcacaacgc caagaccaag cccagagagg agcagtttaa cagcacctac    900
cgggtggtgt ccgtgctgac cgtgctgcac caggactggc tgaacggcaa agagtacaag    960
tgtaaggtct ccaacaaggg cctgccaagc agcatcgaaa agaccatcag caaggccaag   1020
ggccagccta gagagcccca ggtctacacc ctgccaccca gccaagagga gatgaccaag   1080
aaccaggtgt ccctgacctg tctggtgaag ggcttctacc caagcgacat cgccgtggag   1140
tgggagagca acggccagcc cgagaacaac tacaagacca cccccccagt gctggacagc   1200
gacggcagct tcttcctgta cagcaggctg accgtggaca gtccagatg gcaggagggc    1260 aacgtcttta gctgctccgt gatgcacgag gccctgcaca accactacac ccagaagagc   1320
ctgagcctgt ccctgggctg a                                              1341
```

<210> SEQ ID NO 62
<211> LENGTH: 1338
<212> TYPE: DNA
<213> ORGANISM: Mus musculus

<400> SEQUENCE: 62

| | | | | | |
|---|---|---|---|---|---|
| gaagtgaacc | tggtggagtc | tggcggcgga | ctggtgcagc | ctgggggcag | cctgagactg | 60 |
| agctgcgcca | cctccggctt | caccttcacc | gacaactaca | tgagctgggt | gcgccagccc | 120 |
| cctggcaagg | ccctggaatg | gctgggcttc | atccggaaca | aggccaacgg | ctacaccacc | 180 |
| gactacagcg | ccagcgtgcg | gggcagattc | accatcagcc | gggacaacag | ccagagcatc | 240 |
| ctgtacctgc | agatgaacgc | cctgcgggcc | gaggacagcg | ccacctacta | ctgtgcccgg | 300 |
| gacgtgggca | gcaactactt | cgactactgg | ggcagggca | ccacactgac | cgtgtccagc | 360 |
| gccagcacca | agggcccaag | cgtgttcccc | ctggccccct | gctccagaag | caccagcgag | 420 |
| agcacagccg | ccctgggctg | cctggtgaag | gactacttcc | ccgagcccgt | gaccgtgtcc | 480 |
| tggaacagcg | gagccctgac | cagcggcgtg | cacaccttcc | ccgccgtgct | gcagagcagc | 540 |
| ggcctgtaca | gcctgagcag | cgtggtgacc | gtgccaagca | gcaacttcgg | cacccagacc | 600 |
| tacacctgta | acgtggacca | caagcccagc | aacaccaagg | tggacaagac | cgtggagagg | 660 |
| aagtgctgtg | tggagtgccc | ccctgccca | gccccccag | tggccggacc | cagcgtgttc | 720 |
| ctgttccccc | ccaagcccaa | ggacaccctg | atgatcagca | gaaccccga | ggtgacctgt | 780 |
| gtggtggtgg | acgtgtccca | cgaggacccc | gaggtgcagt | tcaactggta | cgtggacggc | 840 |
| gtggaggtgc | acaacgccaa | gaccaagccc | agagaggagc | agtttaacag | caccttccgg | 900 |
| gtggtgtccg | tgctgaccgt | ggtgcaccag | gactggctga | acggcaagga | gtacaagtgt | 960 |
| aaggtctcca | caagggcct | gccagccccc | atcgaaaaga | ccatcagcaa | gaccaaggga | 1020 |
| cagccaagag | agccacaggt | ctacaccctg | cccccagca | gggaggagat | gaccaagaac | 1080 |
| caggtgtccc | tgacctgtct | ggtgaagggc | ttctacccaa | gcgacatcgc | cgtggagtgg | 1140 |
| gagagcaacg | gccagcccga | gaacaactac | aagaccaccc | cccaatgct | ggacagcgac | 1200 |
| ggcagcttct | tcctgtacag | caagctgaca | gtggacaaga | gcagatggca | gcagggcaac | 1260 |
| gtgttcagct | gctccgtgat | gcacgaggcc | ctgcacaacc | actacaccca | gaagagcctg | 1320 |
| agcctgtccc | caggctga | | | | | 1338 |

<210> SEQ ID NO 63
<211> LENGTH: 660
<212> TYPE: DNA
<213> ORGANISM: Mus musculus

<400> SEQUENCE: 63

| | | | | | |
|---|---|---|---|---|---|
| gacatcgtga | tgagccagag | ccccagcagc | ctggccgtgt | ctgccggcga | gaaagtgacc | 60 |
| atgagctgca | agagcagcca | gagcctgttc | aacagccgga | cccggaagaa | ctacctggcc | 120 |
| tggtatcagc | agaagcccgg | ccagtccccc | aagctgctga | tctactgggc | cagcgccaga | 180 |
| gacagcggcg | tgcccgccag | attcaccggc | agcggcagcg | agacatactt | caccctgacc | 240 |
| atcagccggg | tgcaggccga | ggatctggcc | gtgtactact | gcatgcagag | cttcaacctg | 300 |
| cggacctttg | gcggcggaac | aaagctggaa | atcaagcgta | cggtggccgc | tcccagcgtg | 360 |
| ttcatcttcc | cccaagcga | cgagcagctg | aagagcggca | ccgccagcgt | ggtgtgtctg | 420 |
| ctgaacaact | tctaccccag | ggaggccaag | gtgcagtgga | aggtggacaa | cgccctgcag | 480 |
| agcggcaaca | gccaggagag | cgtcaccgag | caggacagca | aggactccac | ctacagcctg | 540 |

```
agcagcaccc tgaccctgag caaggccgac tacgagaagc acaaggtgta cgcctgtgag    600
gtgacccacc agggcctgtc cagccccgtg accaagagct tcaacagggg cgagtgctga    660
```

<210> SEQ ID NO 64
<211> LENGTH: 120
<212> TYPE: PRT
<213> ORGANISM: Mus musculus

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser
        115                 120

<210> SEQ ID NO 65
<211> LENGTH: 112
<212> TYPE: PRT
<213> ORGANISM: Mus musculus

<400> SEQUENCE: 65

Asp Ile Val Met Thr Gln Ser Pro Ser Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Asp Ser Gly Val
    50                  55                  60

Pro Ala Arg Phe Thr Gly Ser Gly Ser Glu Tyr Thr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
            100                 105                 110

<210> SEQ ID NO 66
<211> LENGTH: 112
<212> TYPE: PRT
<213> ORGANISM: Mus musculus

<400> SEQUENCE: 66

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Phe Asn Ser
            20                  25                  30

```
Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Ala Arg Asp Ser Gly Val
 50                  55                  60

Pro Asp Arg Phe Ser Gly Ser Gly Ser Glu Thr Tyr Phe Thr Leu Thr
 65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
                100                 105                 110

<210> SEQ ID NO 67
<211> LENGTH: 446
<212> TYPE: PRT
<213> ORGANISM: Mus musculus

<400> SEQUENCE: 67

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Thr Asp Asn
                20                  25                  30

Tyr Met Ser Trp Val Arg Gln Ala Pro Gly Lys Gly Leu Glu Trp Val
            35                  40                  45

Gly Phe Ile Arg Asn Lys Ala Asn Gly Tyr Thr Thr Glu Tyr Ala Ala
 50                  55                  60

Ser Val Lys Gly Arg Phe Thr Ile Ser Arg Asp Asn Ser Lys Ser Ile
 65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
 210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
```

```
                290                 295                 300
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
            435                 440                 445

<210> SEQ ID NO 68
<211> LENGTH: 446
<212> TYPE: PRT
<213> ORGANISM: Mus musculus

<400> SEQUENCE: 68

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

-continued

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 69
<211> LENGTH: 445
<212> TYPE: PRT
<213> ORGANISM: Mus musculus

<400> SEQUENCE: 69

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
            210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
            290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 70
<211> LENGTH: 219
<212> TYPE: PRT
<213> ORGANISM: Mus musculus

<400> SEQUENCE: 70

Asp Ile Val Met Thr Gln Ser Pro Ser Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Ala Arg Asp Ser Gly Val
            50                  55                  60

Pro Ala Arg Phe Thr Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln

```
            85                  90                  95
Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 71
<211> LENGTH: 219
<212> TYPE: PRT
<213> ORGANISM: Mus musculus

<400> SEQUENCE: 71

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

Pro Asp Arg Phe Ser Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
            85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 72
<211> LENGTH: 360
```

<212> TYPE: DNA
<213> ORGANISM: Mus musculus

<400> SEQUENCE: 72

```
gaggtgcagc tggtggagtc tggcggagga ctggtgcagc ccggcagaag cctgagactg        60
agctgcaccg ccagcggctt caccttcacc gacaactaca tgtcctgggt gcgccaggcc       120
cctggaaagg gcctggaatg ggtgggcttc atccggaaca aggccaacgg ctacaccaca       180
gagtacgccg ccagcgtgaa gggccggttc accatcagcc gggacaacag caagagcatt       240
gcctacctgc agatgaacag cctgaaaacc gaggacaccg ccgtgtacta ctgcgccagg       300
gacgtgggca gcaactactt cgactactgg ggccagggca cactggtgac cgtgtctagc       360
```

<210> SEQ ID NO 73
<211> LENGTH: 336
<212> TYPE: DNA
<213> ORGANISM: Mus musculus

<400> SEQUENCE: 73

```
gacatcgtga tgacccagag ccccagcagc ctggccgtgt ctctgggcga gcgggccacc        60
atgagctgca gagcagcca gagcctgttc aacagccgga cccggaagaa ctacctggcc       120
tggtatcagc agaagcccgg ccagtccccc aagctgctga tctactgggc cagcgccaga       180
gatagcggcg tgcccgctcg ctttaccggc agcggcagcg agacctactt cacccctgacc      240
atcagccggg tgcaggccga ggacctcgcc gtgtactact gcatgcagag cttcaacctg       300
cggaccttcg gccagggcac caaggtggag atcaag                                  336
```

<210> SEQ ID NO 74
<211> LENGTH: 336
<212> TYPE: DNA
<213> ORGANISM: Mus musculus

<400> SEQUENCE: 74

```
gacatcgtga tgacccagtc ccccgactcc ctggccgtgt ctctgggcga gcgggccacc        60
atgtcctgca gtcctcccca gtccctgttc aactcccgga cccggaagaa ctacctggcc       120
tggtatcagc agaagcccgg ccagcccccc aagctgctga tctactgggc ctctgctaga       180
gactctggcg tgcccgacag attctccggc tccggcagcg agacatactt cacccctgacc      240
atctcccggg tgcaggccga ggatctggcc gtgtactact gcatgcagtc cttcaacctg       300
cggaccttcg gccagggcac caaggtggaa atcaag                                  336
```

<210> SEQ ID NO 75
<211> LENGTH: 1341
<212> TYPE: DNA
<213> ORGANISM: Mus musculus

<400> SEQUENCE: 75

```
gaggtgcagc tggtggagtc tggcggagga ctggtgcagc ccggcagaag cctgagactg        60
agctgcaccg ccagcggctt caccttcacc gacaactaca tgtcctgggt gcgccaggcc       120
cctggaaagg gcctggaatg ggtgggcttc atccggaaca aggccaacgg ctacaccaca       180
gagtacgccg ccagcgtgaa gggccggttc accatcagcc gggacaacag caagagcatt       240
gcctacctgc agatgaacag cctgaaaacc gaggacaccg ccgtgtacta ctgcgccagg       300
gacgtgggca gcaactactt cgactactgg ggccagggca cactggtgac cgtgtctagc       360
gccagcacca agggcccaag cgtgttcccc ctggccccct gctccagaag caccagcgag       420
```

| | |
|---|---|
| agcacagccg cccctgggctg cctggtgaag gactacttcc ccgagcccgt gaccgtgtcc | 480 |
| tggaacagcg gagccctgac cagcggcgtg cacaccttcc ccgccgtgct gcagagcagc | 540 |
| ggcctgtaca gcctgagcag cgtggtgacc gtgcccagca gcagcctggg caccaagacc | 600 |
| tacacctgta acgtggacca caagcccagc aacaccaagg tggacaagag ggtggagagc | 660 |
| aagtacggcc accctgccc cagctgccca gcccccgagt tcctgggcgg acccagcgtg | 720 |
| ttcctgttcc cccccaagcc caaggacacc ctgatgatca gcagaacccc cgaggtgacc | 780 |
| tgtgtggtgg tggacgtgtc ccaggaggac cccgaggtcc agttcaactg gtacgtggac | 840 |
| ggcgtggagg tgcacaacgc caagaccaag cccagagagg agcagtttaa cagcacctac | 900 |
| cgggtggtgt ccgtgctgac cgtgctgcac caggactggc tgaacggcaa agagtacaag | 960 |
| tgtaaggtct ccaacaaggg cctgccaagc agcatcgaaa agaccatcag caaggccaag | 1020 |
| ggccagccta gagagcccca ggtctacacc ctgccaccca gccaagagga gatgaccaag | 1080 |
| aaccaggtgt ccctgacctg tctggtgaag ggcttctacc caagcgacat cgccgtggag | 1140 |
| tgggagagca acggccagcc cgagaacaac tacaagacca cccccccagt gctggacagc | 1200 |
| gacggcagct tcttcctgta cagcaggctg accgtggaca gtccagatg gcaggagggc | 1260 |
| aacgtctttta gctgctccgt gatgcacgag gccctgcaca accactacac ccagaagagc | 1320 |
| ctgagcctgt ccctgggctg a | 1341 |

<210> SEQ ID NO 76
<211> LENGTH: 1341
<212> TYPE: DNA
<213> ORGANISM: Mus musculus

<400> SEQUENCE: 76

| | |
|---|---|
| gaggtgcagc tggtggagtc tggcggagga ctggtgcagc ccggcagaag cctgagactg | 60 |
| agctgcaccg ccagcggctt caccttcacc gacaactaca tgtcctgggt cgccaggcc | 120 |
| cctggaaagg gcctggaatg ggtgggcttc atccggaaca aggccaacgg ctacaccaca | 180 |
| gagtacgccg ccagcgtgaa gggccggttc accatcagcc gggacaacag caagagcatt | 240 |
| gcctacctgc agatgaacag cctgaaaacc gaggacaccg ccgtgtacta ctgcgccagg | 300 |
| gacgtgggca gcaactactt cgactactgg ggccagggca cactggtgac cgtgtctagc | 360 |
| gccagcacca agggcccaag cgtgttcccc ctggccccct gctccagaag caccagcgag | 420 |
| agcacagccg cccctgggctg cctggtgaag gactacttcc ccgagcccgt gaccgtgtcc | 480 |
| tggaacagcg gagccctgac cagcggcgtg cacaccttcc ccgccgtgct gcagagcagc | 540 |
| ggcctgtaca gcctgagcag cgtggtgacc gtgcccagca gcagcctggg caccaagacc | 600 |
| tacacctgta acgtggacca caagcccagc aacaccaagg tggacaagag ggtggagagc | 660 |
| aagtacggcc accctgccc cccctgccca gcccccgagt tcctgggcgg acccagcgtg | 720 |
| ttcctgttcc cccccaagcc caaggacacc ctgatgatca gcagaacccc cgaggtgacc | 780 |
| tgtgtggtgg tggacgtgtc ccaggaggac cccgaggtcc agttcaactg gtacgtggac | 840 |
| ggcgtggagg tgcacaacgc caagaccaag cccagagagg agcagtttaa cagcacctac | 900 |
| cgggtggtgt ccgtgctgac cgtgctgcac caggactggc tgaacggcaa agagtacaag | 960 |
| tgtaaggtct ccaacaaggg cctgccaagc agcatcgaaa agaccatcag caaggccaag | 1020 |
| ggccagccta gagagcccca ggtctacacc ctgccaccca gccaagagga gatgaccaag | 1080 |
| aaccaggtgt ccctgacctg tctggtgaag ggcttctacc caagcgacat cgccgtggag | 1140 |
| tgggagagca acggccagcc cgagaacaac tacaagacca cccccccagt gctggacagc | 1200 |

| | |
|---|---|
| gacggcagct tcttcctgta cagcaggctg accgtggaca agtccagatg gcaggagggc | 1260 |
| aacgtctttta gctgctccgt gatgcacgag gccctgcaca accactacac ccagaagagc | 1320 |
| ctgagcctgt ccctgggctg a | 1341 |

<210> SEQ ID NO 77
<211> LENGTH: 1338
<212> TYPE: DNA
<213> ORGANISM: Mus musculus

<400> SEQUENCE: 77

| | |
|---|---|
| gaggtgcagc tggtggagtc tggcggagga ctggtgcagc ccggcagaag cctgagactg | 60 |
| agctgcaccg ccagcggctt caccttcacc gacaactaca tgtcctgggt gcgccaggcc | 120 |
| cctggaaagg gcctggaatg ggtgggcttc atccggaaca aggccaacgg ctacaccaca | 180 |
| gagtacgccg ccagcgtgaa gggccggttc accatcagcc gggacaacag caagagcatt | 240 |
| gcctacctgc agatgaacag cctgaaaacc gaggacaccg ccgtgtacta ctgcgccagg | 300 |
| gacgtgggca gcaactactt cgactactgg ggccagggca cactggtgac cgtgtctagc | 360 |
| gccagcacca agggcccaag cgtgttcccc ctggccccct gctccagaag caccagcgag | 420 |
| agcacagccg ccctgggctg cctggtgaag gactacttcc ccgagcccgt gaccgtgtcc | 480 |
| tggaacagcg gagccctgac cagcggcgtg cacaccttcc ccgccgtgct gcagagcagc | 540 |
| ggcctgtaca gcctgagcag cgtggtgacc gtgccaagca gcaacttcgg cacccagacc | 600 |
| tacacctgta acgtggacca caagcccagc aacaccaagg tggacaagac cgtggagagg | 660 |
| aagtgctgtg tggagtgccc ccctgccca gcccccccag tggccggacc cagcgtgttc | 720 |
| ctgttccccc ccaagcccaa ggacaccctg atgatcagca gaacccccga ggtgacctgt | 780 |
| gtggtggtgg acgtgtccca cgaggacccc gaggtgcagt tcaactggta cgtggacggc | 840 |
| gtggaggtgc acaacgccaa gaccaagccc agagaggagc agtttaacag caccttccgg | 900 |
| gtggtgtccg tgctgaccgt ggtgcaccag gactggctga acggcaagga gtacaagtgt | 960 |
| aaggtctcca caagggcct gccagccccc atcgaaaaga ccatcagcaa gaccaaggga | 1020 |
| cagccaagag agccacaggt ctacaccctg cccccagca gggaggagat gaccaagaac | 1080 |
| caggtgtccc tgacctgtct ggtgaagggc ttctacccaa gcgacatcgc cgtggagtgg | 1140 |
| gagagcaacg gccagcccga gaacaactac aagaccaccc ccccaatgct ggacagcgac | 1200 |
| ggcagcttct tcctgtacag caagctgaca gtggacaaga gcagatggca gcagggcaac | 1260 |
| gtgttcagct gctccgtgat gcacgaggcc ctgcacaacc actacaccca gaagagcctg | 1320 |
| agcctgtccc caggctga | 1338 |

<210> SEQ ID NO 78
<211> LENGTH: 660
<212> TYPE: DNA
<213> ORGANISM: Mus musculus

<400> SEQUENCE: 78

| | |
|---|---|
| gacatcgtga tgacccagag ccccagcagc ctggccgtgt ctctgggcga gcgggccacc | 60 |
| atgagctgca gagcagcca gagcctgttc aacagccgga cccggaagaa ctacctggcc | 120 |
| tggtatcagc agaagcccgg ccagtccccc aagctgctga tctactgggc cagcgccaga | 180 |
| gatagcggcg tgcccgctcg ctttaccggc agcggcagcg agacctactt cacccctgacc | 240 |
| atcagccggg tgcaggccga ggacctcgcc gtgtactact gcatgcagag cttcaacctg | 300 |

```
cggaccttcg gccagggcac caaggtggag atcaagcgta cggtggccgc tcccagcgtg    360
ttcatcttcc ccccaagcga cgagcagctg aagagcggca ccgccagcgt ggtgtgtctg    420
ctgaacaact tctaccccag ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc acaaggtgta cgcctgtgag    600
gtgacccacc agggcctgtc cagccccgtg accaagagct caacaggggg cgagtgctga    660

<210> SEQ ID NO 79
<211> LENGTH: 660
<212> TYPE: DNA
<213> ORGANISM: Mus musculus

<400> SEQUENCE: 79
gacatcgtga tgacccagtc ccccgactcc ctggccgtgt ctctgggcga gcgggccacc     60
atgtcctgca gtcctcccca gtccctgttc aactcccgga cccggaagaa ctacctggcc    120
tggtatcagc agaagcccgg ccagccccc aagctgctga tctactgggc ctctgctaga    180
gactctggcg tgcccgacag attctccggc tccggcagcg agacatactt caccctgacc    240
atctcccggg tgcaggccga ggatctggcc gtgtactact gcatgcagtc cttcaacctg    300
cggaccttcg gccagggcac caaggtggaa atcaagcgta cggtggccgc tcccagcgtg    360
ttcatcttcc ccccaagcga cgagcagctg aagagcggca ccgccagcgt ggtgtgtctg    420
ctgaacaact tctaccccag ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc acaaggtgta cgcctgtgag    600
gtgacccacc agggcctgtc cagccccgtg accaagagct caacaggggg cgagtgctga    660

<210> SEQ ID NO 80
<211> LENGTH: 450
<212> TYPE: PRT
<213> ORGANISM: Mus musculus

<400> SEQUENCE: 80

Glu Val Asn Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Asn
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Arg Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Val Gly Ser Asn Tyr Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 81
<211> LENGTH: 1353
<212> TYPE: DNA
<213> ORGANISM: Mus musculus

<400> SEQUENCE: 81
gaagtgaacc tggtggagtc tggcggcgga ctggtgcagc ctgggggcag cctgagactg      60
agctgcgcca cctccggctt caccttcacc gacaactaca tgagctgggt gcgccagccc     120
cctggcaagg ccctggaatg gctgggcttc atccggaaca aggccaacgg ctacaccacc     180
gactacagcg ccagcgtgcg gggcagattc accatcagcc gggacaacag ccagagcatc     240
ctgtacctgc agatgaacgc cctgcgggcc gaggacagcg ccacctacta ctgtgcccgg     300
gacgtgggca gcaactactt cgactactgg ggccagggcc cacactgac cgtgtccagc     360 gccagcacca agggcccctc cgtgttcccg ctagccccca gcagcaagag caccagcggc     420
```

```
ggcacagccg ccctgggctg cctggtgaag gactacttcc ccgagcccgt gaccgtgtcc    480
tggaacagcg gagccctgac ctccggcgtg cacaccttcc ccgccgtgct gcagagcagc    540
ggcctgtaca gcctgagcag cgtggtgacc gtgcccagca gcagcctggg cacccagacc    600
tacatctgta acgtgaacca caagcccagc aacaccaagg tggacaagag agtggagccc    660
aagagctgtg acaagaccca cacctgcccc cctgcccag ccccgagct gctgggcgga     720 cccagcgtgt tcctgttccc ccccaagccc aaggacaccc tgatgatcag cagaaccccc    780
gaggtgacct gtgtggtgg gacgtgtcc cacgaggacc cagaggtgaa gttcaactgg     840
tacgtggacg gcgtggaggt gcacaacgcc aagaccaagc ccagagagga gcagtacaac    900
agcacctaca gggtggtgtc cgtgctgacc gtgctgcacc aggactggct gaacggcaag    960
gagtacaagt gtaaggtgtc caacaaggcc ctgccagccc caatcgaaaa gaccatcagc    1020
aaggccaagg gccagccaag agagcccag gtgtacaccc tgccacccag caggaggag      1080 atgaccaaga accaggtgtc cctgacctgt ctggtgaagg gcttctaccc aagcgacatc    1140
gccgtggagt gggagagcaa cggccagccc gagaacaact acaagaccac ccccccagtg    1200
ctggacagcg acggcagctt cttcctgtac agcaagctga ccgtggacaa gagcagatgg    1260
cagcagggca acgtgttcag ctgctccgtg atgcacgagg ccctgcacaa ccactacacc    1320
cagaagagcc tgagcctgtc cccaggcaag tga                                 1353
```

<210> SEQ ID NO 82
<211> LENGTH: 112
<212> TYPE: PRT
<213> ORGANISM: Mus musculus

<400> SEQUENCE: 82

```
Asp Ile Val Met Thr Gln Ser Pro Asp Ser Leu Ala Val Ser Leu Gly
1               5                   10                  15

Glu Arg Ala Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

Pro Asp Arg Phe Thr Gly Ser Gly Ser Glu Thr Tyr Phe Thr Leu Thr
65                  70                  75                  80

Ile Ser Arg Val Gln Ala Glu Asp Val Ala Val Tyr Tyr Cys Met Gln
                85                  90                  95

Ser Phe Asn Leu Arg Thr Phe Gly Gln Gly Thr Lys Val Glu Ile Lys
                100                 105                 110
```

<210> SEQ ID NO 83
<211> LENGTH: 112
<212> TYPE: PRT
<213> ORGANISM: Mus musculus

<400> SEQUENCE: 83

```
Asp Ile Val Met Thr Gln Ser Pro Asp Ser Leu Ala Val Ser Leu Gly
1               5                   10                  15

Glu Arg Ala Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45
```

```
Pro Pro Lys Leu Leu Ile Tyr Trp Ala Ser Ala Arg Asp Ser Gly Val
    50                  55                  60

Pro Asp Arg Phe Thr Gly Ser Gly Ser Glu Tyr Phe Thr Leu Thr
 65              70                  75                  80

Ile Ser Ser Leu Gln Ala Glu Asp Leu Ala Val Tyr Tyr Cys Met Gln
                 85                  90                  95

Ser Phe Asn Leu Arg Thr Phe Gly Gln Gly Thr Lys Val Glu Ile Lys
            100                 105                 110
```

<210> SEQ ID NO 84
<211> LENGTH: 219
<212> TYPE: PRT
<213> ORGANISM: Mus musculus

<400> SEQUENCE: 84

```
Asp Ile Val Met Thr Gln Ser Pro Asp Ser Leu Ala Val Ser Leu Gly
 1               5                  10                  15

Glu Arg Ala Thr Met Ser Cys Lys Ser Gln Ser Leu Phe Asn Ser
                 20                  25                  30

Arg Thr Arg Lys Asn Tyr Leu Ala Trp Tyr Gln Gln Lys Pro Gly Gln
             35                  40                  45

Pro Pro Lys Leu Leu Ile Tyr Trp Ala Ser Ala Arg Asp Ser Gly Val
    50                  55                  60

Pro Asp Arg Phe Thr Gly Ser Gly Ser Glu Tyr Phe Thr Leu Thr
 65              70                  75                  80

Ile Ser Arg Val Gln Ala Glu Asp Val Ala Val Tyr Tyr Cys Met Gln
                 85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 85
<211> LENGTH: 219
<212> TYPE: PRT
<213> ORGANISM: Mus musculus

<400> SEQUENCE: 85

```
Asp Ile Val Met Thr Gln Ser Pro Asp Ser Leu Ala Val Ser Leu Gly
 1               5                  10                  15

Glu Arg Ala Thr Met Ser Cys Lys Ser Gln Ser Leu Phe Asn Ser
                 20                  25                  30

Arg Thr Arg Lys Asn Tyr Leu Ala Trp Tyr Gln Gln Lys Pro Gly Gln
             35                  40                  45
```

Pro Pro Lys Leu Leu Ile Tyr Trp Ala Ser Ala Arg Asp Ser Gly Val
    50                  55                  60

Pro Asp Arg Phe Thr Gly Ser Gly Ser Glu Thr Tyr Phe Thr Leu Thr
65                  70                  75                  80

Ile Ser Ser Leu Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 86
<211> LENGTH: 336
<212> TYPE: DNA
<213> ORGANISM: Mus musculus

<400> SEQUENCE: 86
gacatcgtga tgacccagtc ccccgactcc ctggccgtgt ctctgggcga gcgggccacc    60
atgtcctgca gtcctcccca gtccctgttc aactcccgga cccggaagaa ctacctggcc   120
tggtatcagc agaagcccgg ccagccccca aagctgctga tctactgggc ctctgctaga   180
gactctggcg tgcccgacag attcaccggc tccggcagcg agacatactt caccctgacc   240
atctcccggg tgcaggccga ggatgtggcc gtgtactact gcatgcagtc cttcaacctg   300
cggaccttcg gccagggcac caaggtggaa atcaag                             336

<210> SEQ ID NO 87
<211> LENGTH: 336
<212> TYPE: DNA
<213> ORGANISM: Mus musculus

<400> SEQUENCE: 87
gacatcgtga tgacccagtc ccccgactcc ctggccgtgt ctctgggcga gcgggccacc    60
atgtcctgca gtcctcccca gtccctgttc aactcccgga cccggaagaa ctacctggcc   120
tggtatcagc agaagcccgg ccagccccca aagctgctga tctactgggc ctctgctaga   180
gactctggcg tgcccgacag attcaccggc tccggcagcg agacatactt caccctgacc   240
atctccagcc tgcaggccga ggatctggcc gtgtactact gcatgcagtc cttcaacctg   300
cggaccttcg gccagggcac caaggtggaa atcaag                             336

<210> SEQ ID NO 88
<211> LENGTH: 657
<212> TYPE: DNA
<213> ORGANISM: Mus musculus

```
<400> SEQUENCE: 88
gacatcgtga tgacccagtc ccccgactcc ctggccgtgt ctctgggcga gcgggccacc      60
atgtcctgca gtcctcccca gtccctgttc aactcccgga cccggaagaa ctacctggcc     120
tggtatcagc agaagcccgg ccagcccccc aagctgctga tctactgggc ctctgctaga     180
gactctggcg tgcccgacag attcaccggc tccggcagcg agacatactt caccctgacc     240
atctcccggg tgcaggccga ggatgtggcc gtgtactact gcatgcagtc cttcaacctg     300
cggaccttcg gccagggcac caaggtggaa atcaagcgta cggtggccgc tcccagcgtg     360
ttcatcttcc ccccaagcga cgagcagctg aagagcggca ccgccagcgt ggtgtgtctg     420
ctgaacaact tctaccccag ggaggccaag gtgcagtgga aggtggacaa cgccctgcag     480
agcggcaaca gccaggagag cgtcaccgag caggacagca aggactccac ctacagcctg     540
agcagcaccc tgaccctgag caaggccgac tacgagaagc acaaggtgta cgcctgtgag     600
gtgacccacc agggcctgtc cagccccgtg accaagagct tcaacagggg cgagtgc       657

<210> SEQ ID NO 89
<211> LENGTH: 657
<212> TYPE: DNA
<213> ORGANISM: Mus musculus

<400> SEQUENCE: 89
gacatcgtga tgacccagtc ccccgactcc ctggccgtgt ctctgggcga gcgggccacc      60
atgtcctgca gtcctcccca gtccctgttc aactcccgga cccggaagaa ctacctggcc     120
tggtatcagc agaagcccgg ccagcccccc aagctgctga tctactgggc ctctgctaga     180
gactctggcg tgcccgacag attcaccggc tccggcagcg agacatactt caccctgacc     240
atctccagcc tgcaggccga ggatctggcc gtgtactact gcatgcagtc cttcaacctg     300
cggaccttcg gccagggcac caaggtggaa atcaagcgta cggtggccgc tcccagcgtg     360
ttcatcttcc ccccaagcga cgagcagctg aagagcggca ccgccagcgt ggtgtgtctg     420
ctgaacaact tctaccccag ggaggccaag gtgcagtgga aggtggacaa cgccctgcag     480
agcggcaaca gccaggagag cgtcaccgag caggacagca aggactccac ctacagcctg     540
agcagcaccc tgaccctgag caaggccgac tacgagaagc acaaggtgta cgcctgtgag     600
gtgacccacc agggcctgtc cagccccgtg accaagagct tcaacagggg cgagtgc       657

<210> SEQ ID NO 90
<211> LENGTH: 120
<212> TYPE: PRT
<213> ORGANISM: Mus musculus

<400> SEQUENCE: 90

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95
```

Tyr Cys Ala Arg Asp Val Gly Ser Asn Tyr Phe Asp Tyr Trp Gly Gln
                100                 105                 110

Gly Thr Leu Val Thr Val Ser Ser
        115                 120

<210> SEQ ID NO 91
<211> LENGTH: 360
<212> TYPE: DNA
<213> ORGANISM: Mus musculus

<400> SEQUENCE: 91
gaggtgcagc tggtggagtc tggcggagga ctggtgcagc ccggcagaag cctgagactg     60
agctgcaccg ccagcggctt caccttcacc gacaactaca tgtcctgggt gcgccaggcc    120
cctggaaagg gcctggaatg ggtgggcttc atccggaaca aggccaacgg ctacaccaca    180
gagtacgccg ccagcgtgaa ggccggttc accatcagcc gggacgacag caagagcatt    240
gcctacctgc agatgaacag cctgaaaacc gaggacaccg ccgtgtacta ctgcgccagg    300
gacgtgggca gcaactactt cgactactgg ggccagggca cactggtgac cgtgtctagc    360

<210> SEQ ID NO 92
<211> LENGTH: 450
<212> TYPE: PRT
<213> ORGANISM: Mus musculus

<400> SEQUENCE: 92

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 93
<211> LENGTH: 1350
<212> TYPE: DNA
<213> ORGANISM: Mus musculus

<400> SEQUENCE: 93
gaggtgcagc tggtggagtc tggcggagga ctggtgcagc ccggcagaag cctgagactg      60
agctgcaccg ccagcggctt caccttcacc gacaactaca tgtcctgggt cgcccaggcc     120
cctggaaagg gcctggaatg ggtgggcttc atccggaaca aggccaacgg ctacaccaca     180
gagtacgccg ccagcgtgaa gggccggttc accatcagcc gggacgacag caagagcatt     240
gcctacctgc agatgaacag cctgaaaacc gaggacaccg ccgtgtacta ctgcgccagg     300
gacgtgggca gcaactactt cgactactgg ggccagggca cactggtgac cgtgtctagc     360
gccagcacaa agggcccaag cgtgttcccg ctagccccca gcagcaagag caccagcggc     420
ggcacagccg ccctgggctg cctggtgaag gactacttcc ccgagcccgt gaccgtgtcc     480
tggaacagcg gagccctgac ctccggcgtg cacaccttcc ccgccgtgct gcagagcagc     540
ggcctgtaca gcctgagcag cgtggtgacc gtgcccagca gcagcctggg cacccagacc     600
tacatctgta acgtgaacca caagcccagc aacaccaagg tggacaagag agtggagccc     660
aagagctgtg acaagaccca cacctgcccc cctgcccag ccccgagct gctgggcgga      720 cccagcgtgt tcctgttccc ccccaagccc aaggacaccc tgatgatcag cagaaccccc     780
gaggtgacct gtgtggtggt ggacgtgtcc cacgaggacc cagaggtgaa gttcaactgg     840
```

| | | |
|---|---|---|
| tacgtggacg gcgtggaggt gcacaacgcc aagaccaagc ccagagagga gcagtacaac | 900 | |
| agcacctaca gggtggtgtc cgtgctgacc gtgctgcacc aggactggct gaacggcaag | 960 | |
| gagtacaagt gtaaggtgtc caacaaggcc ctgccagccc aatcgaaaa gaccatcagc | 1020 | |
| aaggccaagg gccagccaag agagcccag gtgtacaccc tgccacccag cagggaggag | 1080 | |
| atgaccaaga accaggtgtc cctgacctgt ctggtgaagg gcttctaccc aagcgacatc | 1140 | |
| gccgtggagt gggagagcaa cggccagccc gagaacaact acaagaccac ccccccagtg | 1200 | |
| ctggacagcg acggcagctt cttcctgtac agcaagctga ccgtggacaa gagcagatgg | 1260 | |
| cagcagggca acgtgttcag ctgctccgtg atgcacgagg ccctgcacaa ccactacacc | 1320 | |
| cagaagagcc tgagcctgtc cccaggcaag | 1350 | |

<210> SEQ ID NO 94
<211> LENGTH: 100
<212> TYPE: PRT
<213> ORGANISM: Homo sapiens

<400> SEQUENCE: 94

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 95
<211> LENGTH: 15
<212> TYPE: PRT
<213> ORGANISM: Homo sapiens

<400> SEQUENCE: 95

Tyr Phe Asp Tyr Trp Gly Gln Gly Thr Leu Val Thr Val Ser Ser
1               5                   10                  15

<210> SEQ ID NO 96
<211> LENGTH: 112
<212> TYPE: PRT
<213> ORGANISM: Mus musculus

<400> SEQUENCE: 96

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Asp Ser Gly Val
    50                  55                  60

Pro Ala Arg Phe Thr Gly Ser Gly Ser Glu Thr Tyr Phe Thr Leu Thr

```
                65                  70                  75                  80
Ile Ser Arg Val Gln Ala Glu Asp Leu Ala Val Tyr Tyr Cys Met Gln
                        85                  90                  95
Ser Phe Asn Leu Arg Thr Phe Gly Gln Gly Thr Lys Val Glu Ile Lys
                100                 105                 110

<210> SEQ ID NO 97
<211> LENGTH: 94
<212> TYPE: PRT
<213> ORGANISM: Homo sapiens

<400> SEQUENCE: 97

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
                20                  25                  30
Ser Asn Asn Lys Asn Tyr Leu Ala Trp Tyr Gln Gln Lys Pro Gly Gln
                35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys
                85                  90

<210> SEQ ID NO 98
<211> LENGTH: 12
<212> TYPE: PRT
<213> ORGANISM: Homo sapiens

<400> SEQUENCE: 98

Trp Thr Phe Gly Gln Gly Thr Lys Val Glu Ile Lys
1               5                   10
```

ANTIBODIES FOR THE TREATMENT OF HIV

CROSS REFERENCE TO RELATED APPLICATIONS

This application is a Continuation-In-Part of International Patent Application No. PCT/EP2010/055863, filed Apr. 29, 2010, and claims the benefit of U.S. Provisional Application No. 61/173,680, filed Apr. 29, 2009 and the priority of European Application No. 09159076.0 filed Apr. 29, 2009, the content of all of which is incorporated herein by reference.

The present invention relates to novel antibodies, in particular murine monoclonal antibodies, chimeric and humanized, able to bind specifically to chemokine receptors (CXCR) as well as the amino and nucleic acid sequences coding for such antibodies. From one aspect, the invention relates to novel antibodies, functional fragments or derivatives, able to bind specifically to the CXCR4 and having strong activity against human immunodeficiency virus (HIV) infection. The invention also comprises the use of such antibodies, functional fragments or derivatives as a medicament for the preventive and/or therapeutic treatment of HIV infection.

Chemokines are small, secreted peptides that control the migration of leukocytes along a chemical gradient of ligand, known as chemokine gradient, especially during immune reactions (Zlotnick A. et al., 2000). They are divided into two major subfamilies, CC and CXC, based on the position of their $NH_2$-terminal cysteine residues, and bind to G protein coupled receptors, whose two major sub families are designated CCR and CXCR. More than 50 human chemokines and 18 chemokine receptors have been discovered so far.

Several members of the chemokine receptor family function as co-receptors with the primary receptor CD4 to allow entry of various strains of HIV type 1 into the cells, the major co-receptors being CCR5 and CXCR4. T-cell tropic X4 HIV-1 use CD4 and CXCR4 for the entry into the cells, whereas macrophage-tropic R5 HIV-1 use CD4 and CCR5. Dual-tropic strains can use both CXCR4 and CCR5 as co-receptors. CCR3, CCR2, CCR8, CXCR6, CXCR7, CX3CR1 among other chemokine receptors can function as co-receptors by more restricted subset of HIV strains.

SDF-1, the natural ligand of CXCR4 as well as CCL3, CCL4, CCL4-L1, and CCL5 ligands for CCR5 are able to inhibit cell fusion and infection by various strains of HIV-1. These findings have encouraged the development of anti-HIV therapeutics targeting chemokine receptors leading to the approval of maraviroc (CELSENTRI®), a small molecule antagonist of CCR5 in combination with other anti-HIV-1 agents in patients infected by CCR5-tropic HIV-1. Nevertheless, maraviroc is neither used in patients infected by dual-tropic HIV-1 nor in patients infected by CXCR4-tropic HIV-1 (VIDAL 2009). So there is a clear medical need to extend this type of therapy in both X4-tropic and dual-tropic HIV infected patients by identifying CXCR4 antagonists able to inhibit X4-tropic HIV replication.

Chemokine receptor 4 (also known as fusin, CD184, LESTR or HUMSTR) exists as two isoforms comprising 352 or 360 amino acids. Residue Asn11 is glycosylated, residue Tyr21 is modified by the addition of a sulfate group and Cys 109 and 186 are bond with a disulfide bridge on the extracellular part of the receptor (Juarez J. et al., 2004).

This receptor is expressed by different kind of normal tissues, naïve, non-memory T-cells, regulatory T cells, B-cells, neutrophils, endothelial cells, primary monocytes, dendritic cells, Natural Killer cells, CD34+ hematopoietic stem cells and at a low level in heart, colon, liver, kidneys and brain. CXCR4 plays a key role in leukocytes trafficking, B cell lymphopoiesis and myelopoiesis.

The unique ligand of CXCR4 receptor described so far is the Stromal-cell-Derived Factor-1 (SDF-1) or CXCL12. SDF-1 is secreted in large amount in lymph node, bone marrow, liver, lung and to a less extent by kidneys, brain and skin. CXCR4 is also recognized by an antagonistic chemokine, the viral macrophage inflammatory protein II (vMIP-II) encoded by human herpesvirus type III.

As previously mentioned, CXCR4 receptor is the principal co-receptor for T-cell-tropic HIV-1 isolates (X4 viruses). Interfering with this receptor should inhibit X4 viruses replication in a very efficient way.

One of the inventive aspect of the present invention is to generate mouse monoclonal antibodies (Mabs) inhibiting HIV replication. The invention encompasses a CXCR4 Mab 515H7 (or fragments thereof) able to bind to CXCR4 homodimers, and having strong activities against HIV infection. The invention also encompasses a CXCR4 Mab 301aE5 (or fragments thereof) able to bind to CXCR4 homodimers, and having strong activities against HIV infection.

Surprisingly, inventors have managed to generate monoclonal antibodies capable of binding to CXCR4 but also capable of inducing conformational changes of the CXCR4 homodimers and able to inhibit primary isolate X4-HIV-1 replication in PBMC. More particularly, the antibodies of the invention can also be able to inhibit primary isolate X4/R5-HIV-1 replication in PBMC.

Preferably, CXCR4 compound is one of the two human CXCR4 isoforms selected from the group consisting of:

the chemokine (C-X-C motif) receptor 4 isoform b [*Homo sapiens*] having the sequence as depicted under the Genbank accession number NP_003458 SEQ ID No. 27:

```
MEGISIYTSDNYTEEMGSGDYDSMKEPCFREENANFNKIFLPTIYSIIFL

TGIVGNGLVILVMGYQKKLRSMTDKYRLHLSVADLLFVITLPFWAVDAVA

NWYFGNFLCKAVHVIYTVNLYSSVLILAFISLDRYLAIVHATNSQRPRKL

LAEKVVYVGVWIPALLLTIPDFIFANVSEADDRYICDRFYPNDLWVVVFQ

FQHIMVGLILPGIVILSCYCIIISKLSHSKGHQKRKALKTTVILILAFFA

CWLPYYIGISIDSFILLEIIKQGCEFENTVHKWISITEALAFFHCCLNPI

LYAFLGAKFKTSAQHALTSVSRGSSLKILSKGKRGGHSSVSTESESSSFH

SS;
``` the chemokine (C-X-C motif) receptor 4 isoform a [*Homo sapiens*] having the sequence as depicted under the Genbank accession number NP_001008540 SEQ ID No. 28:

```
MSIPLPLLQIYTSDNYTEEMGSGDYDSMKEPCFREENANFNKIFLPTIYS

IIFLTGIVGNGLVILVMGYQKKLRSMTDKYRLHLSVADLLFVITLPFWAV

DAVANWYFGNFLCKAVHVIYTVNLYSSVLILAFISLDRYLAIVHATNSQR

PRKLLAEKVVYVGVWIPALLLTIPDFIFANVSEADDRYICDRFYPNDLWV

VVFQFQHIMVGLILPGIVILSCYCIIISKLSHSKGHQKRKALKTTVILIL

AFFACWLPYYIGISIDSFILLEIIKQGCEFENTVHKWISITEALAFFHCC

LNPILYAFLGAKFKTSAQHALTSVSRGSSLKILSKGKRGGHSSVSTESES

SSFHSS;
``` an alternate transcriptional splice variant or a natural variant thereof having at least 95% identity with one of these b or a isoforms having the SEQ ID No. 27 or 28; and
a fragment thereof capable of being specifically recognizing by its natural ligand stromal cell-derived factor-1 (SDF-1) and having preferably at least 100, 150 and 200 amino acid length.

CXCR2 is selected from the group consisting of:
the interleukin 8 receptor beta [*Homo sapiens*] having the sequence as depicted under the Genbank accession number NP_001548 SEQ ID No. 29:

MEDFNMESDSFEDFWKGEDLSNYSYSSTLPPFLLDAAPCEPESLEINKYF

VVIIYALVFLLSLLGNSLVMLVILYSRVGRSVTDVYLLNLALADLLFALT

LPIWAASKVNGWIFGTFLCKVVSLLKEVNFYSGILLLACISVDRYLAIVH

ATRTLTQKRYLVKFICLSIWGLSLLLALPVLLFRRTVYSSNVSPACYEDM

GNNTANWRMLLRILPQSFGFIVPLLIMLFCYGFTLRTLFKAHMGQKHRAM

RVIFAVVLIFLLCWLPYNLVLLADTLMRTQVIQETCERRNHIDRALDATE

ILGILHSCLNPLIYAFIGQKFRHGLLKILAIHGLISKDSLPKDSRPSFVG

SSSGHTSTTL;

an alternate transcriptional splice variant or a natural variant thereof having at least 95% identity with this interleukin 8 receptor beta having the SEQ ID No. 29; and
a fragment thereof capable of being specifically recognizing by IL-8 and having preferably at least 100, 150 and 200 amino acid length.

The invention also comprises a method for selecting a compound having an anti-HIV activity or which can be used for the preparation of a composition for the treatment of HIV infection, characterized in that said method comprises the step of:

In a first aspect, a subject of the present invention is a process for the generation and the selection of antibodies according to the invention.

More particularly, the invention concerns a process for the selection of an anti CXCR4 antibody, or one of its functional fragments or derivatives, capable to inhibit HIV replication comprising the following steps:
i) screening the generated antibodies and selecting antibodies capable to bind specifically to CXCR4;
ii) testing the selected antibodies of step i) and selecting antibodies capable to bind peripheral blood mononuclear cells (PBMC),
iii) testing the selected antibodies of step ii) and selecting antibodies capable to bind to CXCR4 homodimer, and then
iv) testing the selected antibodies of step iii) and selecting antibodies capable to inhibit primary isolates X4-tropic HIV-1 replication in PBMC.

In another embodiment, the invention concerns a process for the selection of an anti CXCR4 antibody, or one of its functional fragments or derivatives, capable to inhibit HIV replication comprising the following steps:
i) screening the generated antibodies and selecting antibodies capable to bind specifically to CXCR4;
ii) testing the selected antibodies of step i) and selecting antibodies capable to bind peripheral blood mononuclear cells (PBMC),
iii) testing the selected antibodies of step ii) and selecting antibodies capable to bind to CXCR4 homodimer, and then
iv) testing the selected antibodies of step iii) and selecting antibodies capable to inhibit primary isolates X4-tropic HIV-1 replication in PBMC and/or capable to inhibit primary isolates X4/R5-tropic HIV-1 replication in PBMC.

The generation of the antibodies can be realized by any method known by the man skilled in the art, such as for example, fusion of a myeloma cell with spleen cells from immunized mice or other species compatible with the selected myeloma cells [Kohler & Milstein, 1975, Nature, 256:495-497]. The immunized animals could include transgenic mice with human immunoglobulin loci which then directly produce human antibodies. Another possible embodiment could consist in using phage display technologies to screen libraries.

The screening steps i) and ii) can be realized by any method or process known by the man skilled in the art. As non limitative examples, can be mentioned ELISA, BIAcore, immunohistochemistry, western blot analysis using CXCR4 expressing cell membrane extracts or purified CXCR4, FACS analysis and functional screens. A preferred process consists in a screen by FACS analysis on CXCR4 transfectant (step 1) and on at least PBMC (step 2) to be sure that the produced antibodies will be able to also recognize the native CXCR4 receptor conformation at the target cell surface. This process will be described more precisely in the following examples.

The screening step iii) can be realized by any method or process known by the man skilled in the art. As non limiting but preferred example, can be mentioned western blotting and/or immuno-precipitation techniques using antibodies of interest on membrane extract from CXCR4 transfected cells or PBMC.

The screening step iv) can be realized by any method or process known by the man skilled in the art. As non limitative but preferred example, can be mentioned a process consisting in screening antibodies for their ability to inhibit X4 primary HIV-1 and/or X4/R5 primary HIV-1 isolates replication in PBMC by using a protocol described by Holl et al. (J. Immunol. 2004, 173, 6274-83).

In a preferred embodiment of the step iii) of selection of the process of the invention, said step iii) consists in evaluating antibodies by BRET analysis on cells expressing CXCR4-RLuc/CXCR4-YFP and selecting antibodies capable to inhibit at least 40%, preferably 45%, 50%, 55% and most preferably 60% of the BRET signal.

The BRET technology is a technology known as being representative of the protein dimerization [Angers et al., PNAS, 2000, 97:3684-89].

The BRET technology, used in the step iii) of the process, is well known by the man skilled in the art and will be detailed in the following examples. More particularly, BRET (Bioluminescence Resonance Energy Transfer) is a non-radiative energy transfer occurring between a bioluminescent donor (*Renilla* Luciferase (Rluc)) and a fluorescent acceptor, a mutant of GFP (Green Fluorescent Protein) or YFP (Yellow fluorescent protein). In the present case EYFP (Enhanced Yellow Fluorescent Protein) was used. The efficacy of transfer depends on the orientation and the distance between the donor and the acceptor. Then, the energy transfer can occur only if the two molecules are in close proximity (1-10 nm). This property is used to generate protein-protein interaction assays. Indeed, in order to study the interaction between two partners, the first one is genetically fused to the *Renilla* Luciferase and the second one to the yellow mutant of the GFP. Fusion proteins are generally, but not obligatory, expressed in mammalian cells. In presence of its membrane permeable substrate (coelenterazine), Rluc emits blue light. If the GFP mutant is closer than 10 nm from the Rluc, an energy transfer can occur and an additional yellow signal can be detected. The BRET signal is measured as the ratio between the light emitted by the acceptor and the light emitted by the donor. So the BRET signal will increase as the two fusion proteins are brought into proximity or if a conformational change brings Rluc and GFP mutant closer.

If the BRET analysis consists in a preferred embodiment, any method known by the man skilled in the art can be used to measure CXCR4 dimers conformational changes. Without limitation, the following technologies can be mentioned: FRET (Fluorescence Resonance Energy Transfer), HTRF (Homogenous Time resolved Fluorescence), FLIM (Fluorescence Lifetime Imaging Microscopy) or SW-FCCS single wavelength fluorescence cross-correlation spectroscopy).

Other classical technologies could also be used, such as Co-immunoprecipitation, Alpha screen, Chemical cross-linking, Double-Hybrid, Affinity Chromatography, ELISA or Far western blot.

In a particular aspect of the process according to the invention, step iii) consists in evaluating antibodies by BRET analysis on cells expressing both CXCR4-RLuc/CXCR4-YFP and selecting antibodies capable to inhibit at least 40%, of the BRET signal.

In a second aspect, a subject of the invention is isolated antibodies, or one of their functional fragments or derivatives, being obtained by said process. Said antibodies or one of their said fragments or derivatives, are capable of binding specifically to the human CXCR4, said antibodies being also capable to induce CXCR4 homodimers conformational changes.

It is known from literature that CXCR4 Mabs like, for example clone A120, are able to inhibit HIV-1 laboratory strain (X4HIV-1$_{NL4-3}$) entry into PBMC (Tanaka R. et al, J. Virol. 2001, 75, 11534-11543). Furthermore, it is also known that CXCR4 Mabs are able to inhibit HIV-1 X4 primary isolates into cell lines expressing CXCR4. On the contrary, it has never been disclosed antibody able to inhibit such virus in their natural environment, i.e. not only on laboratory viruses or cell lines. Nevertheless, it is a novel and not obvious aspect of the invention that CXCR4 Mabs are able to inhibit HIV-1 X4 primary isolates into PBMC.

The expressions "functional fragments and derivatives" and "antigen binding fragments and derivatives" are similar and will be defined in details later in the present specification.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

More particularly, according to another aspect of the invention, it is claimed isolated antibodies, or one of their functional fragments or derivatives, said antibodies being characterized in that they comprise at least one complementary determining region CDR chosen from CDRs comprising the amino acid sequence SEQ ID Nos. 1 to 6 and 30 to 33 as defined by the IMGT numbering system.

According to a first aspect, the invention relates to an isolated antibody, or a functional fragment or derivative of same, comprising at least one CDR chosen among the CDRs of sequences SEQ ID Nos. 1 to 6, as defined according to the IMGT numbering system, or at least one CDR whose sequence has at least 80%, preferably 85%, 90%, 95% and 98% identity after optimal alignment with sequences SEQ ID Nos. 1 to 6.

According to a second aspect, the invention relates to an isolated antibody, or a functional fragment or derivative of same, comprising at least one CDR chosen among the CDRs of sequences SEQ ID Nos. 1, 2 and 30 to 33, as defined according to the IMGT numbering system, or at least one CDR whose sequence has at least 80%, preferably 85%, 90%, 95% and 98% identity after optimal alignment with sequences SEQ ID Nos. 1, 2 and 30 to 33.

A "functional fragment" or "antigen binding fragment" of an antibody means in particular an antibody fragment, such as fragments Fv, scFv (sc=single chain), Fab, F(ab')$_2$, Fab', scFv-Fc or diabodies, or any fragment whose half-life has been increased. Such functional fragments will be described in detail later in the present description.

A "derived compound" or "derivative" of an antibody means in particular a binding protein composed of a peptide scaffold and at least one of the CDRs of the original antibody in order to preserve its ability to recognize CXCR4. Such derived compounds, well-known to a person skilled in the art, will be described in more detail later in the present description.

More preferably, the invention comprises the antibodies, their derived compounds or their functional fragments, according to the present invention, notably chimeric or humanized, obtained by genetic recombination or chemical synthesis.

According to a preferred embodiment, the antibody according to the invention, or its derived compounds or functional fragments, is characterized in that it consists of a monoclonal antibody.

"Monoclonal antibody" is understood to mean an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

More particularly, according to a first preferred embodiment of the invention, the antibody, or its derived compounds or functional fragments, is characterized in that it comprises a light chain comprising at least one CDR chosen from CDR-L1, CDR-L2 and CDR-L3, wherein:

CDR-L1 comprises the amino acid sequence SEQ ID No. 1,

CDR-L2 comprises the amino acid sequence SEQ ID No. 2,

CDR-L3 comprises the amino acid sequence SEQ ID No. 3.

According to another embodiment, the antibodies of the invention, or one of their derived compounds or functional fragments, are characterized in that they comprise a light chain comprising at least one of the three CDRs of the sequences SEQ ID Nos.1, 2 or 3, or at least one sequence with at least 80%, preferably 85%, 90%, 95% and 98% identity after optimal alignment with sequences SEQ ID Nos.1, 2 or 3.

The antibody of the invention, or one of its functional fragments or derivatives, is also characterized in that it comprises a light chain comprising CDR-L1, CDR-L2 and CDR- L3, wherein CDR-L1 comprises the amino acid sequence SEQ ID No. 1, CDR-L2 comprises the amino acid sequence SEQ ID No. 2 and CDR-L3 comprises the amino acid sequence SEQ ID No. 3.

In another embodiment, the antibody of the invention, or one of its functional fragments or derivatives, is characterized in that it comprises a light chain of sequence comprising the amino acid sequence SEQ ID No. 7, or at least one sequence with at least 80%, preferably 85%, 90%, 95% and 98% identity after optimal alignment with sequences SEQ ID No. 7.

According to a second preferred embodiment of the invention, the antibody, or its derived compounds or functional fragments, is characterized in that it comprises a light chain comprising at least one CDR chosen from CDR-L1, CDR-L2 and CDR-L3, wherein:
  CDR-L1 comprises the amino acid sequence SEQ ID No. 1,
  CDR-L2 comprises the amino acid sequence SEQ ID No. 2,
  CDR-L3 comprises the amino acid sequence SEQ ID No. 30.

According to another embodiment, the antibodies of the invention, or one of their derived compounds or functional fragments, are characterized in that they comprise a light chain comprising at least one of the three CDRs of the sequences SEQ ID Nos.1, 2 or 30, or at least one sequence with at least 80%, preferably 85%, 90%, 95% and 98% identity after optimal alignment with sequences SEQ ID Nos.1, 2 or 30.

The antibody of the invention, or one of its functional fragments or derivatives, is also characterized in that it comprises a light chain comprising CDR-L1, CDR-L2 and CDR-L3, wherein CDR-L1 comprises the amino acid sequence SEQ ID No. 1, CDR-L2 comprises the amino acid sequence SEQ ID No. 2 and CDR-L3 comprises the amino acid sequence SEQ ID No. 30.

In another embodiment, the antibody of the invention, or one of its functional fragments or derivatives, is characterized in that it comprises a light chain of sequence comprising the amino acid sequence SEQ ID No. 34, or at least one sequence with at least 80%, preferably 85%, 90%, 95% and 98% identity after optimal alignment with sequences SEQ ID No. 34.

More particularly, the antibodies of the invention, or one of their derived compounds or functional fragments, are characterized in that they comprise a heavy chain comprising at least one CDR chosen from CDR-H1, CDR-H2 and CDR-H3, wherein:
  CDR-H1 comprises the amino acid sequence SEQ ID No. 4,
  CDR-H2 comprises the amino acid sequence SEQ ID No. 5,
  CDR-H3 comprises the amino acid sequence SEQ ID No. 6.

According to another embodiment, the antibodies of the invention, or one of their derived compounds or functional fragments, are characterized in that they comprise a heavy chain comprising at least one of the three CDRs of the sequences SEQ ID Nos. 4, 5 or 6, or at least one sequence with at least 80%, preferably 85%, 90%, 95% and 98% identity after optimal alignment with sequences SEQ ID Nos. 4, 5 or 6.

According to another particular embodiment, antibodies, or one of their derived compounds or functional fragments, are characterized in that they comprise a heavy chain comprising CDR-H1, CDR-H2 and CDR-H3, wherein CDR-H1 comprises the amino acid sequence SEQ ID No. 4, CDR-H2 comprises the amino acid sequence SEQ ID No. 5 and the CDR-H3 comprises the amino acid sequence SEQ ID No. 6.

In another embodiment, the antibody of the invention, or one of its functional fragments or derivatives, is characterized in that it comprises a heavy chain of sequence comprising the amino acid sequence SEQ ID No. 8, or at least one sequence with at least 80%, preferably 85%, 90%, 95% and 98% identity after optimal alignment with sequences SEQ ID No. 8.

More particularly, the antibodies of the invention, or one of their derived compounds or functional fragments, are characterized in that they comprise a heavy chain comprising at least one CDR chosen from CDR-H1, CDR-H2 and CDR-H3, wherein:
  CDR-H1 comprises the amino acid sequence SEQ ID No. 31,
  CDR-H2 comprises the amino acid sequence SEQ ID No. 32,
  CDR-H3 comprises the amino acid sequence SEQ ID No. 33.

According to another embodiment, the antibodies of the invention, or one of their derived compounds or functional fragments, are characterized in that they comprise a heavy chain comprising at least one of the three CDRs of the sequences SEQ ID Nos. 31, 32 or 33, or at least one sequence with at least 80%, preferably 85%, 90%, 95% and 98% identity after optimal alignment with sequences SEQ ID Nos. 31, 32 or 33.

According to another particular embodiment, antibodies, or one of their derived compounds or functional fragments, are characterized in that they comprise a heavy chain comprising CDR-H1, CDR-H2 and CDR-H3, wherein CDR-H1 comprises the amino acid sequence SEQ ID No. 31, CDR-H2 comprises the amino acid sequence SEQ ID No. 32 and the CDR-H3 comprises the amino acid sequence SEQ ID No. 33.

In another embodiment, the antibody of the invention, or one of its functional fragments or derivatives, is characterized in that it comprises a heavy chain of sequence comprising the amino acid sequence SEQ ID No. 35, or at least one sequence with at least 80%, preferably 85%, 90%, 95% and 98% identity after optimal alignment with sequences SEQ ID No. 35.

The antibody of the invention, or one of its functional fragments or derivatives, is characterized in that it comprises a light chain comprising CDR-L1, CDR-L2 and CDR-L3 comprising respectively the amino acid sequence SEQ ID Nos. 1, 2 and 3; and a heavy chain comprising CDR-H1, CDR-H2 and CDR-H3 comprising respectively the amino acid sequence SEQ ID Nos. 4, 5 and 6.

At last, the antibody of the invention, or one of its functional fragments or derivatives, can also be characterized in that it comprises a light chain comprising the amino acid sequence SEQ ID No. 7 and a heavy chain comprising the amino acid sequence SEQ ID No. 8.

The antibody of the invention, or one of its functional fragments or derivatives, is characterized in that it comprises a light chain comprising CDR-L1, CDR-L2 and CDR-L3 comprising respectively the amino acid sequence SEQ ID Nos. 1, 2 and 30; and a heavy chain comprising CDR-H1, CDR-H2 and CDR-H3 comprising respectively the amino acid sequence SEQ ID Nos. 31, 32 and 33.

At last, the antibody of the invention, or one of its functional fragments or derivatives, can also be characterized in that it comprises a light chain comprising the amino acid sequence SEQ ID No. 34 and a heavy chain comprising the amino acid sequence SEQ ID No. 35.

In the present description, the terms "polypeptides", "polypeptide sequences", "peptides" and "proteins attached to antibody compounds or to their sequences" are interchangeable.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

In a first embodiment, complementarity-determining region, or CDR, means the hypervariable regions of the heavy and light chains of immunoglobulins as defined by Kabat et al. (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

In a second embodiment, by CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

For more clarity, it must be understood that in the following description, and more particularly in tables 2 and 3, the CDRs will be defined by IMGT numbering system and by Kabat numbering system.

IMGT numbering system defines the CDRs according to the IMGT system as above defined whereas Kabat numbering system defines the CDRs according to the Kabat system as above defined.

More particularly, concerning the antibody referred as 515H7, CDR-L1 consists of SEQ ID No. 1 in the IMGT numbering systems and of SEQ ID No. 9 in the Kabat numbering system. Concerning the CDR-L2, it consists of SEQ ID No. 2 in the IMGT numbering systems and of SEQ ID No. 10 in the Kabat numbering system. The CDR-L3 consists of SEQ ID No. 3 for each of the two numbering systems. For the heavy chain, the CDR-H1 consists of the SEQ ID No. 4 in the IMGT numbering system and of SEQ ID No. 11 in the kabat numbering system. The CDR-H2 consists of SEQ ID No. 5 in the IMGT numbering systems and of SEQ ID No. 12 in the kabat numbering system. At last, the CDR-H3 consists in the SEQ ID No. 6 in the IMGT numbering systems whereas it consists of SEQ ID No. 13 in the kabat numbering system.

Then, concerning the antibody referred as 301aE5, CDR-L1 consists of SEQ ID No. 1 in the IMGT numbering systems and of SEQ ID No. 9 in the Kabat numbering system. Concerning the CDR-L2, it consists of SEQ ID No. 2 in the IMGT numbering systems and of SEQ ID No. 36 in the Kabat numbering system. The CDR-L3 consists of SEQ ID No. 30 in the IMGT numbering systems and of SEQ ID No. 37 in the Kabat numbering system. For the heavy chain, the CDR-H1 consists of the SEQ ID No. 31 in the IMGT numbering system and of SEQ ID No. 38 in the Kabat numbering system.

The CDR-H2 consists of SEQ ID No. 32 in the IMGT numbering systems and of SEQ ID No. 39 in the Kabat numbering system. At last, the CDR-H3 consists in the SEQ ID No. 33 in the IMGT numbering systems whereas it consists of SEQ ID No. 40 in the Kabat numbering system.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250), can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

In a specific embodiment, the present invention relates to murine antibodies, or derived compounds or functional fragments of same.

As seen above, the invention also relates to any compound derived from antibodies as described in the invention.

More particularly, an antibody of the invention, or its derived compounds or functional fragments, is characterized in that said derived compound consists of a binding protein comprising a peptide scaffold on which is grafted at least one CDR in such a way as to preserve all or part of the paratope recognition properties of the initial antibody.

One or more sequences among the CDR sequences described in the present invention can also be present on the various immunoglobulin protein scaffolding. In this case, the protein sequence makes it possible to recreate a peptide skeleton favorable to the folding of the grafted CDRs, enabling them to preserve their paratope antigen-recognition properties.

Generally, a person skilled in the art knows how to determine the type of protein scaffold on which to graft at least one of the CDRs arising from the original antibody. More particularly, it is known that to be selected such scaffolds must meet the greatest number of criteria as follows (Skerra A., J. Mol. Recogn., 2000, 13:167-187):

good phylogenetic conservation;
known three-dimensional structure (as, for example, by crystallography, NMR spectroscopy or any other technique known to a person skilled in the art);
small size;
few or no post-transcriptional modifications; and/or
easy to produce, express and purify.

The origin of such protein scaffolds can be, but is not limited to, the structures selected among: fibronectin and preferentially fibronectin type III domain 10, lipocalin, anticalin (Skerra A., J. Biotechnol., 2001, 74(4):257-75), protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat".

Scaffolds derived from toxins such as, for example, toxins from scorpions, insects, plants, mollusks, etc., and the protein inhibitors of neuronal NO synthase (PIN) should also be mentioned.

An example, in no way limiting, of such hybrid constructions, is the insertion of the CDR-H1 (heavy chain) of an anti-CD4 antibody, namely 13B8.2, in one of the loops in the PIN, the new binding protein thus obtained preserving the same binding properties as the original antibody (Bes et al., Biochem. Biophys. Res. Commun., 2006, 343(1), 334-344). On a purely illustrative basis, grafting the CDR-H3 (heavy chain) of an anti-lysozyme VHH antibody on one of the loops of neocarzinostatin (Nicaise et al., Protein Science, 2004, 13(7):1882-1891) can also be mentioned.

Lastly, as described above, such peptide scaffolds can comprise at least one of the CDRs arising from the original antibody. Preferably, but not being a requirement, a person skilled in the art will select at least one CDR from the heavy chain, the latter being known to be primarily responsible for the specificity of the antibody. The selection of one or more relevant CDRs is obvious to a person skilled in the art, who will then choose suitable known techniques (Bes et al., FEBS letters 508, 2001, 67-74).

A specific aspect of the present invention relates to a method for selecting a compound derived from an antibody according to the invention, said derived compound being capable of inhibiting in vitro and/or in vivo HIV cell entry and said derived compound comprising a peptide scaffold on which is grafted at least one antibody CDR, characterized in that it comprises the following steps:

a) the placing in contact in vitro of a compound composed of a peptide scaffold on which is grafted at least one antibody CDR with a biological sample containing HIV type 1 and PBMC; and b) the selection of said compound if said compound is capable of inhibiting the HIV-1 replication, and characterized in that said at least one grafted CDR is selected among the following CDRs of sequence SEQ ID No. 1 to 6 and 30 to 33 or a sequence with at least 80%, preferably 85%, 90%, 95% and 98% identity after optimal alignment with sequence SEQ ID Nos. 1 to 6 and 30 to 33.

According to a preferred mode, the method can include in step a) the placing in contact in vitro of a compound comprising a peptide scaffold on which is grafted at least two or three antibody CDRs.

According to an even more preferred mode of this method, the peptide scaffold is selected among the scaffolds or binding proteins whose structures were mentioned above.

Obviously, these examples are in no way limiting, and any other structure known or obvious to a person skilled in the art should be considered as being covered by the protection conferred by the present patent application.

The present invention thus relates to an antibody, or its derived compounds or functional fragments, characterized in that the peptide scaffold is selected among proteins that are a) phylogenetically well preserved, b) of robust architecture, c) with a well-known 3-D molecular organization, d) of small size and/or e) comprising regions that can be modified by deletion and/or insertion without modifying stability properties.

According to a preferred embodiment, the antibody of the invention, or its derived compounds or functional fragments, is characterized in that said peptide scaffold is selected among i) scaffolds arising from fibronectin, preferentially fibronectin type 3 domain 10, lipocalin, anticalin, protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat" or iii) protein inhibitors of neuronal NO synthase (PIN).

Another aspect of the invention relates to the functional fragments of the antibody described above.

More particularly, the invention targets an antibody, or its derived compounds or functional fragments, characterized in that said functional fragment is selected among the fragments Fv, Fab, (Fab')$_2$, Fab', scFv, scFv-Fc and diabodies, or any fragment whose half-life has been increased such as PEGylated fragments.

Such functional fragments of the antibody according to the invention consist, for example, of the fragments Fv, scFv (sc=single chain), Fab, F(ab')$_2$, Fab', scFv-Fc or diabodies, or any fragment whose half-life has been increased by chemical modification, such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or PLGA, said fragments possessing at least one of the characteristic CDRs of the invention which is notably capable of exerting in a general manner activity, even partial, of the antibody from which it arises.

Preferably, said functional fragments will comprise or include a partial sequence of the variable heavy or light chain of the antibody from which they are derived, said partial sequence being sufficient to retain the same binding specificity as the antibody from which it arises and sufficient affinity, preferably at least equal to 1/100, more preferably at least 1/10 of that of the antibody from which it arises.

Such a functional fragment will contain at least five amino acids, preferably 6, 7, 8, 10, 15, 25, 50 or 100 consecutive amino acids of the sequence of the antibody from which it arises.

Preferably, these functional fragments will be of the types Fv, scFv, Fab, F(ab')$_2$, F(ab'), scFv-Fc or diabodies, which generally have the same binding specificity as the antibody from which they result. According to the present invention, fragments of the antibody of the invention can be obtained from the antibodies described above by methods such as enzyme digestion, including pepsin or papain, and/or by cleavage of the disulfide bridges by chemical reduction. The antibody fragments can be also obtained by recombinant genetics techniques also known to a person skilled in the art or by peptide synthesis by means, for example, of automatic peptide synthesizers such as those sold by Applied BioSystems, etc.

For more clarity, table 2 below summarizes the various amino acid sequences corresponding to the antibodies of the invention.

TABLE 2

(wherein Mu. = murine)

| Antibody | CDR numbering | Heavy chain | Light chain | SEQ ID NO. |
|---|---|---|---|---|
| 515H7 | IMGT | | CDR-L1 | 1 |
| | | | CDR-L2 | 2 |
| | | | CDR-L3 | 3 |
| | | CDR-H1 | | 4 |
| | | CDR-H2 | | 5 |
| | | CDR-H3 | | 6 |
| | Kabat | | CDR-L1 | 9 |
| | | | CDR-L2 | 10 |
| | | | CDR-L3 | 3 |
| | | CDR-H1 | | 11 |
| | | CDR-H2 | | 12 |
| | | CDR-H3 | | 13 |
| | | | Mu. variable domain | 7 |
| | | Mu. variable domain | | 8 |
| 301aE5 | IMGT | | CDR-L1 | 1 |
| | | | CDR-L2 | 2 |
| | | | CDR-L3 | 30 |
| | | CDR-H1 | | 31 |
| | | CDR-H2 | | 32 |
| | | CDR-H3 | | 33 |
| | Kabat | | CDR-L1 | 9 |
| | | | CDR-L2 | 36 |
| | | | CDR-L3 | 37 |
| | | CDR-H1 | | 38 |
| | | CDR-H2 | | 39 |
| | | CDR-H3 | | 40 |
| | | | Mu. variable domain | 34 |
| | | Mu. variable domain | | 35 |

A particular important additional aspect of the antibodies object of the present invention is that they do not exhibit effector functions, such as antibody-dependent cellular cytotoxicity (ADCC) and/or complement-dependant cytotoxicity (CDC).

More particularly, as an example, the antibodies of the invention, or one of their functional fragments or derivatives, have no affinity for the FcγR (I, II or III) or for the C1q, or for both of them.

Structurally, this means for the man skilled in the art that the antibodies of the invention, or one of their functional fragments or derivatives, are devoid of Fc portion or their Fc portion does not present a correct glycosylation able to confer effector functions.

Consequence of this is that the antibodies of the invention are preferably selected form IgG4 or IgG2 isotypes, most preferably IgG4.

Similarly, preferred fragments are fragments devoid of ADCC such as Fv, scFv (sc for single chain), Fab, F(ab')$_2$, Fab', scFv-Fc fragments or diabodies, or any fragment of which the half-life time would have been increased by chemical modification, such as the addition of poly(alkylene)glycol such as poly(ethylene)glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome.

More particularly, a preferred functional fragment of the invention derived from the antibody 515H7 is a scFv, hereinafter referred as 515H7 scFv-Ck fragment, comprises the amino acid sequence SEQ ID No. 54

The nucleotide sequence corresponding to said scFv comprises the sequence SEQ ID No. 55.

Another specific aspect of the present invention relates to chimeric antibodies, or their derived compounds or functional fragments, characterized in that said antibodies also comprise light-chain and heavy-chain constant regions derived from an antibody of a species heterologous with the mouse, notably man.

Yet another specific aspect of the present invention relates to humanized antibodies, or their derived compounds or functional fragments, characterized in that the constant regions of the light-chain and the heavy-chain derived from human antibody are, respectively, the lambda or kappa region and the gamma-2 or preferably gamma-4 region.

The antibody of the invention also comprises chimeric or humanized antibodies.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. Refer to Verhoeyn et al. (BioEssays, 8:74, 1988) for methods for preparing chimeric antibodies.

The table 3 herein-under summarizes the amino acids sequences of the various heavy and light chains of the chimeric antibody 515H7 (referred as c515H7 or C515H7) according to the invention.

TABLE 3

(wherein c = chimeric)

| Antibody c515H7 | Heavy chain | Light chain | SEQ ID NO. |
|---|---|---|---|
| Complete | cVH (G4wt) | — | 56 |
| Sequences | cVH (G4PRO) | — | 57 |
| (without signal | cVH (G2 wt) | — | 58 |
| peptide) | — | cVL-Ck | 59 |

The nucleotide sequence corresponding to said Antibody c515H7 heavy chains SEQ ID Nos. 56 to 58 and light chain SEQ ID No. 59 correspond respectively to the sequence SEQ ID Nos. 60 to 63 (heavy chains) and SEQ ID No. 64 (light chain).

In a preferred embodiment, the heavy chain sequences are deleted from their C-terminal lysine residue (as found in the original pConPlus vector series from Lonza: pConPlusγ4ΔK, pConPlusγ4PROΔK & pConPlusγ2ΔK).

Moreover, the G4PRO heavy chain corresponds to a human IgG4 isotype carrying a mutation in the Hinge region to avoid formation of half-antibodies. This mutation is found in the parental pConPlusγ4PROΔK from Lonza [Angal S, King D J, Bodmer M W, Turner A, Lawson A D, Roberts G, Pedley B, Adair J R. A single amino acid substitution abolishes the heterogeneity of chimeric mouse/human (IgG4) antibody. Mol Immunol. (1993);30(1):105-108].

More particularly, the invention relates to a chimeric antibody heavy chain characterized in that it comprises CDRs homologous to corresponding CDRs of an antibody derived from a different mammalian species, wherein said CDRs, according to IMGT, consist of CDR-H1, CDR-H2 and CDR-H3 comprising respectively the sequences SEQ ID Nos. 4, 5 and 6.

More particularly, the invention relates to a chimeric antibody light chain characterized in that it comprises CDRs homologous to corresponding CDRs of an antibody derived from a different mammalian species, wherein said CDRs, according to IMGT, consist of CDR-L1, CDR-L2 and CDR-L3 comprising respectively the sequences SEQ ID Nos. 1, 2 and 3.

More particularly, the invention relates to a chimeric antibody, or a derived compound or functional fragment of same, characterized in that it comprises heavy and light chains each having CDRs homologous to corresponding CDRs of an antibody derived from a different mammalian species, wherein said CDRs, according to IMGT, consist of CDR-H1, CDR-H2 and CDR-H3 of the heavy chain comprising respectively the sequences SEQ ID Nos. 4, 5 and 6, and CDR-L1, CDR-L2 and CDR-L3 of the light chain comprising respectively the sequences SEQ ID Nos. 1, 2 and 3.

In another embodiment, the invention relates to a chimeric antibody, or a derived compound or functional fragment of same, comprising a heavy chain variable region of sequence consisting of SEQ ID No. 8, and a light chain variable region of sequence SEQ ID No. 7.

In still another embodiment, the invention relates to a chimeric antibody, or a derived compound or functional fragment of same, comprising a heavy chain of sequence selected from the group consisting of SEQ ID Nos. 56, 57 or 58, and a light chain of sequence SEQ ID No. 59.

In a preferred embodiment, the chimeric antibody c515H7 VH(G4wt)/VL-Ck, or a derived compound or functional fragment of same, according to the invention comprises a heavy chain variable region of sequence SEQ ID No. 56, and a light chain variable region of sequence SEQ ID No. 59.

In a preferred embodiment, the chimeric antibody c515H7 VH(G4PRO)/VL-Ck, or a derived compound or functional fragment of same, according to the invention comprises a heavy chain variable region of sequence SEQ ID No. 57, and a light chain variable region of sequence SEQ ID No. 59.

In a preferred embodiment, the chimeric antibody c515H7 VH(G2wt)/VL-Ck, or a derived compound or functional fragment of same, according to the invention comprises a heavy chain variable region of sequence SEQ ID No. 58, and a light chain variable region of sequence SEQ ID No. 59.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988).

The humanized antibodies of the invention or fragments of same can be prepared by techniques known to a person skilled in the art (such as, for example, those described in the documents Singer et al., J. Immun , 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566 647 or U.S. Pat. Nos. 5,530,101, 6,180,370, 5,585,089 and 5,693,761. 5,639,641 or 6,054,297, 5,886,152 and 5,877,293 can also be cited.

In addition, the invention also relates to humanized antibodies arising from the murine antibody described above.

In a preferred manner, constant regions of the light-chain and the heavy-chain derived from human antibody are, respectively, the lambda or kappa and the gamma-2 or preferably gamma-4 region.

More particularly, the invention relates to a humanized antibody heavy chain characterized in that it comprises i) a framework region homologous to corresponding framework region of a human antibody heavy chain, and ii) CDRs homologous to corresponding CDRs of an antibody derived from a different mammalian species, wherein said CDRs, according to IMGT, consist of CDR-H1, CDR-H2 and CDR-H3 comprising respectively the sequences SEQ ID Nos. 4, 5 and 6.

In another embodiment, the invention relates to a humanized antibody heavy chain comprising a variable region of sequence consisting of SEQ ID No. 64.

In still another embodiment, the invention relates to a humanized antibody heavy chain comprising the complete sequence selected from the group consisting of SEQ ID Nos. 67, 68 and 69.

More particularly, the invention relates to a humanized antibody light chain characterized in that it comprises i) a framework region homologous to corresponding framework region of a human antibody light chain, and ii) CDRs homologous to corresponding CDRs of an antibody derived from a different mammalian species, wherein said CDRs, according to IMGT, consist of CDR-L1, CDR-L2 and CDR-L3 comprising respectively the sequences SEQ ID Nos. 1, 2 and 3.

In another embodiment, the invention relates to a humanized antibody light chain comprising a variable region of sequence selected from the group consisting of SEQ ID Nos. 65, 66, 82 or 83.

In still another embodiment, the invention relates to a humanized antibody light chain comprising the complete sequence selected from the group consisting of SEQ ID Nos. 70, 71, 84 or 85.

More particularly, the invention relates to a humanized antibody, or a derived compound or functional fragment of same, characterized in that it comprises heavy and light chains each having i) framework regions homologous to corresponding framework regions of a human antibody, and ii) CDRs homologous to corresponding CDRs of an antibody derived from a different mammalian species, wherein said CDRs, according to IMGT, consist of CDR-H1, CDR-H2 and CDR-H3 of the heavy chain comprising respectively the sequences SEQ ID Nos. 4, 5 and 6, and CDR-L1, CDR-L2 and CDR-L3 of the light chain comprising respectively the sequences SEQ ID Nos. 1, 2 and 3.

In another embodiment, the invention relates to a humanized antibody, or a derived compound or functional fragment of same, comprising a heavy chain variable region of sequence consisting of SEQ ID No. 64, and a light chain variable region of sequence selected from the group consisting of SEQ ID Nos. 65, 66, 82 or 83.

In still another embodiment, the invention relates to a humanized antibody, or a derived compound or functional fragment of same, comprising a heavy chain of sequence selected from the group consisting of SEQ ID Nos. 67, 68 or 69, and a light chain of sequence selected from the group consisting of SEQ ID Nos. 70, 71, 84 or 85.

In a preferred embodiment, the humanized antibody Hz515H7 VH1 D76N (G4wt)/VL2-Ck, or a derived compound or functional fragment of same, according to the invention comprises a heavy chain of sequence SEQ ID No. 67, and a light chain of sequence SEQ ID No. 70.

In another preferred embodiment, the humanized antibody Hz515H7 VH1 D76N (G4PRO)/VL2-Ck, or a derived compound or functional fragment of same, according to the invention comprises a heavy chain of sequence SEQ ID No. 68, and a light chain of sequence SEQ ID No. 70.

In another preferred embodiment, the humanized antibody Hz515H7 VH1 D76N (G2wt)/VL2-Ck, or a derived compound or functional fragment of same, according to the invention comprises a heavy chain of sequence SEQ ID No. 69, and a light chain of sequence SEQ ID No. 70.

In another preferred embodiment, the humanized antibody Hz515H7 VH1 D76N (G4wt)/VL2.1-Ck, or a derived compound or functional fragment of same, according to the invention comprises a heavy chain of sequence SEQ ID No. 67, and a light chain of sequence SEQ ID No. 71.

In another preferred embodiment, the humanized antibody Hz515H7 VH1 D76N (G4PRO)/VL2.1-Ck, or a derived compound or functional fragment of same, according to the invention comprises a heavy chain of sequence SEQ ID No. 68, and a light chain of sequence SEQ ID No. 71.

In another preferred embodiment, the humanized antibody Hz515H7 VH1 D76N (G2wt)/VL2.1-Ck, or a derived compound or functional fragment of same, according to the invention comprises a heavy chain of sequence SEQ ID No. 69, and a light chain of sequence SEQ ID No. 71.

In another preferred embodiment, the humanized antibody Hz515H7 VH1 D76N (G4wt)/VL2.2-Ck, or a derived compound or functional fragment of same, according to the invention comprises a heavy chain of sequence SEQ ID No. 67, and a light chain of sequence SEQ ID No. 84.

In another preferred embodiment, the humanized antibody Hz515H7 VH1 D76N (G4PRO)/VL2.2-Ck, or a derived compound or functional fragment of same, according to the invention comprises a heavy chain of sequence SEQ ID No. 68, and a light chain of sequence SEQ ID No. 84.

In another preferred embodiment, the humanized antibody Hz515H7 VH1 D76N (G2wt)/VL2.2-Ck, or a derived compound or functional fragment of same, according to the invention comprises a heavy chain of sequence SEQ ID No. 69, and a light chain of sequence SEQ ID No. 84.

In another preferred embodiment, the humanized antibody Hz515H7 VH1 D76N (G4wt)/VL2.3-Ck, or a derived compound or functional fragment of same, according to the invention comprises a heavy chain of sequence SEQ ID No. 67, and a light chain of sequence SEQ ID No. 85.

In another preferred embodiment, the humanized antibody Hz515H7 VH1 D76N (G4PRO)/VL2.3-Ck, or a derived compound or functional fragment of same, according to the invention comprises a heavy chain of sequence SEQ ID No. 68, and a light chain of sequence SEQ ID No. 85.

In another preferred embodiment, the humanized antibody Hz515H7 VH1 D76N (G2wt)/VL2.3-Ck, or a derived compound or functional fragment of same, according to the invention comprises a heavy chain of sequence SEQ ID No. 69, and a light chain of sequence SEQ ID No. 85.

The table 4 herein-under summarizes the amino acids sequences of the various heavy and light chains variable domains and full length (or complete), respectively, of the humanized antibody 515H7 according to the invention.

TABLE 4

(wherin Hz = humanized)

| Antibody Hz515H7 | Heavy chain | Light chain | SEQ ID NO. |
|---|---|---|---|
| Variable Domains | VH1 D76N | — | 64 |
|  | — | VL2 | 65 |
|  | — | VL2.1 | 66 |
|  | — | VL2.2 | 82 |
|  | — | VL2.3 | 83 |
| Complete Sequences (without signal peptide) | VH1 D76N (G4wt) | — | 67 |
|  | VH1 D76N (G4PRO) | — | 68 |
|  | VH1 D76N (G2 wt) | — | 69 |
|  | — | VL2-Ck | 70 |
|  | — | VL2.1-Ck | 71 |
|  | — | VL2.2-Ck | 84 |
|  | — | VL2.3-Ck | 85 |

In a preferred embodiment, the heavy chain sequences are deleted from their C-terminal lysine residue (as found in the original pConPlus vector series from Lonza: pConPlusγ4ΔK, pConPlusγ4PROΔK & pConPlusγ2ΔK).

Moreover, the G4PRO heavy chain corresponds to a human IgG4 isotype carrying a mutation in the Hinge region to avoid formation of half-antibodies. This mutation is found in the parental pConPlusγ4PROΔK from Lonza [Angal S, King D J, Bodmer M W, Turner A, Lawson A D, Roberts G, Pedley B, Adair J R. A single amino acid substitution abolishes the heterogeneity of chimeric mouse/human (IgG4) antibody. *Mol Immunol.* (1993);30(1):105-108].

As an example, for the avoidance of doubt, the expression "VH1" is similar to the expressions "VH Variant 1", "VH variant 1", "VH Var 1" or "VH var 1").

It must be understood that the above exemplified VH/VL combinations are not limitative. The man skilled in the art could of course, without undue burden and without applying inventive skill, rearrange all the VH and VL disclosed in the present specification.

A novel aspect of the present invention relates to an isolated nucleic acid characterized in that it is selected among the following nucleic acids (including any degenerate genetic code):

a) a nucleic acid, DNA or RNA, coding for an antibody, or one of its functional fragments or derivatives, according to the invention;

b) a nucleic acid comprising a DNA sequence selecting from the group of sequences consisting of SEQ ID Nos. 14 to 19 and 41 to 45;

c) a nucleic acid comprising a DNA sequence selecting from the group of sequences consisting of SEQ ID Nos. 20, 21, 46 and 47;

d) the corresponding RNA nucleic acids of the nucleic acids as defined in b) or c);

e) the complementary nucleic acids of the nucleic acids as defined in a), b) and c); and f) a nucleic acid of at least 18 nucleotides capable of hybridizing under conditions of high stringency with at least one of the CDRs of sequence SEQ ID Nos. 14 to 19 and 41 to 45.

Table 5 below summarizes the various nucleotide sequences concerning the antibodies of the invention.

TABLE 5

(wherein Mu. = murine)

| Antibody | CDR numbering | Heavy chain | Light chain | SEQ ID NO. |
|---|---|---|---|---|
| 515H7 | IMGT |  | CDR-L1 | 14 |
|  |  |  | CDR-L2 | 15 |
|  |  |  | CDR-L3 | 16 |
|  |  | CDR-H1 |  | 17 |
|  |  | CDR-H2 |  | 18 |
|  |  | CDR-H3 |  | 19 |
|  | Kabat |  | CDR-L1 | 22 |
|  |  |  | CDR-L2 | 23 |
|  |  |  | CDR-L3 | 16 |
|  |  | CDR-H1 |  | 24 |
|  |  | CDR-H2 |  | 25 |
|  |  | CDR-H3 |  | 26 |
|  |  |  | Mu. variable domain | 20 |
|  |  | Mu. variable domain |  | 21 |
| 301aE5 | IMGT |  | CDR-L1 | 41 |
|  |  |  | CDR-L2 | 15 |
|  |  |  | CDR-L3 | 42 |
|  |  | CDR-H1 |  | 43 |
|  |  | CDR-H2 |  | 44 |
|  |  | CDR-H3 |  | 45 |
|  | Kabat |  | CDR-L1 | 48 |
|  |  |  | CDR-L2 | 49 |
|  |  |  | CDR-L3 | 50 |
|  |  | CDR-H1 |  | 51 |
|  |  | CDR-H2 |  | 52 |
|  |  | CDR-H3 |  | 53 |
|  |  |  | Mu. variable domain | 46 |
|  |  | Mu. variable domain |  | 47 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10× Denhardt's, 5% dextran sulfate and 1% salmon sperm DNA; (2) primary hybridization for 20 hours at a temperature depending on the length of the probe (i.e.: 42° C. for a probe>100 nucleotides in length) followed by two 20-minute washings at 20° C. in 2×SSC+2% SDS, one 20—minute washing at 20° C. in 0.1×SSC+0.1% SDS. The last washing is carried out in 0.1×SSC +0.1% SDS for 30 minutes at 60° C. for a probe>100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also encompasses an isolated nucleic acid molecule characterized in that it is selected among the following nucleic acids:
   a) a nucleic acid, DNA or RNA, coding for a humanized antibody heavy chain, or for a derived compound or functional fragment of same, according to the invention;
   b) a nucleic acid, DNA or RNA, coding for a humanized antibody light chain, or for a derived compound or functional fragment of same, according to the invention;
   c) a nucleic acid, DNA or RNA, coding for a humanized antibody, or for a derived compound or functional fragment of same, according to the invention;
   d) a nucleic acid complementary to a nucleic acid as defined in a), b) or c);
   e) a nucleic acid of at least 18 nucleotides capable of hybridizing under highly stringent conditions with at least a heavy chain comprising the nucleic acid sequences SEQ ID No. 72 or 75 to 77;
   f) a nucleic acid of at least 18 nucleotides capable of hybridizing under highly stringent conditions with at least a light chain comprising the nucleic acid sequences SEQ ID No. 73, 74, 86, 87 or 78, 79, 88, 89.

The table 6 thereafter summarizes the nucleotide sequences of the various heavy and light chains variable domains and full length (or complete), respectively, of the humanized antibody 515H7 according to the invention.

TABLE 6

(wherein Hz = humanized)

| Antibody Hz515H7 | Heavy chain | Light chain | SEQ ID NO. |
|---|---|---|---|
| Variable Domains | VH1 D76N | — | 72 |
| | — | VL2 | 73 |
| | — | VL2.1 | 74 |
| | — | VL2.2 | 86 |
| | — | VL2.3 | 87 |
| Complete Sequences (without signal peptide) | VH1 D76N (G4wt) | — | 75 |
| | VH1 D76N (G4PRO) | — | 76 |
| | VH1 D76N (G2 wt) | — | 77 |
| | — | VL2-Ck | 78 |
| | — | VL2.1-Ck | 79 |
| | — | VL2.2-Ck | 88 |
| | — | VL2.3-Ck | 89 |

The table 7 herein-under summarizes the nucleotide sequences of the various heavy and light chains of the chimeric antibody 515H7 according to the invention.

TABLE 7

(wherein c = chimeric)

| Antibody c515H7 | Heavy chain | Light chain | SEQ ID NO. |
|---|---|---|---|
| Complete Sequences (without signal peptide) | cVH (G4wt) | — | 60 |
| | cVH (G4PRO) | — | 61 |
| | cVH (G2 wt) | — | 62 |
| | — | cVL-Ck | 63 |

In other words, the invention deals with an isolated nucleic acid, characterized in that it is chosen from the following nucleic acids:
   a) a nucleic acid, DNA or RNA, coding for an antibody, or one of its functional fragments or derivatives, according to the invention;
   b) a nucleic acid comprising a DNA sequence selecting from the group of CDRs sequences consisting of SEQ ID Nos. 14 to 19 and 41 to 45;
   c) a nucleic acid comprising a DNA sequence selecting from the group of heavy and light variable domains sequences consisting of SEQ ID Nos. 20, 21, 46, 47, 72, 73, 74, 86 and 87;
   d) a nucleic acid comprising a DNA sequence selecting from the group of heavy and light chains sequences consisting of SEQ ID Nos. 60 to 63, 75 to 79, 88 and 89;
   e) a nucleic acid comprising a DNA sequence consisting of SEQ ID No. 55;
   f) the corresponding RNA nucleic acids of the nucleic acids as defined in b), c), d) or e);
   g) the complementary nucleic acids of the nucleic acids as defined in a), b), c), d) and e); and
   h) a nucleic acid of at least 18 nucleotides capable of hybridizing under conditions of high stringency with at least one of the CDRs of sequence SEQ ID Nos. 14 to 19 and 41 to 45.

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, that have a transformed cell according to the invention.

Another aspect of the invention relates to a method for the production of an antibody according to the invention, or one of its functional fragments, characterized in that said method comprises the following steps:

a) the culture in a medium of and the suitable culture conditions for a host cell according to the invention; and b) the recovery of said antibody, or one of its functional fragments, thus produced from the culture medium or from said cultured cells.

The transformed cells according to the invention are of use in methods for the preparation of recombinant polypeptides according to the invention. Methods for the preparation of polypeptide according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid polypeptide and recovery of said recombinant peptide.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The polypeptides of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, 111, 2nd ed.) or partial solid-phase techniques, by condensation of fragments or by conventional synthesis in solution. Polypeptides obtained by chemical synthesis and capable of containing corresponding unnatural amino acids are also comprised in the invention.

The antibodies, or the derived compounds or functional fragments of same, likely to be obtained by the method of the invention are also comprised in the present invention.

According to still another aspect, the present invention relates to antibodies as described above, characterized in that they are, in addition, capable of specifically binding to a human chemokine family receptor and/or capable of specifically inhibiting X4-tropic HIV replication.

According to still another aspect, the present invention relates to antibodies as described above, characterized in that they are, in addition, capable of specifically binding to a human chemokine family receptor and/or capable of specifically inhibiting X4/R5-tropic HIV replication.

According to a novel embodiment, the invention relates to antibodies, or their derived compounds or functional fragments, consisting of antibody that are bispecific in the sense that they comprise a second motif capable of interacting with any receptor implicated in HIV cell entry, such as, for example, CCR5, CD4, CXCR4 (other than the antibody of the present invention, i.e. targeting another epitope) or CCR3, CCR2, CCR8, CXCR6, CXCR7, CX3CR1.

The bispecific or bifunctional antibodies constitute a second generation of monoclonal antibodies in which two different variable regions are combined in the same molecule (Hollinger and Bohlen, 1999, Cancer and metastasis, rev. 18:411-419). Their utility was demonstrated in both diagnostic and therapeutic domains relative to their capacity to target several molecules on the surface of cells; such antibodies can be obtained by chemical methods (Glennie M J et al., 1987, J. Immunol. 139, 2367-2375; Repp R. et al., 1995, J. Hemat., 377-382) or somatic methods (Staerz U. D. and Bevan M. J., 1986, PNAS 83, 1453-1457; Suresh M. R. et al., 1986, Method Enzymol., 121:210-228) but also, preferentially, by genetic engineering techniques that make it possible to force heterodimerization and thus facilitate the purification of the antibody sought (Merchand et al., 1998, Nature Biotech., 16:677-681).

These bispecific antibodies can be constructed as whole IgG, bispecific Fab'2, Fab'PEG, diabodies or bispecific scFv, but also as a tetravalent bispecific antibody in which two binding sites are present for each antigen targeted (Park et al., 2000, Mol. Immunol., 37(18):1123-30) or the fragments of same as described above.

In addition to an economic advantage given that the production and administration of a bispecific antibody are cheaper than the production of two specific antibodies, the use of such bispecific antibodies has the advantage of reducing the treatment's toxicity. Indeed, the use of a bispecific antibody makes it possible to decrease the overall quantity of circulating antibodies and, consequently, possible toxicity.

In a preferred embodiment of the invention, the bispecific antibodies are bivalent or tetravalent antibodies.

Lastly, the present invention relates to the antibodies described above, or one of their functional fragments or derivatives, as a medicament.

The invention also relates to a pharmaceutical composition comprising as an active ingredient a compound consisting of an antibody of the invention, or one of its functional fragments or derivatives. Preferably, said antibody is supplemented by an excipient and/or a pharmaceutically acceptable carrier.

The invention also relates to the composition as above described as a medicament.

In a particular aspect of the invention, the antibody, or one of its functional fragments or derivatives, inhibits HIV-1 KON primary isolate replication in PBMC with an $IC_{90}$ of at least 5 µg/ml, preferably at least 10 µg/ml.

The present invention also comprises the use of an antibody or the composition according to the invention for the preparation of a drug and/or medicament for the prevention or the treatment of HIV infection.

More particularly, as a non limitative example, said HIV infection is a X4-tropic HIV infection.

In another embodiment, as a non limitative example, said HIV infectious is a X4/R5-tropic HIV infection.

The present invention also relates to the use of an antibody, or a functional fragment or derivative of same, preferably humanized, and/or of a composition according to the invention for the preparation of a drug for inhibiting HIV replication. Generally, the present invention relates to the use of an antibody, or a functional fragment or derivative of same, preferably humanized, and/or of a composition, for the preparation of a drug for HIV disease prevention or treatment.

In the present description, "pharmaceutical vehicle" means a compound, or a combination of compounds, entering a pharmaceutical composition that does not cause secondary reactions and that, for example, facilitates administration of the active compounds, increases its lifespan and/or effectiveness in the organism, increases its solubility in solution or improves its storage. Such pharmaceutical carriers are well-known and will be adapted by a person skilled in the art according to the nature and the administration route of the active compounds selected.

Preferably, such compounds will be administered by systemic route, notably by intravenous, intramuscular, intradermal, intraperitoneal, subcutaneous, intravaginal or oral route. More preferably, the composition composed of the antibody according to the invention will be administered in several doses spaced equally over time.

Their administration routes, dosing schedules and optimal galenic forms can be determined according to the criteria generally taken into account when establishing a treatment suited to a patient such as, for example, the patient's age or body weight, the seriousness of his general state, his tolerance for the treatment and the side effects experienced.

The invention also relates to a composition comprising, in addition, as a combination product for use in a simultaneous, separated or extended fashion, an anti-HIV antibody or an anti-HIV cell entry antibody or an anti-HIV replication antibody other that an antibody directed against CXCR4.

According to still another embodiment, the present invention also relates to a pharmaceutical composition as described above that comprises at least a second anti-HIV compound selected among the compounds capable of specifically inhibiting HIV entry and/or replication such as anti-CCR5, anti-CD4 compounds and anti-CXCR4 compounds other than those described in this invention, or any other anti-HIV compound known to a person skilled in the art.

Another embodiment complementary to the invention consists of a composition as described above comprised of, in addition, as a combination or conjugation product for simultaneous, separated or extended use, an anti-HIV compound.

"Simultaneous use" means the administration of both compounds of the composition comprised in a single dosage form.

"Separated use" means administration, at the same time, of both compounds of the composition, comprised in distinct dosage forms.

"Extended use" means the successive administration of both compounds of the composition, each comprised in a distinct dosage form.

Generally, the composition according to the invention considerably increases HIV treatment effectiveness. In other words, the therapeutic effect of the antibody of the invention is enhanced in an unexpected way by the administration of an anti-HIV agent. Another major subsequent advantage produced by a composition of the invention relates to the possibility of using lower effective doses of the active ingredient, thus making it possible to avoid or reduce the risks of the appearance of side effects, in particular the effect of the anti-HIV agent. Moreover, this composition makes it possible to achieve the expected therapeutic effect more quickly.

"Therapeutic anti-HIV agent" means a substance which, when it is administered to a patient, treats or prevents the replication of HIV in the patient. Non-limiting examples of such agents include "antiretroviral drugs such as HIV protease inhibitors (PI), nucleoside/nucleotide HIV reverse-transcriptase inhibitors (NRTI/NtRTI) non-nucleoside HIV reverse-transcriptase inhibitors (NNRTI), HIV entry inhibitors, HIV integrase inhibitors".

Such agents, for example, are cited in VIDAL, on the pages devoted to compounds related to "anti-HIV compounds"; the anti-HIV compounds cited by reference to this document are cited herein as non limitative preferred anti-HIV agents.

HIV protease inhibitor refers to any substance that can inhibit HIV protease activity. Examples of such HIV protease inhibitors include, but are not limited to Saquinavir mesylate or SQV (Invirase®), Indinavir or IDV (Crixivan®), Ritonavir or RTV (Norvir®), Nelfinavir or NFV (Viracept®), Amprenavir (Agenerase®, Prozei®), Lopinavir/ritonavir or LPV/r (Kaletra®, Aluvia®), Atazanavir or ATV (Reyataz®, Zrivada®), Fosamprenavir or FPV (Lexiva®, Telzir®), Tipranavir or TPV (Aptivus®), Darunavir or DRV (Prezista®)

HIV Nucleoside or nucleotide reverse-transcriptase inhibitor (NRTI) refers to a substance which is a nucleoside or nucleotide analogue that blocks reverse-transcription of HIV RNA. Examples of NRTI include, but are not limited to Zidovudine or AZT,ZDV (Retrovir/combivir/trixivir®), Didanosine or ddi (Videx®), Zalcitabine (HIVID®), Stavudine or d4T (Zerit®), Lamivudine or 3TC (Epivir/combivir/epzicom/trixivir®), Abacavir or ABC (Ziagen/trixivir/epzicom®), Tenofovir disoproxil fumarate or TDF (Viread/atripla/truvada®), Emtricitabine or FTC (Emtriva/atripla/truvada®)

Non-nucleoside HIV reverse-transcriptase inhibitor (NNRTI) refers to a substance which is not a nucleoside or nucleotide analogue that blocks reverse-transcription of HIV RNA. Examples of NNRTI include, but are not limited to Nevirapine or NVP (Viramune®), Efavirenz or EFV (Sustiva/atripla®, Stocrin®), Delavirdine or DLV (Rescriptor®) and Etravirine or ETR (Intelence®).

HIV entry inhibitor refers to a substance that block HIV cell entry. Examples of HIV entry inhibitors include, but are not limited to Enfuvirtide or T20 (Fuzeon®), Maraviroc or MVC (Celsentri®, Celzentry®).

HIV integrase inhibitor refers to a substance that inhibits HIV integrase activity. Example of integrase inhibitor includes, but is not limited to Raltegravir or RAL (Isentress®).

Such agents, for example, are also compounds belonging to the same classes of drugs described in VIDAL, which are currently in clinical trials such as but not limited to Vicriviroc, PRO140, TNX-355, AMD070, Racivir, Apricitabine, Elvucitabine, Flosalvudine, Rilpivirine, Elvitegravir.

Such agents, for example, are also compounds belonging to other potential classes of drugs such as but not limited to maturation inhibitors (Bevirimat), glycoside analogues of β-galactosyl-ceramide, carbohydrate-binding agents, RNaseH inhibitors, HIV gene expression inhibitors, stimulators of HIV release from latent T cells (valproic acid . . . ).

In a particularly preferred embodiment, said composition of the invention as a combination product is characterized in that said anti-HIV agent is bound chemically to said antibody for use simultaneously.

In order to facilitate binding between said anti-HIV agent and the antibody according to the invention, spacer molecules can be introduced between the two compounds to bind, such as the poly(alkylene)glycol polyethyleneglycol or the amino acids; or, in another embodiment, said anti-HIV agents' active derivatives, into which have been introduced functions capable of reacting with said antibody, can be used. These binding techniques are well-known to a person skilled in the art and will not be discussed in more detail in the present description.

Also preferably, said antibody of the invention forming said conjugate is selected among its functional fragments, notably fragments that have lost their Fc component, such as scFv fragments.

The invention also relates to a composition as a combination product or to an anti-CXCR4 Mab/anti-HIV drug conjugate, according to the invention, used as drug.

Preferably, said composition as a combination product or said conjugate will be supplemented by an excipient and/or a pharmaceutical vehicle.

Thus, the invention relates to the use of an antibody, or one of its functional fragments or derivatives, for the preparation of a drug for the specific targeting of a compound that is biologically active toward HIV replication.

In another embodiment, the invention also relates to a method for HIV prevention or treatment, wherein said method comprises a step consisting of administering to a patient in need thereof, an antibody, or one of its antigen binding fragments or derivatives and/or a composition, according to the invention.

More particularly, the method according to the invention comprises also a step consisting of administering to said patient an anti-CCR5 compound, such as Maraviroc.

As previously demonstrated, CXCR4 Mabs 515H7 and 301aE5 have strong activities against HIV-1 replication in PBMC, so such antibodies could be used in screening assays for identification of CXCR4 antagonist antiviral agents to treat HIV-1 infection. In the first step of these assays, cells expressing CXCR4 are incubated with Mabs 515H7 and/or 301aE5 and then molecules can be evaluated for their potential to inhibit Mabs 515H7 and/or 301aE5 binding. Cells used in this type of assays can be transfected cell lines such as CHO-CXCR4, NIH3T3-CXCR4 or CXCR4 transfected human cell lines such as U373-MAGI-CXCR4, human cell lines expressing CXCR4 such as NALM6 or primary cells such as PBMC. The method used to screen antagonists of CXCR4 inhibiting Mabs 515H7 and/or 301aE5 binding on CXCR4 expressing cells can be cell-based competitive enzyme-linked immunosorbent Assay (ELISA) as described by Zhao Q. et al. (AIDS Research And Human Retroviruses, 2003, 19, pp 947-955) or protocols using Fluorescence-Activated cell Sorting (FACS) such as described by Juarez J. et al. (Leukemia 2003, 17, pp 1294-1300).

Thus, in a particular aspect of the invention, it is considered a process for the screening and/or the identification of molecules as CXCR4 antagonist antiviral agents comprising the steps of:

a) selecting cells expressing CXCR4, b) incubating said cells with an antibody, or one of its functional fragments or derivatives, of the invention, and c) evaluating the tested molecules for their potential inhibition of the binding between the antibody, or one of its functional fragments or derivatives, to CXCR4, and d) selecting molecules capable of said inhibition.

In another particular embodiment, the following step e) can be added:

e) testing these molecules in a HIV-1 replication assay.

Other characteristics and advantages of the invention appear further in the description with the examples and figures whose legends are presented below.

FIGURE LEGENDS

FIGS. 1A and 1B show the gating strategy for CXCR4 expression on monocytes and lymphocytes.

FIG. 1A: T cell staining with CD3-PE antibody.

FIG. 1B: monocytes staining with CD14-PE antibody.

FIGS. 6A, 6B and 6C show the inhibition of SDF-1-induced calcium release in CHO-CXCR4 cells by Mabs 515H7 (FIG. 6A), 301aE5 (FIG. 6B) and c515H7 (FIG. 6C).

FIG. 17: Amino acid sequences alignment of 515H7 heavy chain variable domain (SEQ ID NO: 8) with the human germline IGHV3-49*04 (SEQ ID NO: 94) and IGHJ4*01 (SEQ ID NO: 95). The 515H7 VH amino acid sequence is aligned with the selected human acceptor framework sequences. VH Var1 (VH1) sequences (SEQ ID NOS 90 and 64, respectively, in order of appearance) correspond to the humanized variants of 515H7 VH domains. The single back mutation in position 76 is depicted in bold.

FIG. 18: Amino acid sequences alignment of 515H7 light chain SEQ ID NO: 96) with the human germline IGKV4-1*01 (SEQ ID NO: 97) and IGKJ1*01 (SEQ ID NO: 96) The 515H7 VL amino acid sequence is aligned with the selected human acceptor framework sequences. VL Var2.1 (SEQ ID NO: 66), Var2.2 (SEQ ID NO: 82) and Var2.3 (SEQ ID NO: 83) sequences correspond to implemented humanized variants of the humanized 515H7 VL Var2 (SEQ ID NO: 65), with mutated residues in bold. Var2.1 and Var2.2 carry 4 more humanized residues whereas Var2.3 contains 5 more human residues.

Figure 19:
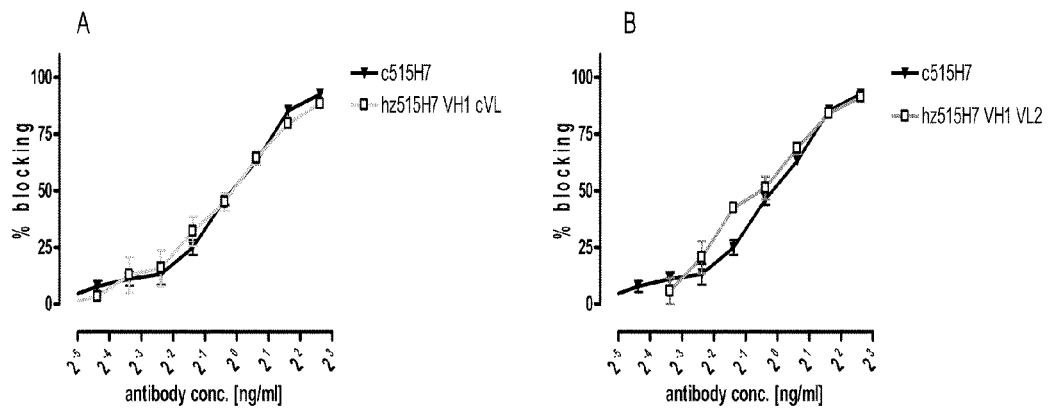

FIG. 19: Cross blocking of the biotinylated murine antibody 515H7 by the chimeric 515H7 and different variants of the humanized 515H7. The activity of the humanized variants of 515H7 (hz515H7) to cross block the parental murine antibody 515H7 was evaluated by flow cytometry using CXCR4 transfected NIH3T3 cells. The activity of the humanized variants was compared to the chimeric 515H7. The cross blocking activity of the variant VH1 combined with the chimeric VL (cVL) was very similar to that of the chimeric (A). No reduction in the activity of VH variant 1 (VH1, the variant with no back mutations) was determined when combined with variant 2 of VL (B).

Figure 20:
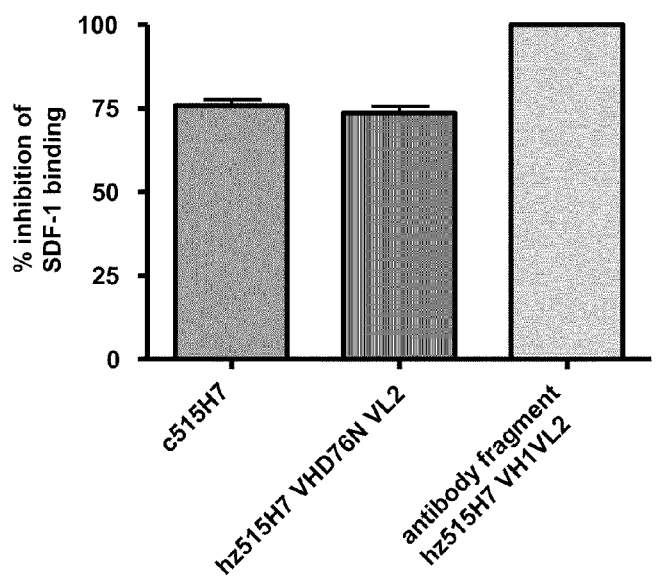

FIG. 20: Inhibition of the biotinylated SDF-1 binding by the chimeric 515H7 and different variants of the humanized 515H7. The capacity of the humanized variant of 515H7 (hz515H7) to inhibit SDF-1 binding was evaluated by flow cytometry using the cell line RAMOS. The inhibition capacity of the humanized variants was compared to the chimeric 515H7. The humanized variant hz515H7 VH1 D76N VL2 has a similar capacity to inhibit SDF-1 binding as the chimeric antibody. The humanized antibody fragment hz515 VH1 VL2 was fully active in inhibiting the binding of SDF-1 to RAMOS cells.

Figure 21:
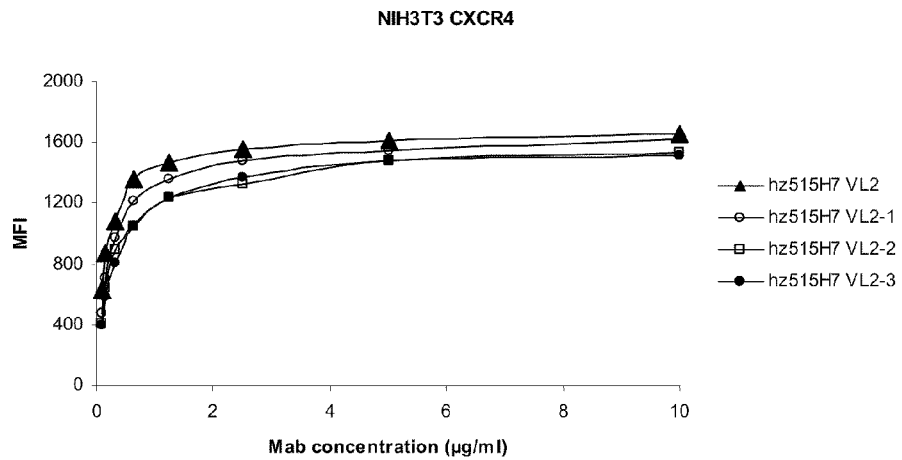

FIG. 21 shows humanized 515H7 Mabs (hz515H7 VH1 D76N VL2, hz515H7 VH1 D76N VL2.1, hz515H7 VH1 D76N VL2.2 and hz515H7 VH1 D76N VL2.3) specific binding to CXCR4 on NIH3T3-CXCR4.

Figure 22:
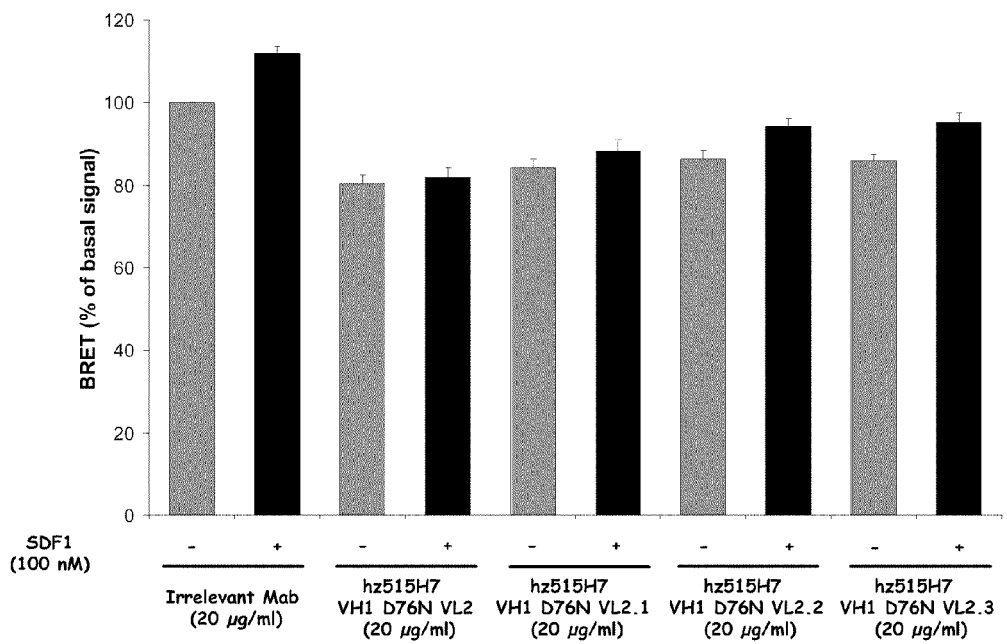

FIG. 22 shows the effect of humanized 515H7 Mabs (hz515H7 VH1 D76N VL2, hz515H7 VH1 D76N VL2.1, hz515H7 VH1 D76N VL2.2 and hz515H7 VH1 D76N VL2.3) on CXCR4 homodimer, by bioluminescence resonance energy transfer (BRET) approach.

Figure 23:
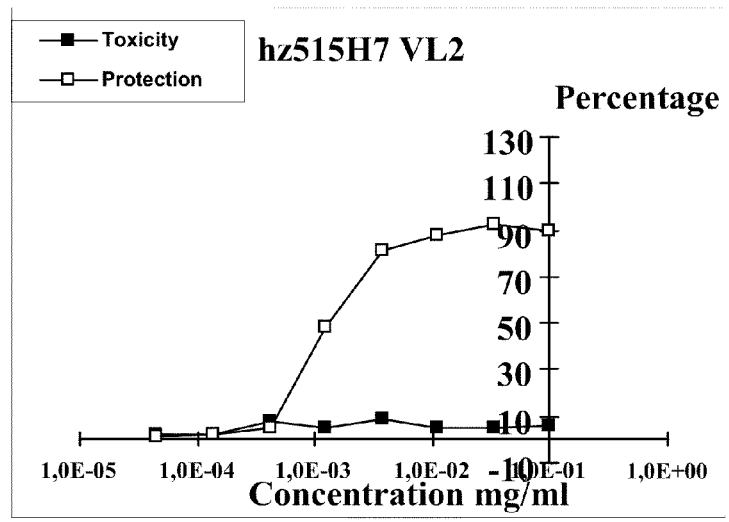

FIG. 23 shows the ability of anti-CXCR4 Mab hz515H7 to inhibit X4 HIV-1$_{IIIB}$-induced cytopathogenicity in MT-4 cells.

Figure 24:
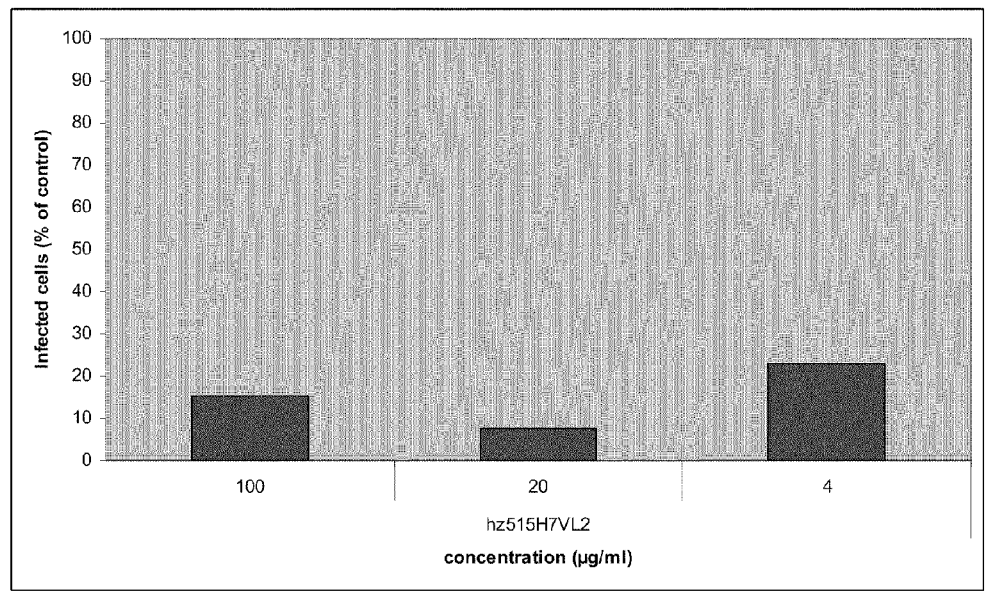

FIG. 24 shows the ability of anti-CXCR4 Mab hz515H7 to inhibit HIV-1 X4 virus primary isolate KON replication in human PBMC.

Figure 25:
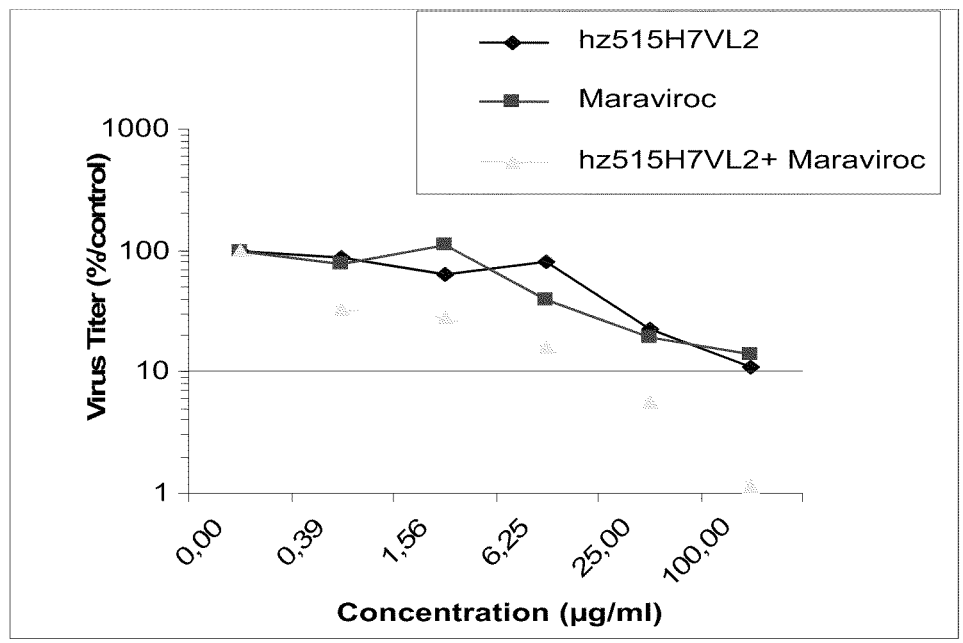

FIG. 25 shows the beneficial effect of combining Mab hz515H7 with Maraviroc to inhibit HIV-1 primary isolate 89.6 (dual X4/R5 virus) replication in human PBMC.

Figure 26:
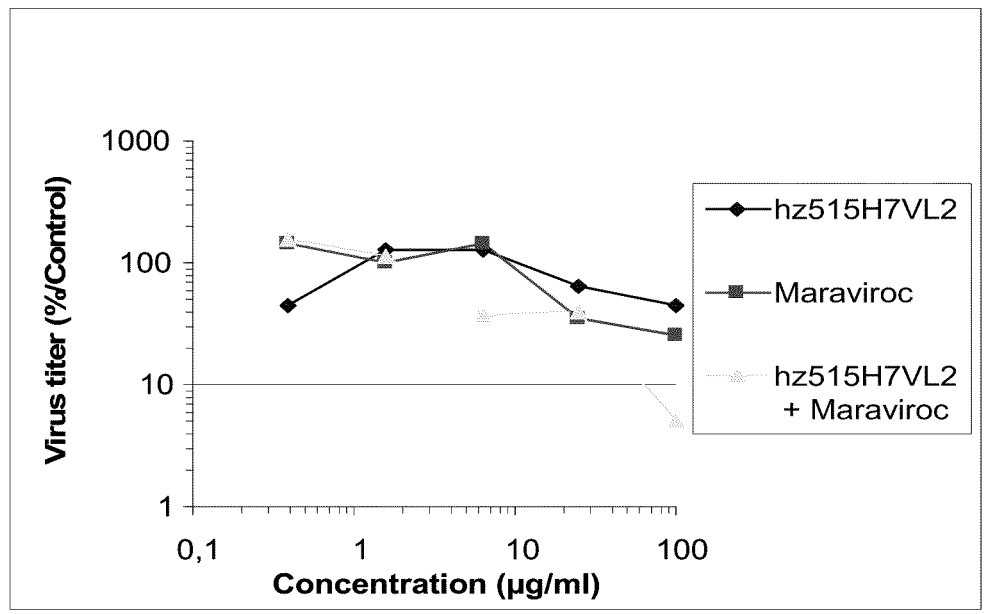

FIG. 26 shows the beneficial effect of combining Mab hz515H7 with Maraviroc to inhibit HIV-1 primary isolate UG93067 (dual X4/R5 virus) replication in human PBMC.

EXAMPLES

Example 1

Generation of Monoclonal Antibodies (Mabs) Against Human CXCR4

To generate monoclonal antibodies to CXCR4, Balb/c mice were immunized with recombinant NIH3T3-CXCR4 cells and/or peptides corresponding to CXCR4 extracellular N-term and loops. 6-16 weeks of age mice were immunized once with the antigen in complete Freund's adjuvant subcutaneously (s.c.) followed by 2 to 6 immunizations with antigen in incomplete Freund's adjuvant s.c. The immune response was monitored by retroorbital bleeds. The serum was screened by ELISA (as described bellow) and mice with the higher titers of anti-CXCR4 antibodies were used for fusions. Mice were boost intravenously with antigen two days before sacrifice and removal of the spleen.

ELISA

To select the mice producing anti-CXCR4 antibodies, sera from immunized mice was tested by ELISA. Briefly, microtiter plates were coated with purified [1-41] N-terminal peptide conjugated to BSA at 5 µg equivalent peptide/mL, 100 µL/well incubated at 4° C. overnight, then blocked with 250 µL/well of 0.5% gelatine in PBS. Dilutions of plasma from CXCR4-immunized mice were added to each well and incubated 2 hours at 37° C. The plates were washed with PBS and then incubated with a goat anti-mouse IgG antibody conjugated to HRP (Jackson Laboratories) for 1 hour at 37° C. After washing, plates were developed with TMB substrate, the reaction was stopped 5 min later by addition of 100 µL/well 1M $H_2SO_4$. Mice that developed the highest titers of anti-CXCR4 antibodies were used for antibody generation.

Generation of Hybridomas Producing Mabs to CXCR4

The mouse splenocytes, isolated from a Balb/c mice that developed the highest titers of anti-CXCR4 antibodies were fused with PEG to a mouse myeloma cell line Sp2/O. Cells were plated at approximately $1 \times 10^5$/well in microtiter plates followed by two weeks incubation in selective medium containing ultra culture medium+2 mM L-glutamine+1 mM sodium pyruvate+1×HAT. Wells were then screened by ELISA for anti-CXCR4 monoclonal IgG antibodies. The antibody secreting hybridomas were then subcloned at least twice by limiting dilution, cultured in vitro to generate antibody for further analysis.

Example 2

Characterization of Anti-CXCR4 Mab 515H7 and 301aE5 Binding Specificity (NIH3T3-CXCR4 Transfectant) by FACS Analysis In this experiment, the specific binding to human CXCR4 (hCXCR4) of anti-CXCR4 Mabs 515H7 and 301aE5 was examined by FACS analysis.

NIH3T3 and NIH3T3-hCXCR4 transfected cells were incubated with 10 µg/ml of monoclonal antibodies 515H7 and 301aE5. The cells were then washed with 1% BSA/PBS/0.01% NaN3. Next, Alexa-labeled secondary antibodies were added to the cells and were allowed to incubate at 4° C. for 20 min. The cells were then washed again two times. Following the second wash, FACS analysis was performed. Results of these binding studies are provided in the following Table 8 which shows [Mean Fluorescence Intensity (MFI) obtained by FACS] that anti-CXCR4 Mabs 515H7 and 301aE5 bind specifically to human CXCR4-NIH3T3 transfected cell line whereas there was no recognition on the parent NIH3T3 cells.

TABLE 8

|  | NIH3T3 (MFI) | NIH3T3-CXCR4 (MFI) |
|---|---|---|
| Clone 515H7 (10 µg/ml) | 16 | 2752 |
| Clone 301aE5 (10 µg/ml) | 21 | 1367 |

Example 3

Figure 1A:
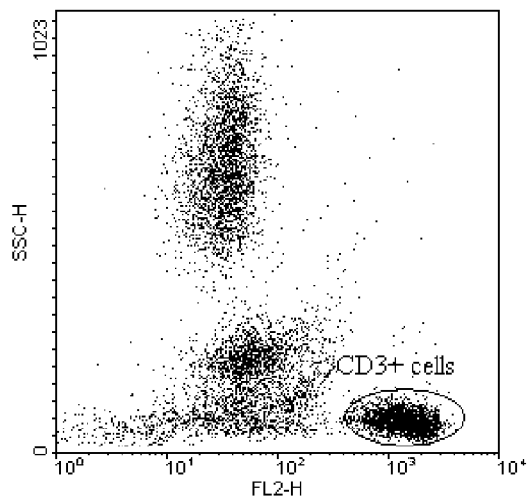
Figure 1B:
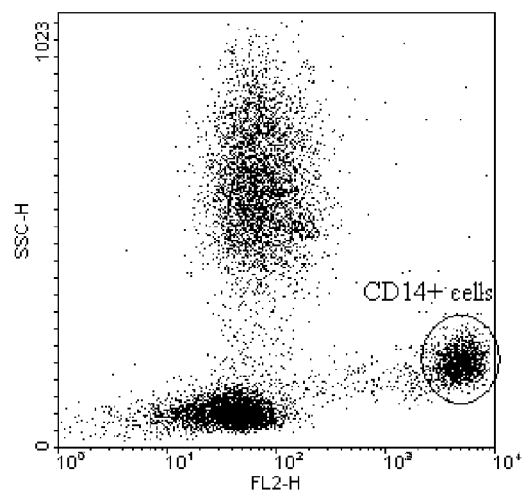

Characterization of Anti-CXCR4 Mab 515H7 and 301aE5 Binding to Peripheral Blood Mononuclear Cells (PBMC) by FACS Analysis Blood was collected as buffy coat from healthy donor. 100 µl of whole blood was incubated with anti-human CXCR4 antibodies (clones 515H7 and 301aE5) at the indicated concentration for 20 minutes at 4° C. Blood was washed three times in PBS-BSA 1%-NaN3 0.01% and incubated with goat anti-human Alexa 488 IgG diluted 1:500 (Invitrogen) for 20 minutes at 4° C. Cells were then washed and incubated with CD14-PE (Caltag) or CD3-PE (Caltag) for 10 minutes at 4° C. and washed three times. Red blood cells were lysed with High-Yield lyse solution (Caltag) for 10 minutes at room temperature. Cells were analyzed immediately using Facscalibur (Becton-Dickinson). CXCR4 expression on monocytes was done on CD14 positive cells and CXCR4 expression on T cell was done on CD3 positives cells (FIG. 1). Results are expressed in Antigen Binding Capacity (ABC).

Figure 2A:
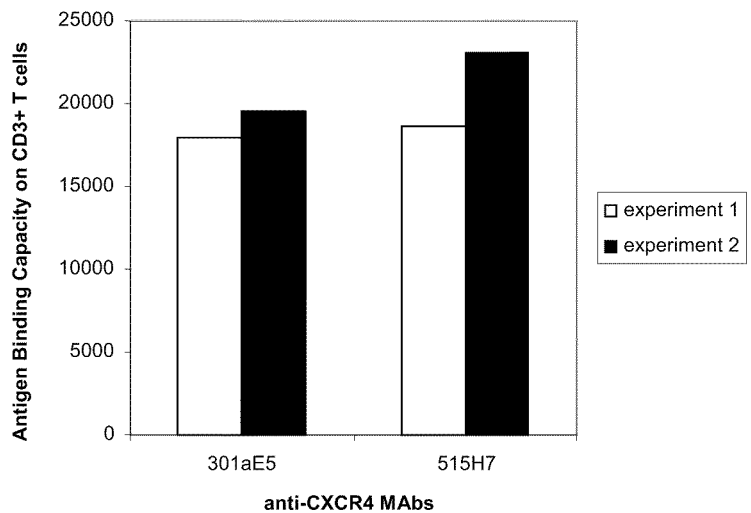
FIGS. 2A and 2B show the binding of anti-CXCR4 Mabs 515H7 and 301aE5 on monocytes and T lymphocytes.
Figure 2B:
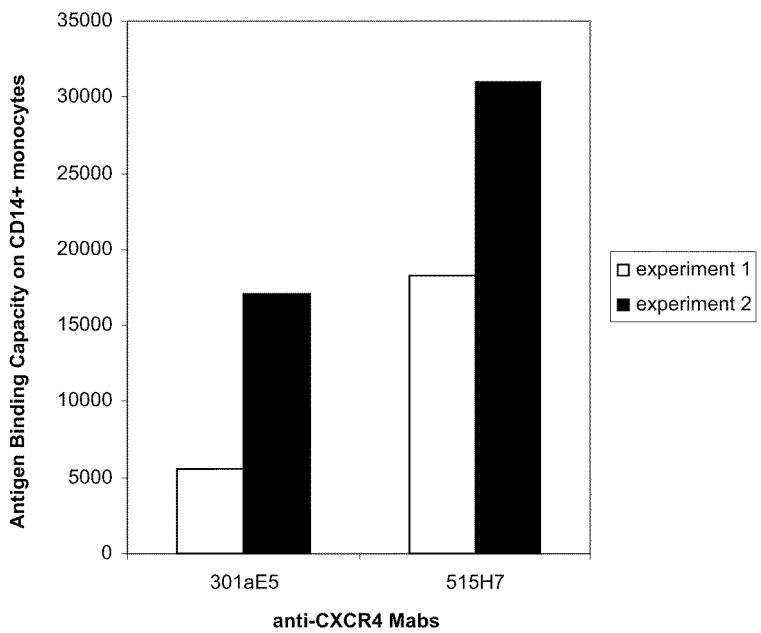

As shown in FIGS. 2A and 2B, the anti-human CXCR4 clones 515H7 and 301aE5 stained both T lymphocytes (FIG. 2A) and monocytes (FIG. 2B) indicating that 515H7 and 301aE5 Mabs are able to recognize the native form of CXCR4 expressed at the cell surface of monocytes and T lymphocytes.

Example 4

Effect of 515H7 and 301aE5 Mabs on CXCR4 Homodimer, by Bioluminescence Resonance Energy Transfer (BRET) Approach This functional assay allows to evaluate the conformational changes induced upon SDF-1 and/or 515H7 Mab binding to CXCR4 receptor at the level of CXCR4 homodimer.

Expression vectors for the investigated interaction partners were constructed as fusion proteins with the corresponding dye (*Renilla reniformis* luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4/Rluc+CXCR4/YFP] to study CXCR4 homodimerization. The day after, cells were distributed in poly-lysine pre-coated white 96 MW plates in complete culture medium [DMEM supplemented with 10% FBS]. Cells were first cultivated at 37° C. with $CO_2$ 5% in order to allow cell attachment to the plate. Cells were then starved with 200 µl DMEM/well overnight Immediately prior to the BRET experiment, DMEM was removed and cells were quickly washed with PBS. Cells were then incubated in PBS in the presence or absence of antibody, 10 min at 37° C. prior to the addition of coelenterazine H 5 µM with or without SDF-1 300 nM in a final volume of 50 µl. After incubation for further 10 minutes at 37° C., light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): $[(\text{emission}_{530\ nm})-(\text{emission}_{485\ nm})\times Cf]/(\text{emission}_{485\ nm})$, where $Cf=(\text{emission}_{530\ nm})/(\text{emission}_{485\ nm})$ for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed in milliBRET units (mBU); mBU corresponds to the BRET ratio multiplied by 1000.

Figure 3A:
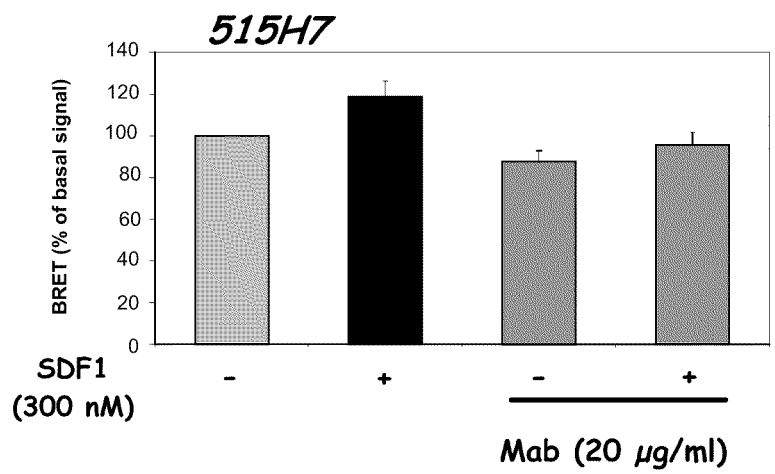
FIGS. 3A and 3B show the modulation of CXCR4 receptor dimer by SDF-1 and by anti-CXCR4 Mabs 515H7 and 301aE5, respectively, via a bioluminescence resonance energy transfer (BRET) approach in HEK293 cells.
Figure 3B:
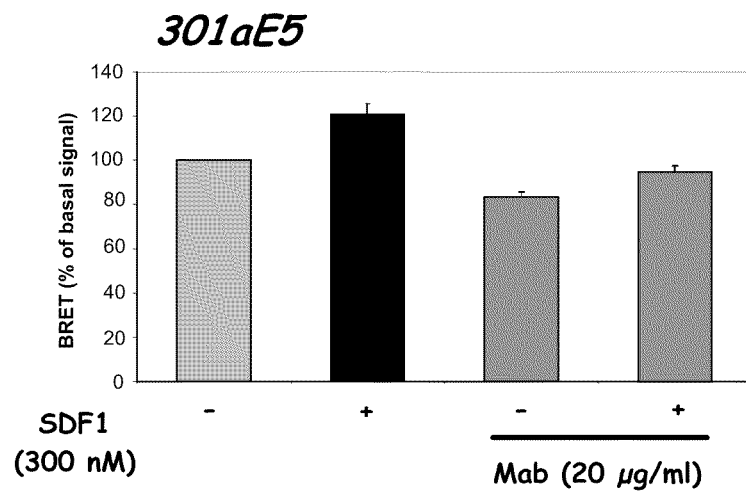

SDF1 (300 nM) increased by about 20% the BRET signal resulting from the spatial proximity of the adaptor and acceptor proteins fused to CXCR4 receptor, it is likely to indicate CXCR4/CXCR4 homo-dimers formation or conformational changes of pre-existing dimers (FIGS. 3A and B). 515H7 and 301aE5 Mabs were able to modulate SDF-1-induced conformational changes for CXCR4 homo-dimers (69% inhibition of SDF-1-induced BRET increase for 515H7 and 301aE5, FIGS. 3A and B). 515H7 and 301aE5 Mabs were also able to modulate by themselves CXCR4/CXCR4 spatial proximity, indicating an influence of 515H7 and 301aE5 Mabs on CXCR4/CXCR4 homodimer conformation. (FIGS. 3A and 3B).

Example 5

Inhibition of HIV-1 Primary Isolate KON (X4 Virus) Replication in Human PBMC by anti-CXCR4 Mabs 515H7 and 301aE5

Figure 4A:
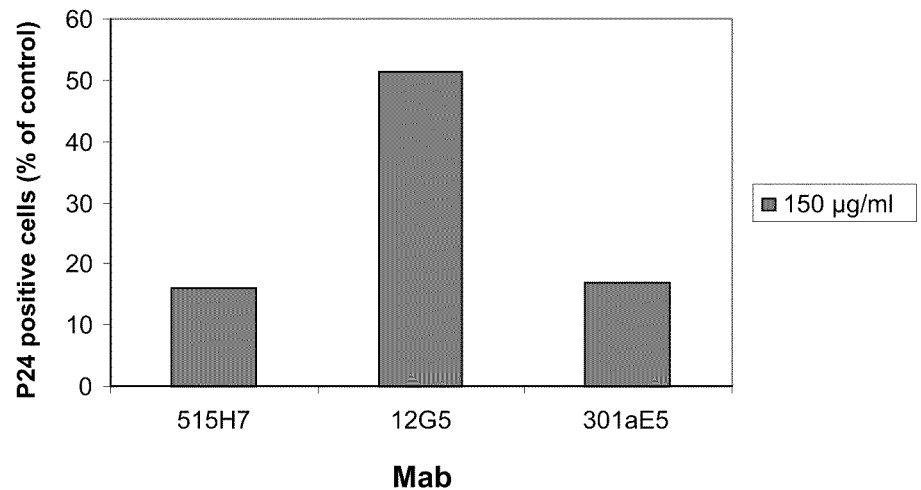
FIGS. 4A and 4B and FIG. 5 show the ability of anti-CXCR4 Mab 515H7 and 301aE5 to inhibit HIV-1 isolate KON (X4 virus) replication in human PBMC.
Figure 4B:
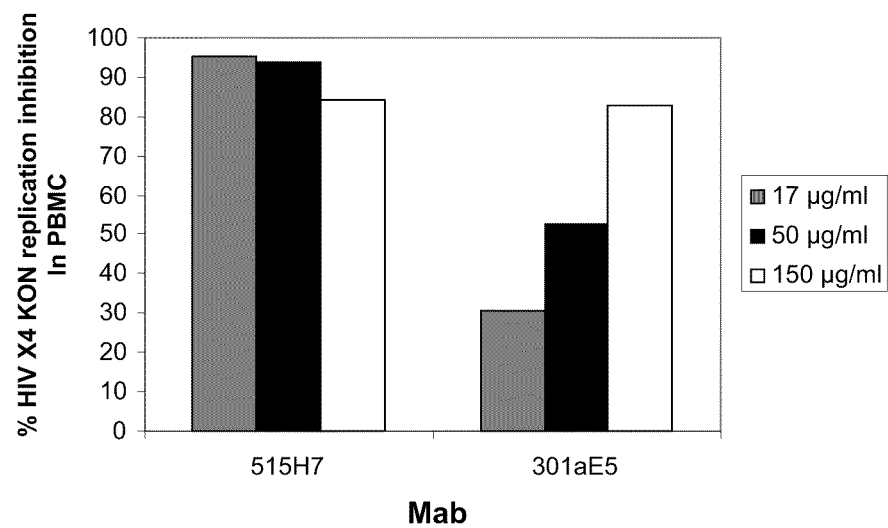
Figure 5:
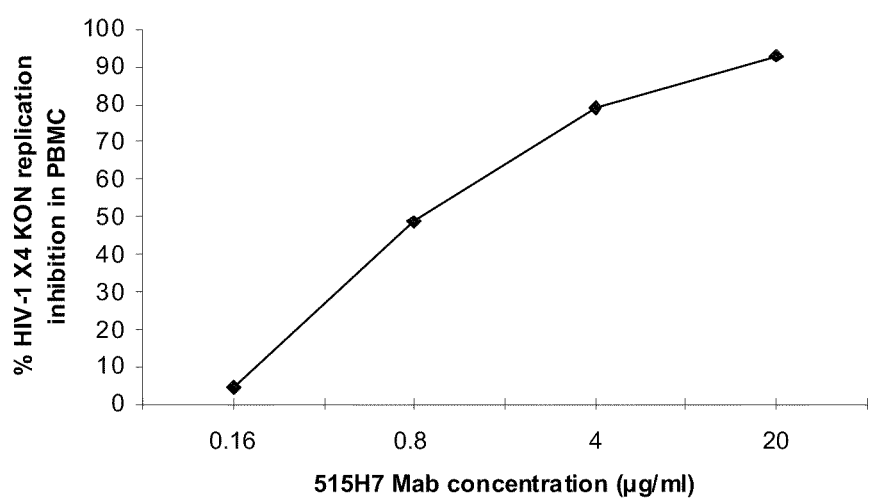

PBMC from normal donors seronegative for HIV-1 were isolated from buffy coats or cytapheresis by Ficoll-Hypaque gradient centrifugation. PBMC were activated in the presence of PHA in RPMI 1640 cell culture medium containing 25 mM HEPES, 5 ml penicillin (10000 U/ml)-streptomycin (10000 µg/ml) 2 mM L-glutamine, supplemented with 10% heat-inactivated FCS and were used as cellular targets in a single cycle neutralization assay. HIV-1 replication in primary human PBMC was performed by analyzing intracellular staining of viral p24 antigen by FACS analysis. Briefly, 25 µl per well of various dilutions of Mabs 515H7, 301aE5 and 12G5 (R&D Systems) or culture medium as control (RPMI 1640, 10% FCS, 0.1% IL-2), were incubated for 1 h at 37° C. with 25 µl per well of HIV-1 KON X4 primary isolate dilution, in duplicate. PHA-activated human PBMC (25 µl/well) at $20\times10^6$ cells/ml were added to the Mab/virus mixture in a 96-well plate (U-bottom, Costar 3599) and cultured for 24 to 36 hours at 37° C. in RPMI 1640 10% FCS and 0.1% IL-2. Control consisting of uninfected PBMC in medium without Mab was introduced. To detect HIV-infected PBMC, intracellular staining of viral p24 antigen was performed and analyzed by flow cytometry. Cells were fixed and permeabilized using the Cytofix/Cytoperm kit (Becton Dickinson) according to the manufacturer protocols and stained with a fluorescent anti-p24 Mab (clone KC57—Coulter Beckman) used at a 1/160 dilution incubated for 10 min at 4° C. in the dark. After washing in PBS-3% FCS medium, PBMC were diluted in PBS before flow cytometry analysis. The percentage of p24-positive cells in the different samples was determined by gating 20,000 events on a living cell population. The living cell subsets were analyzed for p24 expression relative to background staining of uninfected cells. The p24 antigen-positive value was obtained after subtraction of background events in mock-infected cells. The percentage of neutralization was defined as the reduction of p24-positive cells compared with control infected wells with no Mab. The neutralizing titer was defined as the dilution of Mab that allows a 90% decrease in the percentage of infected cells. The anti-CXCR4 Mabs 515H7 and 301aE5 were compared to 12G5 Mab known as the anti-CXCR4 Mab of reference for HIV application. As shown in FIGS. 4A and B and 5, the anti-CXCR4 Mabs 515H7 and 301aE5 are able to inhibit HIV-1 KON primary isolate replication in PBMC with an $IC_{90}$ of 10 µg/ml (66 nM) and 150 µg/ml (1 µM), respectively, whereas 12G5 Mab failed to inhibit HIV-1 KON primary isolate replication in PBMC (FIG. 4A).

Example 6

CXCR4 Receptor-Mediated Mobilization of Intracellular Calcium Stores

This functional assay was designed to monitor CXCR4 receptor signaling via stimulation of the phospholipase C pathway, inducing calcium liberation from intracellular stores from the endoplasmic reticulum.

CHO-K1 cells, stably and constitutively expressing human CXCR4 receptor were obtained upon transfection of naïve CHO-K1 cells (ATCC CCL-61) with a mammalian expression vector carrying the whole coding sequence of human CXCR4 receptor (RefSeq NM_003467). Cells were propagated in complete culture medium [DMEM-Ham's F12 supplemented with 5% fetal calf serum (FCS) and 500 µg/ml of geneticin]. Cells were plated in black 96MW plates at a density of 100,000 cells/well in appropriate culture medium. Cells were starved overnight before conducting the experiments. Cells are loaded with the fluorescent calcium dye (Fluo-4 No Wash, Invitrogen US) in loading buffer [HBSS 1x, HEPES 20 mM, Probenicid acid 25 mM] for 30 min. at 37° C. followed by 30 min. at 25° C. Stimulation by SDF-1 was performed by direct injection into each well. For antagonism experiments, 10 µl of Mab solution are added directly into the loading buffer at least 10 min. before SDF-1. Kinetic fluorescence measurements are performed on a multi-mode fluorescence microplate reader Mithras LB940 (Berthold) using the following settings: excitation at 485 nm, emission at 535 nm, excitation energy at 10000 arbitrary units. Fluorescence in each well is recorded during 0.1 second every second and for a time period of 20 sec. prior SDF-1 injection (basal signal). Then 20 µl of SDF-1 are injected and data recording follows for a time period of 2 min. Each experimental condition is performed in duplicate. Values for each well are first corrected by subtracting the basal fluorescence and the fluorescence emitted by a control well without cells. Relative data are expressed as a percentage of the maximal stimulation obtained by SDF-1 (100 nM).

Figure 6C:
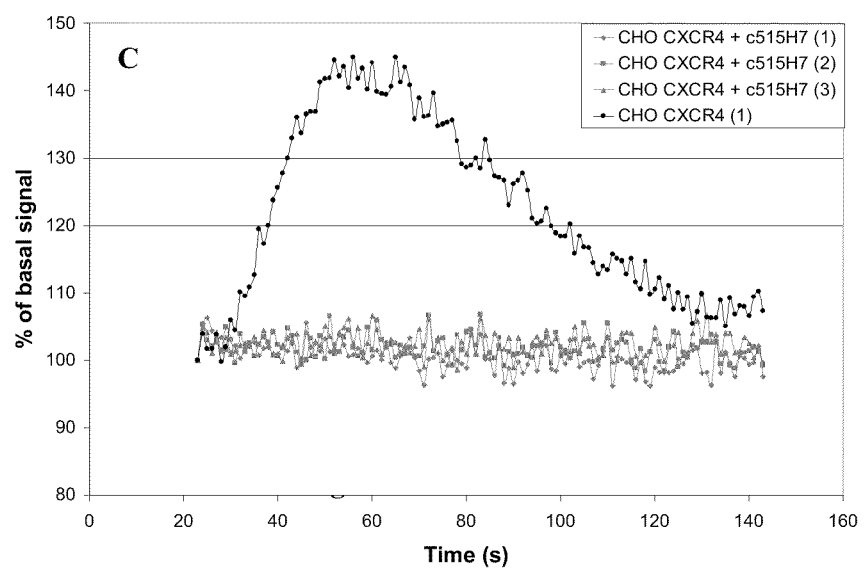

SDF1 (100 nM) induced a rapid and strong release of intracellular calcium in recombinant CHO/CXCR4, whereas no fluorescence signal was detected in naïve CHO-K1 cells. The maximal intensity reached >140% over basal fluorescence and was observed at about 40 sec. upon stimulation by SDF-1 (FIGS. 6A, 6B and 6C). Mabs 515H7 (133 nM) (FIG. 6A) and c515H7 (133 nM) (FIG. 6C) yielded a strong inhibition of the SDF-1 (100 nM)-induced calcium signal. Mab 301aE5 (133 nM) (FIG. 6B) yielded a partial inhibition of the SDF-1 (100 nM)-induced calcium signal.

Example 7

Inhibition of HIV-1 Primary Isolates KON, MN and 92UG024 (X4 Viruses) Replication in Human PBMC by Anti-CXCR4 Mabs 515H7, c515H7 and 301aE5

Single Cycle Neutralization Assay.

This assay is performed in 36 h using primary isolates KON, MN and 92UG024 concentrated and diluted accordingly to allow the detection 2% infected CD4 T lymphocytes after 2 days of infection.

Twenty-five microliters of various dilutions of Mabs 515H7, c515H7 and 301aE5 were incubated for 1 h at 37° C. with 25 µl of virus. Human PBMC (25 µl) at 20×10$^6$ cells/ml were added to the Mab/virus mixture in a 96-well plate (U-bottom, Costar 3599) and cultured for 36 h in RPMI 1640 10% FCS and 20 U/ml IL-2 (R&D Systems, Minneapolis, Minn.).

After 2 days of culture, HIV-infected lymphocytes were detected by intracellular staining of viral p24 Ag. Cells were fixed and permeabilized using both Cytofix/Cytoperm and Perm/Wash kits (BD Biosciences) according to the manufacturer and stained with a fluorescent anti-p24 Mab (FITC- or PE-anti-p24, clone KC57; Beckman Coulter/Immunotech, Hialeah, Fla.) used at a 1/160 dilution in Perm/Wash solution added for 15 min at 4° C. After washing in PBS with 3% FBS, PBMC were diluted in 300 µl of PBS before flow cytometry analysis (LSRII; BD Biosciences) with DIVA software (BD Biosciences). The percentage of p24-positive cells in the different samples was determined by gating 20,000 events on a living cell population identified by forward- and side-scatter parameters. The living cell subsets were analyzed with the live/dead solution kit (Invitrogen). The p24 Ag-positive value was obtained after subtraction of background events in mock-infected cells.

The percent of neutralization was defined as the reduction of p24-positive cells compared with control infected wells with no Mab. The neutralizing titer was defined as the concentration of antibody (interpolated between successive dilutions performed in triplicate) that allows a 90% decrease in the percentage of infected cells.

Figure 7:
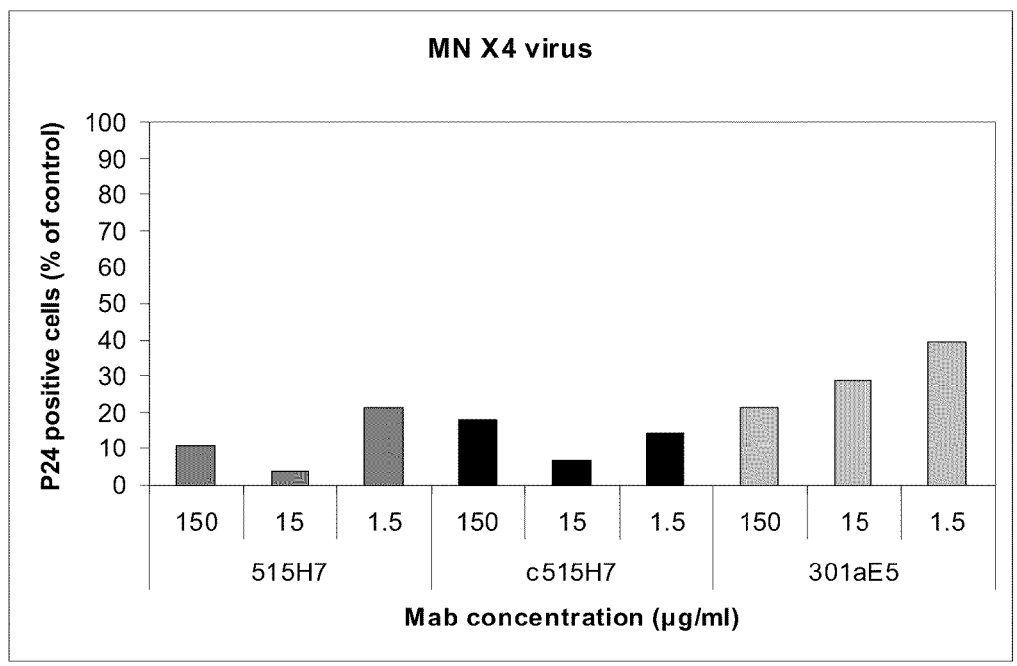
FIGS. 7 and 8 show the ability of anti-CXCR4 Mabs 515H7, c515H7 and 301aE5 to inhibit HIV-1 X4 virus primary isolates MN (FIG. 7) and 92UG024 (FIG. 8) replication in human PBMC.
Figure 8:
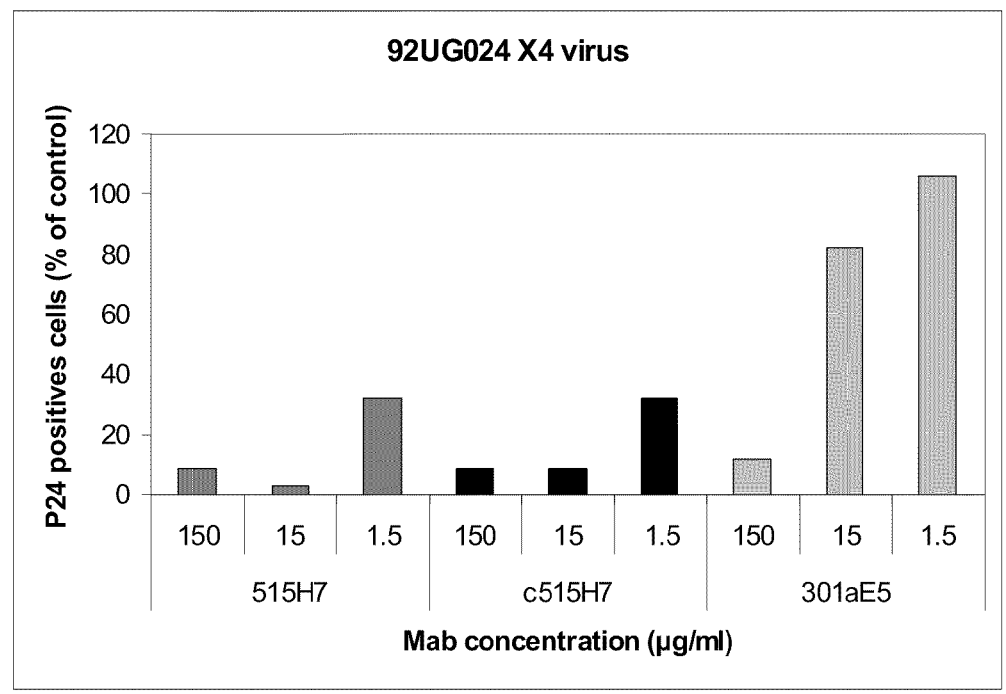
Figure 9:
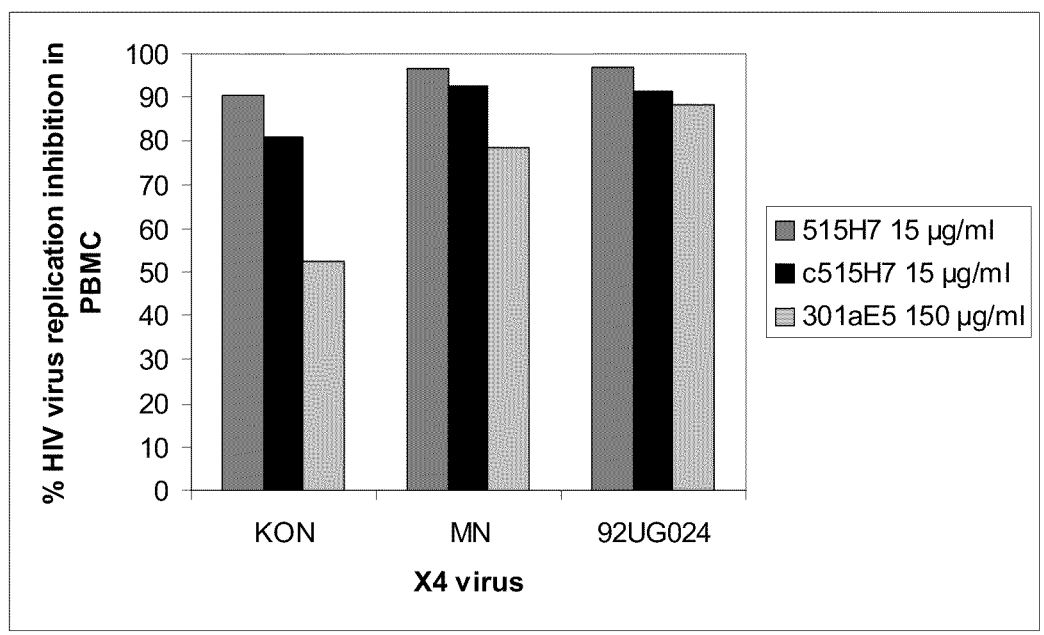
FIG. 9 shows the ability of anti-CXCR4 Mabs 515H7, c515H7 and 301aE5 to inhibit HIV-1 X4 virus primary isolates KON, MN and 92UGO24 replication in human PBMC.

As shown in FIGS. 7, 8 and 9, the anti-CXCR4 Mabs 515H7, c515H7 and 301aE5 are able to inhibit HIV-1 X4 MN, KON and 92UG024 primary isolates replication in PBMC. Results of ICs (in pg/ml) are summarized in table 9.

TABLE 9

| | KON % inhibition of infected cells | | | MN % inhibition of infected cells | | | 92UG024 % inhibition of infected cells | | |
|---|---|---|---|---|---|---|---|---|---|
| | 90 | 80 | 50 | 90 | 80 | 50 | 90 | 80 | 50 |
| 301aE5 | >150 | >150 | 150 | >150 | 150 | 1 | >150 | 150 | 50 |
| 515H7 | 15 | 8 | 1 | 10 | 1.5 | <1.5 | 10 | 3 | 0.5 |
| c515H7 | 20 | 10 | 1.5 | 15 | 1 | <1.5 | 15 | 3 | <1.5 |

Example 8

Inhibition of HIV-1 Primary Isolate 89.6 (Dual X4/R5 Virus) Replication in Human PBMC by Anti-CXCR4 Mabs 515H7, c515H7 and 301aE5

Single Cycle Neutralization Assay

This assay is performed in 36 h using primary isolate 89.6 concentrated and diluted accordingly to allow the detection 2% infected CD4 T lymphocytes after 2 days of infection.

Twenty-five microliters of various dilutions of Mabs 515H7, c515H7 and 301aE5 were incubated for 1 h at 37° C. with 25 µl of virus. Human PBMC (25 µl) at 20×10$^6$ cells/ml were added to the Mab/virus mixture in a 96-well plate (U-bottom, Costar 3599) and cultured for 36 h in RPMI 1640 10% FCS and 20 U/ml IL-2 (R&D Systems, Minneapolis, Minn.).

After 2 days of culture, HIV-infected lymphocytes were detected by intracellular staining of viral p24 Ag. Cells were fixed and permeabilized using both Cytofix/Cytoperm and Perm/Wash kits (BD Biosciences) according to the manufacturer and stained with a fluorescent anti-p24 Mab (FITC- or PE-anti-p24, clone KC57; Beckman Coulter/Immunotech, Hialeah, FL) used at a 1/160 dilution in Perm/Wash solution added for 15 min at 4° C. After washing in PBS with 3% FBS, PBMC were diluted in 300 µl of PBS before flow cytometry analysis (LSRII; BD Biosciences) with DIVA software (BD Biosciences). The percentage of p24-positive cells in the different samples was determined by gating 20,000 events on a living cell population identified by forward- and side-scatter parameters. The living cell subsets were analyzed with the live/dead solution kit (Invitrogen). The p24 Ag-positive value was obtained after subtraction of background events in mock-infected cells.

The percent of neutralization was defined as the reduction of p24-positive cells compared with control infected wells with no Mab. The neutralizing titer was defined as the concentration of antibody (interpolated between successive dilutions performed in triplicate) that allows a 90% decrease in the percentage of infected cells.

Figure 10:
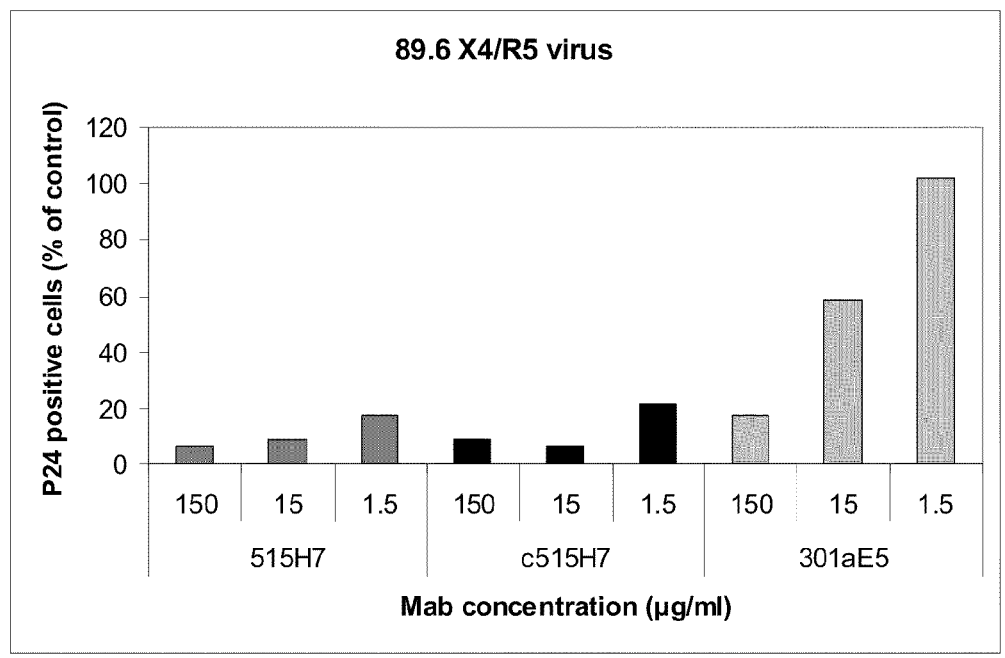
FIGS. 10 and 11 show the ability of anti-CXCR4 Mabs 515H7, c515H7 and 301aE5 to inhibit the dual HIV-1 X4/R5 virus primary isolate 89.6 replication in human PBMC.
Figure 11:
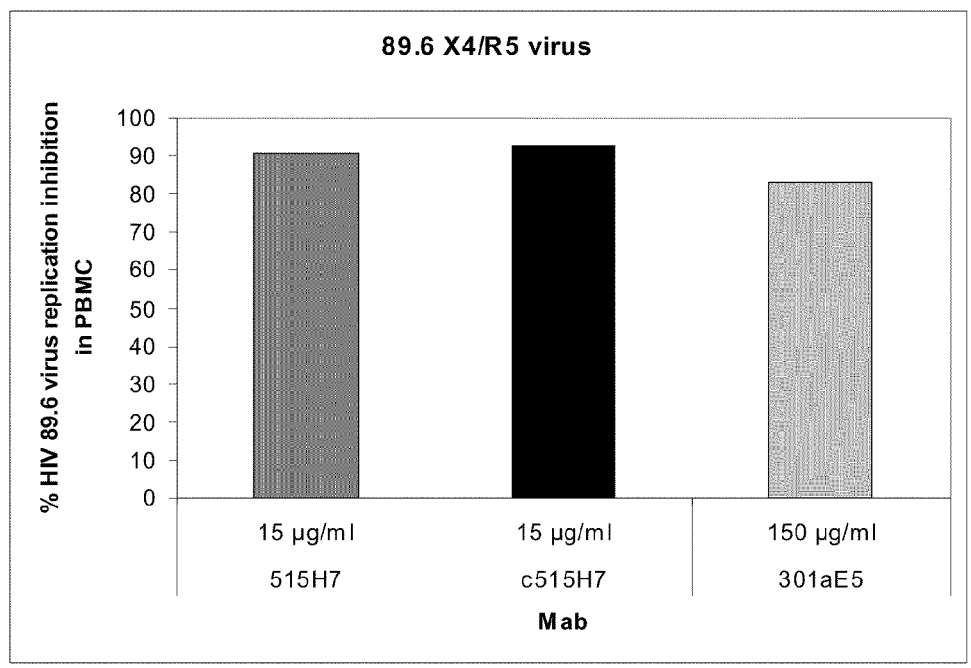

As shown in FIGS. 10 and 11, the anti-CXCR4 Mabs 515H7, c515H7 and 301aE5 are able to inhibit HIV-1 89.6 primary isolate replication in PBMC. Results of ICs (in µg/ml) are summarized in table 10.

TABLE 10

| | 89.6 % inhibition of infected cells | | |
|---|---|---|---|
| | 90 | 80 | 50 |
| 301aE5 | >150 | 150 | 20 |
| 515H7 | 15 | 1.5 | <1.5 |
| c515H7 | 10 | 1.5 | <1.5 |

Example 9

Inhibition of HIV-1 Primary Isolates 89.6 and UG93067 (Dual X4/R5 Viruses) Replication in Human PBMC by Anti-CXCR4 Mab c515H7 Combined with the Anti-CCR5 Molecule Maraviroc Neutralization Assay, Analyzing Multiple Round of HIV Primary Isolate Replication on Primary PBMC:

This assay that combines serial dilutions of c515H7 Mab or Maraviroc or combination of both with serial dilutions of virus, analyzes multiple rounds of infection on PBMC (peripheral blood mononuclear cells). Briefly, quadruplicate 25-µl aliquots of serial dilutions (twofold) of c515H7 Mabs or Maraviroc or combination of both were each incubated with 25 µl of serial dilutions of virus in prehydrated 96-well filter plates (1.25-µm pore size, Durapor Dv; Millipore, Molsheim, France). A control titration of the virus (25 µl of RPMI replacing the diluted c515H7 Mabs or Maraviroc) was performed on the same plate as the titrations in the presence of dilutions of the c515H7 Mabs or Maraviroc or combination of both. After 1 h at 37° C., 25 µl of PHA-stimulated PBMC at a concentration of $4 \times 10^6$ cells/ml (pool of PHA activated PBMC from five healthy donors) was added to achieve a 75-µl final culture volume of RPMI, 10% fetal calf serum (FCS), and 20 IU of interleukin-2 (IL-2) per ml (R&D System). After 24 h at 37° C., 100 µl of the same culture medium was added. Two washings (200 µl of RPMI each) were performed by filtration on day 4 to remove the c515H7 Mabs and Maraviroc, and 200 µl of fresh culture medium was added. On day 7, the presence of p24 in the culture supernatants was measured by ELISA and compared to that of the negative controls (cultures infected with dilutions of virus and maintained in the presence of $10^{-6}$ M zidovudine [AZT]) to determine positive wells. Quadruplicate wells were used to determine the viral titer (50% tissue culture infective dose [$TCID_{50}$]) in the absence ($V_0$) and in the presence ($V_n$) of each dilution of the c515H7 Mabs or Maraviroc or combination of both. The neutralizing titer was defined as the dilution of c515H7 Mabs or Maraviroc or combination of both resulting in a 90% decrease of the viral titer ($V_n/V_0=0.1$).

Figure 12:
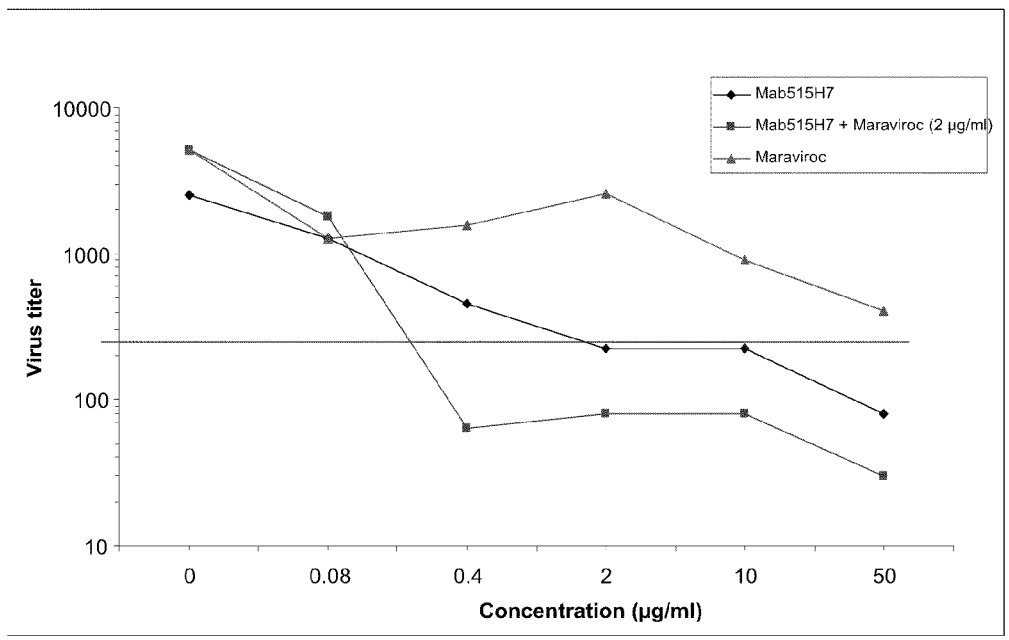
FIG. 12 shows the beneficial effect of combining Mab c515H7 with Maraviroc to inhibit HIV-1 primary isolate 89.6 (dual X4/R5 virus) replication in human PBMC.

As shown in FIG. 12, the dual tropic X4R5 virus 89.6 replication was inhibited by c515H7 Mabs with an $IC_{90}$ of 2 µg/ml (FIG. 12). Maraviroc at 50 µg/ml did not reach the $IC_{90}$ inhibitory activity (FIG. 12). Moreover, addition of Maraviroc at 2 µg/ml to antibody 515H7 augmented the inhibitory activity of the c515H7 Mabs with an $IC_{90}$ of 0.2 µg/ml (FIG. 12).

Figure 13:
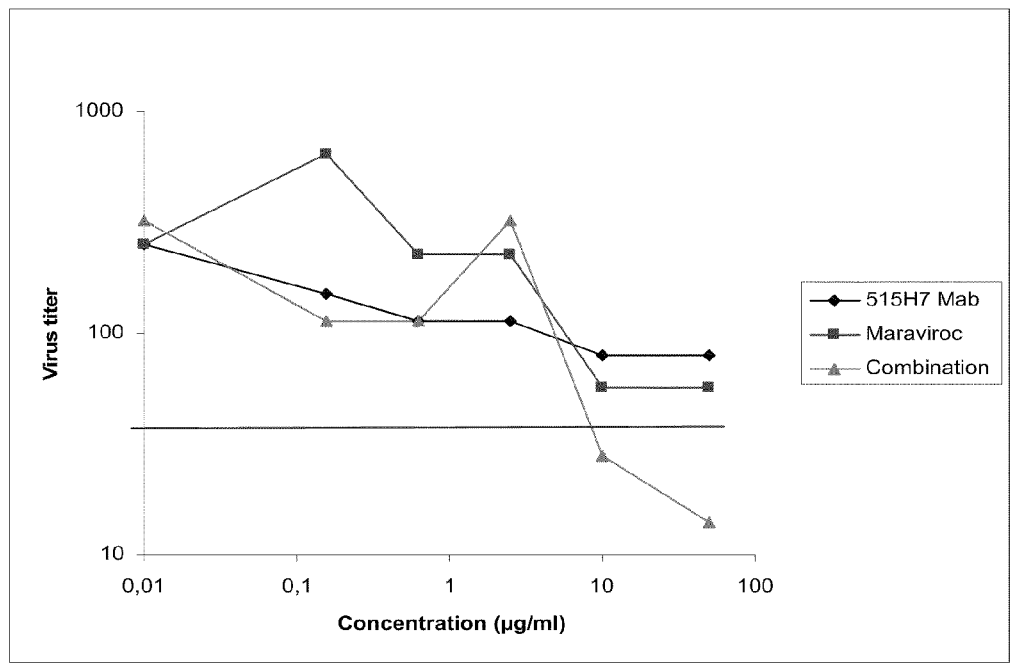
FIG. 13 shows the beneficial effect of combining Mab c515H7 with Maraviroc to inhibit HIV-1 primary isolate UG93067 (dual X4/R5 virus) replication in human PBMC.
Figure 14:
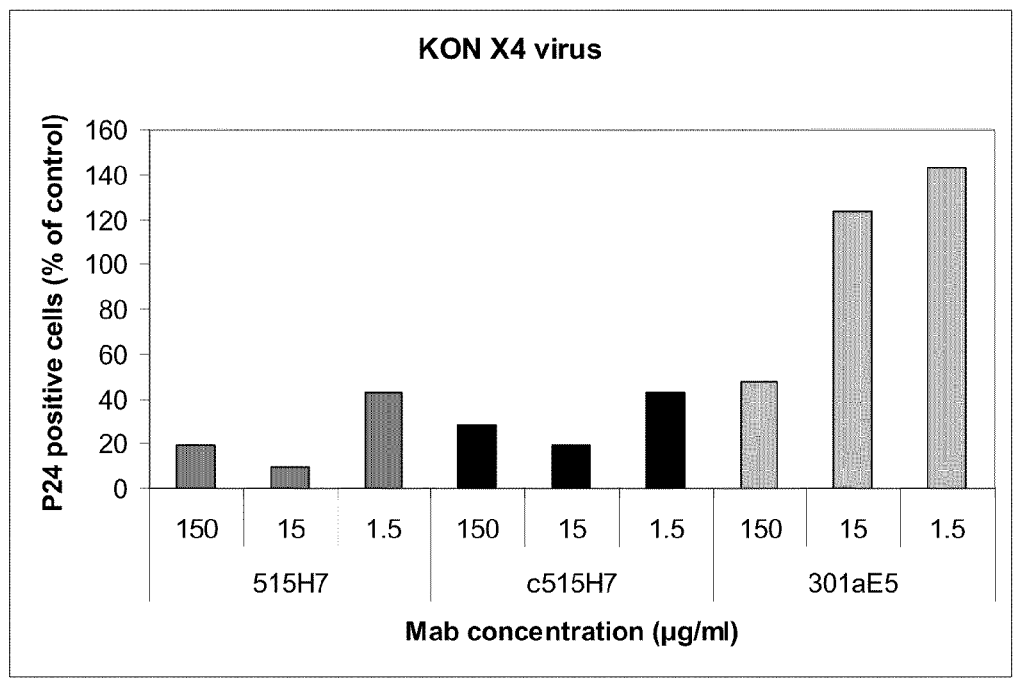
FIG. 14 shows the ability of anti-CXCR4 Mabs 515H7, c515H7 and 301aE5 to inhibit HIV-1 X4 virus primary isolate KON replication in PBMC.

The beneficial effect of c515H7 Mabs and Maraviroc combination was assessed using various dilutions of the two molecules and another dual tropic virus UG93067. As shown in FIG. 13, the inhibitory activity of Mabs c515H7 and Maraviroc was similar. These results suggest that the capacity of virus UG93067 to use either CCR5 or CXCR4 receptor was comparable. Using the UG93067 virus, a better activity could be evidenced, only the combination of these X4 (c515H7 Mabs) and R5 (Maraviroc) inhibitors (10 µg/ml of each) allowed a 90% reduction of virus titer (FIG. 13).

Example 10

Production of Anti-CXCR4 Chimeric Mab c515H7

Chimeric format of murine 515H7 Mab was designed: it corresponds to the light and heavy chain variable domains of the murine antibody of interest, genetically fused to human Ckappa and IgG1/IgG2/IgG4 constant domains. The recombinant Mab were produced upon transient transfection by using the HEK293/EBNA system with a pCEP4 expression vector (InVitrogen, US).

Respective amino acid and nucleotide sequences were described above in the specification. Moreover, as the above table 3 discloses the sequences of the IgG2 and 4 isotypes (which are preferred isotypes), it can also be mentioned here the sequence of the heavy chain of the IgG1 isotype, i.e. c515H7 VH (G1wt) which corresponds to the amino acid sequence SEQ ID No. 80 and the nucleotide sequence SEQ ID No.81.

The entire nucleotide sequences corresponding to the variable domains of 515H7 Mab light and heavy chains were synthesized by global gene synthesis (Genecust, Luxembourg). They were subcloned into a pCEP4 vector (InVitrogen, US) carrying the entire coding sequence of the constant domain of either the light [Ckappa] or the heavy [CH1-Hinge-CH2-CH3] chain of a human IgG1/IgG2/IgG4 immunoglobulin. All cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Biosystems, US).

Suspension-adapted HEK293 EBNA cells (InVitrogen, US) were routinely grown in 250 ml flasks in 50 ml of serum-free medium Excell 293 (SAFC Biosciences) supplemented with 6 mM glutamine on an orbital shaker (110 rpm rotation speed). Transient transfection was performed with $2.10^6$ cells/ml using linear 25 kDa polyethyleneimine (PEI) (Polysciences) prepared in water at a final concentration of 1 mg/ml mixed and plasmid DNA (final concentration of 1.25 µg/ml for heavy to light chain plasmid ratio of 1:1). At 4 hours post-transfection, the culture was diluted with one volume of fresh culture medium to achieve a final cell density of $10^6$cells/ml. Cultivation process was monitored on the basis of cell viability and Mab production. Typically, cultures were maintained for 4 to 5 days. Mab was purified using a conventional chromatography approach on a Protein A resin (GE Healthcare, US). Mab was produced at levels suitable with functional evaluations. Productivity levels are typically ranging between 6 and 15 mg/l of purified Mab.

Example 11

Characterization of Anti-CXCR4 Chimeric Mab c515H7 Binding Specificity by FACS Analysis In this experiment, specific binding to human CXCR4 of anti-CXCR4 chimeric Mab c515H7 was examined by FACS analysis.

Figure 15:
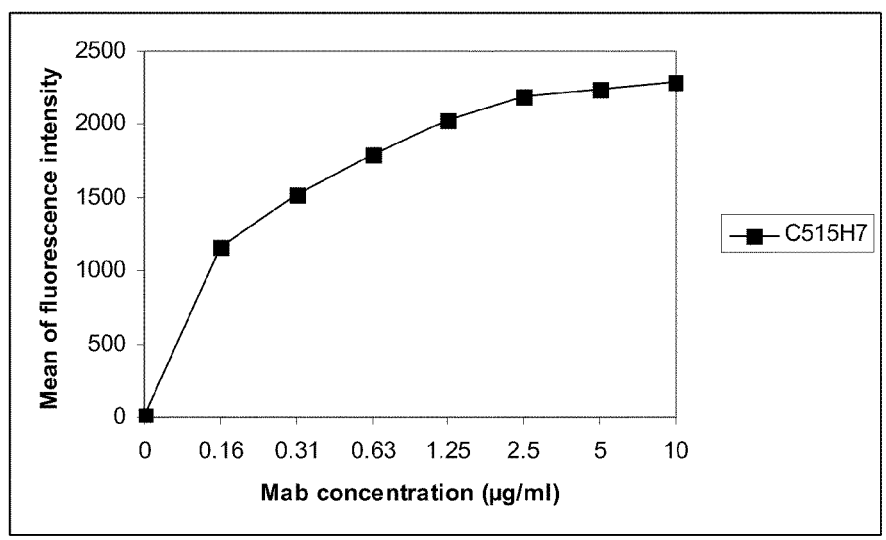
FIG. 15 illustrates the binding specificity of the c515H7 Mab by FACS analysis.

NIH3T3-hCXCR4 transfected cells were incubated with a dose range of monoclonal antibody c515H7 from 0 µg/ml to 10 µg/ml. The cells were then washed with 1%BSA/PBS/ 0.01% NaN3. Next, Alexa-labeled secondary antibodies were added to the cells and were allowed to incubate at 4° C. for 20 min. The cells were then washed again two times. Following the second wash, FACS analysis was performed. Results of this binding study are provided in FIG. 15 which shows that anti-CXCR4 chimeric Mab c515H7 bound specifically to human CXCR4-NIH3T3 transfected cell line. No binding was detected to NIH3T3 wt cells (data not shown).

Example 12

Effect of c515H7 Mab on CXCR4 Homodimer, by Bioluminescence Resonance Energy Transfer (BRET) Approach This functional assay allows to evaluate the conformational changes induced upon SDF-1 and/or c515H7 Mab binding to CXCR4 receptor at the level of CXCR4 homodimer.

Expression vectors for the investigated interaction partners were constructed as fusion proteins with the corresponding dye (*Renilla reniformis* luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4/Rluc+CXCR4/YFP] to study CXCR4 homodimerization. The day after, cells were distributed in poly-lysine pre-coated white 96 MW plates in complete culture medium [DMEM supplemented with 10% FBS]. Cells were first cultivated at 37° C. with $CO_2$ 5% in order to allow cell attachment to the plate. Cells were then starved with 200 μl DMEM/well overnight Immediately prior to the BRET experiment, DMEM was removed and cells were quickly washed with PBS. Cells were then incubated in PBS in the presence or absence of antibody, 10 min at 37° C. prior to the addition of coelenterazine H 5 μM with or without SDF-1 100 nM in a final volume of 50 μl. After incubation for further 10 minutes at 37° C., light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): $[(emission_{530\ nm})-(emission_{485\ nm})\times Cf]/(emission_{485\ nm})$, where $Cf=(emission_{530\ nm})/(emission_{485\ nm})$ for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed in milliBRET units (mBU); mBU corresponds to the BRET ratio multiplied by 1000.

Figure 16:
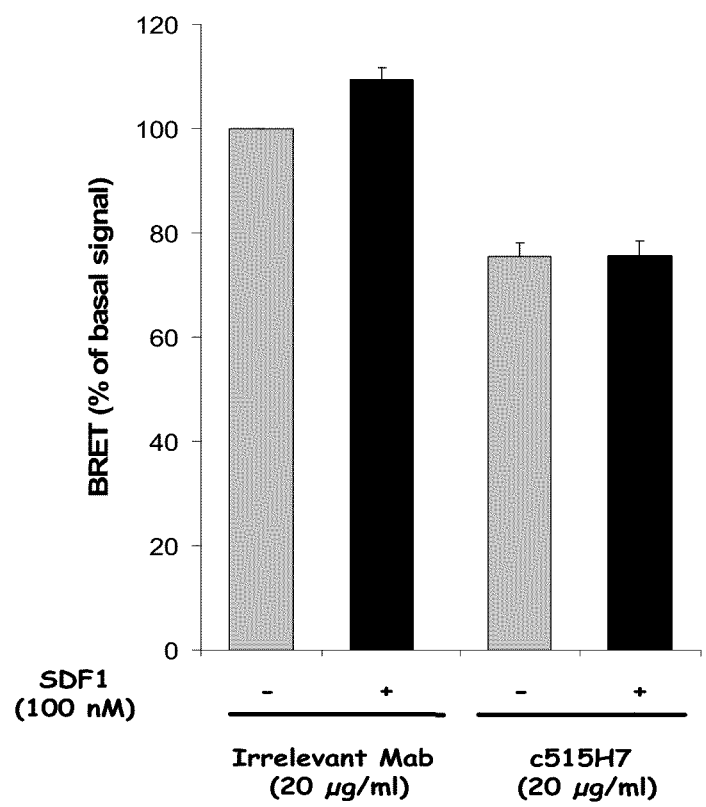
FIG. 16 illustrates the effect of c515H7 Mab on CXCR4 homodimer, by bioluminescence resonance energy transfer (BRET) approach.

SDF1 (100 nM) increased by about 10% the BRET signal resulting from the spatial proximity of the donor and acceptor proteins fused to CXCR4 receptor, it is likely to indicate CXCR4/CXCR4 homo-dimers formation or conformational changes of pre-existing dimers (FIG. 16). Mab c515H7 was able to modulate SDF-1-induced conformational changes for CXCR4 homo-dimers (96% inhibition of SDF-1-induced BRET increase, FIG. 16). Mab c515H7 was also able to modulate by itself CXCR4/CXCR4 spatial proximity, indicating an influence of this Mab on CXCR4/CXCR4 homodimer conformation (FIG. 16).

Example 13

In Vitro Evaluation of Mab 515H7 Anti-HIV-1 Activity Using GFP-Transduced Human Osteosarcoma (GHOST) Cells Expressing CD4 and CXCR4 or CCR5

In order to determine the specificity of CXCR4 515H7 Mab, we evaluated the anti-HIV-1 activity of this Mab using GHOST cells expressing CD4 and CXCR4 or CCR5.

This assay is performed in 48 h using either the X4 HIV-1 LAI virus (with Ghost cells expressing CXCR4) or the R5 HIV-1 BaL virus (with Ghost cells expressing CCR5). 500 μl of Ghost cells were plated (2.5 $10^5$ cells/ml) for 24 h in Dulbecco culture medium supplemented with 10% FCS. Various dilutions of Mab 515H7 were incubated for 1 h at 37° C. and then diluted HIV-1 LAI virus (1/10) and HIV-1 BaL virus (1/7) were added to the cells for 48h. Cells were submitted to trypsin and washed with PBS 1×. 300 μL of 1.5% paraformaldehyde were added to the cell pellets for 2 h at +4° C. in the dark, in order to fix the cells and to inactivate viruses. GFP-positive cells were analyzed by flow cytometry and inhibition of HIV-1 infection was calculated.

The percent of inhibition of infected cells was defined as the compared with control infected wells with no Mab. Results of ICs (in μg/ml) are summarized in table 11, the anti-CXCR4 Mab 515H7 was able to inhibit HIV-1 X4 Lai virus infection in CXCR4 expressing Ghost cells but was totally inactive in inhibiting HIV-1 R5 BaL virus infection in CCR5 expressing Ghost cells.

TABLE 11

|  | GHOST CXCR4/LAI virus % inhibition of infected cells | | | GHOST CCR5/BaL virus % inhibition of infected cells | | |
| --- | --- | --- | --- | --- | --- | --- |
|  | 90 | 80 | 50 | 90 | 80 | 50 |
| 515H7 | 0.5 | 0.1 | 0.08 | >75 | >75 | >75 |

Example 14

Humanization of 515H7 Anti-CXCR4 Murine Antibody and Generation of a Fragment of said h515H7

General Procedure

Humanization of 515H7 anti-CXCR4 antibody was performed by applying the global rules of CDR-grafting. Immunogenetic analysis and definition of CDR and framework (FR) regions were performed by applying the IMGT unique numbering scheme as well as the IMGT libraries and tools (Lefranc, 1997—IMGT database at www dot IMGT dot org).

Binding of humanized variants of 515H7 was determined on a NIH3T3 cell line stably transfected with human CXCR4. The binding activity was evaluated by a competition assay with the biotinylated mouse antibody. In a second attempt, humanized antibodies were evaluated for their ability to inhibit binding of biotinylated SDF-1 to RAMOS cells. RAMOS cells were chosen because of their high expression of CXCR4 and low expression of CXCR7 and SDF-1.

These assays were used to characterize the recombinant humanized versions of anti-CXCR4 antibodies. Variable domains were formatted with human IgG1/k constant domains and cloned into the mammalian expression vector pCEP. Recombinant $IgG_1/\kappa$-derived antibodies were transiently expressed in HEK293 cells. Expression culture supernatants were filtered and antibodies were purified using protein A sepharose. Purified antibodies were rebuffered in PBS and antibodies concentrations determined by ELISA.

Recombinants antibody fragments were generated by PCR using oligonucleotides specific for the variable domains of the humanized antibody and subcloning these into an *E. coli* system. Purification of antibody fragments was done by immobilized metal ion affinity chromatography (IMAC).

Humanization of 515H7 Variable Domains

The different sequences alignments of the heavy and light chains variable domains are illustrated in FIGS. 17 and 18.

In a first series of experiments, the anti-CXCR4 binding activities of the three first humanized variants were analysed. The VH variant 1 (VH1) was combined with the murine VL and these constructs were evaluated in their capacity to inhibit the binding of a biotinylated murine 515H7 parental antibody. The amino acid sequence of the variable domain of VH1 comprises the SEQ ID No. 90 whereas the nucleotide sequence comprises the SEQ ID No. 91. The amino acid sequence of the full length VH1 comprises the SEQ ID No. 92 whereas the nucleotide sequence comprises the SEQ ID No. 93. This construct showed similar capacity to compete with the murine antibody as the chimeric antibody (FIG. 19A). This indicates that the most human VH variant has the same binding capacity as chimeric. Therefore, VH1 was combined with the variant 2 of VL (FIG. 19B).

In further experiments, it has been determined whether humanized variants of the antibody 515H7 inhibit the binding of SDF-1 to CXCR4 expressing cells (FIG. 20). The inhibitory capacity of humanized variants of hz515H7 was evaluated by detecting biotinylated SDF-1 in flow cytometry. The humanized antibody hz515H7 VH1 D76N VL2 has a similar capacity to inhibit SDF-1 binding as the chimeric c515H7.

An antibody fragment of the humanized variant hz515H7 VH1 VL2 has also been tested and it has been determined that said antibody fragment is able to completely inhibit the binding of SDF-1 (FIG. 20).

Example 15

Characterization by FACS Analysis of Anti-CXCR4 Humanized Mabs 515H7 Binding Specificity In this experiment, specific binding to human CXCR4 of anti-CXCR4 humanized Mabs 515H7 was examined by FACS analysis.

NIH3T3, NIH3T3-hCXCR4 transfected were incubated with 0 to 10 µg/mL of humanized Mabs 515H7 (hz515H7 VH1 D76N VL2, hz515H7 VH1 D76N VL2.1, hz515H7 VH1 D76N VL2.2, hz515H7 VH1 D76N VL2.3) for 20 min at 4° C. in the dark in 100 µl Facs buffer. After 3 washing in Facs buffer, cells were incubated with the secondary antibody, a goat anti-human Alexa 488 (dilution 1/500), for 20 minutes at 4° C. in the dark. After 3 washing in Facs buffer, propidium iodide was added in each well and only viable cells were analyzed by Facs. At least 5000 viable cells were assessed to evaluate the mean value of fluorescence intensity for each condition.

Results of these binding studies are provided in FIG. 21 which shows [Mean Fluorescence Intensity (MFI) obtained by FACS] that anti-CXCR4 humanized Mabs hz515H7 bound specifically to human CXCR4-NIH3T3 transfected cell line (MFI=2.2 with NIH3T3 parent cells)

Example 16

Effect of hz515H7 Mabs on CXCR4 Homodimer, by Bioluminescence Resonance Energy Transfer (BRET) Approach This functional assay allows to evaluate the conformational changes induced upon SDF-1 and/or hz515H7 VH1 D76N VL2, hz515H7 VH1 D76N VL2.1, hz515H7 VH1 D76N VL2.2, hz515H7 VH1 D76N VL2.3 binding to CXCR4 receptor at the level of CXCR4 homodimer.

Expression vectors for the investigated interaction partners were constructed as fusion proteins with the corresponding dye (*Renilla reniformis* luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4/Rluc+CXCR4/YFP] to study CXCR4 homodimerization. The day after, cells were distributed in poly-lysine pre-coated white 96 MW plates in complete culture medium [DMEM supplemented with 10% FBS]. Cells were first cultivated at 37° C. with $CO_2$ 5% in order to allow cell attachment to the plate. Cells were then starved with 200 µl DMEM/well overnight Immediately prior to the BRET experiment, DMEM was removed and cells were quickly washed with PBS. Cells were then incubated in PBS in the presence or absence of antibody, 10 min at 37° C. prior to the addition of coelenterazine H 5 µM with or without SDF-1 100 nM in a final volume of 50 µl. After incubation for further 10 minutes at 37° C., light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): $[(emission_{530\ nm})-(emission_{485\ nm}) \times Cf]/(emission_{485\ nm})$, where $Cf=(emission_{530\ nm})/(emission_{485\ nm})$ for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed in milliBRET units (mBU); mBU corresponds to the BRET ratio multiplied by 1000.

SDF1 (100 nM) increased by about 12% the BRET signal resulting from the spatial proximity of the donor and acceptor proteins fused to CXCR4 receptor, it is likely to indicate CXCR4/CXCR4 homo-dimers formation or conformational changes of pre-existing dimers (FIG. 22).

515H7 humanized Mabs were able to modulate SDF-1-induced conformational changes for CXCR4 homo-dimers with a percentage of inhibition of SDF-1-induced BRET increase of about 88% for hz515H7 VH1D76N-VL2 Mab, 65% for hz515H7 VH1D76N-VL2.1 Mab, 33% for hz515H7 VH1D76N-VL2.2 Mab and 21% for hz515H7 VH1D76N-VL2.3 Mab (FIG. 22)

Example 17

Inhibition of HIV-$1_{lm}$ (X4 Virus) Replication in MT-4 Cells by Anti-CXCR4 Mab hz515H7

In this assay, the activity of hz515H7 Mab against HIV-$1_{IIIB}$ was based on the inhibition of virus-induced cytopathogenicity in MT-4 cells. Cells were infected with HIV-$1_{IIIB}$ isolate at 5 times the tissue culture infective dose 50 ($TCID_{50}$) a virus dose which decreases the number of viable cells by 90% within 5 days. After adsorption at 37° C. for 30 min, infected cells were adjusted to $2\ 10^5$ cells/ml in RPMI 1640 medium supplemented with 20% heat-inactivated fetal calf serum (FCS), 100 IU/ml penicillin, 100 µg/ml streptomycin, 2 mM glutamine and seeded in 96-well flat-bottom tissue culture plates (COSTAR 3596) (100 µl/well) with 100 µl of the hz515H7 Mab at various concentrations. On day 5, cell viability was measured with the colorimetric reaction MTT.

The percentage of protection of infected cells treated with the hz515H7 Mab was calculated according to the following formula:

$$\% \text{ Protection} = \frac{[OD_{540} \text{ of infected cells treated with } hz515H7 \text{ Mab}] - [OD_{540} \text{ of control-infected cells}]}{[OD_{540} \text{ of control-uninfected cells}] - [OD_{540} \text{ of control-infected cells}]}$$

As shown in FIG. 23, hz515H7 Mab displays a marked anti-HIV-1 activity since it was able to inhibit HIV-1$_{IIIB}$—induced cytopathogenicity in MT-4 cells.

Example 18

Inhibition of HIV-1 Primary Isolate KON (X4 Virus) Replication in Human PBMC by Anti-CXCR4 Mab hz515H7

Single Cycle Neutralization Assay.

This assay was performed in 36 h using primary isolate KON concentrated and diluted accordingly to allow the detection 2% infected CD4 T lymphocytes after 2 days of infection.

Twenty-five microliters of various dilutions of Mab hz515H7 were incubated for 1 h at 37° C. with 25 µl of virus. Human PBMC (25 p.1) at 20×10$^6$ cells/ml were added to the Mab/virus mixture in a 96-well plate (U-bottom, Costar 3599) and cultured for 36 h in RPMI 1640 10% FCS and 20 U/ml IL-2 (R&D Systems, Minneapolis, Minn.).

After 2 days of culture, HIV-infected lymphocytes were detected by intracellular staining of viral p24 Ag. Cells were fixed and permeabilized using both Cytofix/Cytoperm and Perm/Wash kits (BD Biosciences) according to the manufacturer and stained with a fluorescent anti-p24 Mab (FITC- or PE-anti-p24, clone KC57; Beckman Coulter/Immunotech, Hialeah, Fla.) used at a 1/160 dilution in Perm/Wash solution added for 15 min at 4° C. After washing in PBS with 3% FBS, PBMC were diluted in 300 µl of PBS before flow cytometry analysis (LSRII; BD Biosciences) with DIVA software (BD Biosciences). The percentage of p24-positive cells in the different samples was determined by gating 20,000 events on a living cell population identified by forward- and side-scatter parameters. The living cell subsets were analyzed with the live/dead solution kit (Invitrogen). The p24 Ag-positive value was obtained after subtraction of background events in mock-infected cells.

The percent of neutralization was defined as the reduction of p24-positive cells compared with control infected wells with no Mab. The neutralizing titer was defined as the concentration of antibody (interpolated between successive dilutions performed in triplicate) that allows a decrease in the percentage of infected cells.

As shown in FIG. 24, the anti-CXCR4 Mab hz515H7 is able to inhibit HIV-1 X4 KON primary isolate replication in PBMC.

Example 19

Inhibition of HIV-1 Primary Isolates 89.6 and UG93067 (Dual X4/R5 Viruses) Replication in Human PBMC by Anti-CXCR4 Mab hz515H7 Combined with the Anti-CCR5 Molecule Maraviroc Neutralization Assay, Analyzing Multiple Round of HIV Primary Isolate Replication on Primary PBMC:

This assay that combines serial dilutions of hz515H7 Mab or Maraviroc or combination of both with serial dilutions of virus, analyzes multiple rounds of infection on PBMC (peripheral blood mononuclear cells). Briefly, quadruplicate 25-µl aliquots of serial dilutions (twofold) of hz515H7 Mab or Maraviroc or combination of both were each incubated with 25 µl of serial dilutions of virus in prehydrated 96-well filter plates (1.25-µm pore size, Durapor Dv; Millipore, Molsheim, France). A control titration of the virus (25 µl of RPMI replacing the diluted hz515H7 Mab or Maraviroc) was performed on the same plate as the titrations in the presence of dilutions of the hz515H7 Mab or Maraviroc or combination of both. After 1 h at 37° C., 25 µl of PHA-stimulated PBMC at a concentration of 4×10$^6$ cells/ml (pool of PHA activated PBMC from five healthy donors) was added to achieve a 75-µl final culture volume of RPMI, 10% fetal calf serum (FCS), and 20 IU of interleukin-2 (IL-2) per ml (R&D System). After 24 h at 37° C., 100 µl of the same culture medium was added. Two washings (200 µl of RPMI each) were performed by filtration on day 4 to remove the hz515H7 Mab and Maraviroc, and 200 µl of fresh culture medium was added. On day 7, the presence of p24 in the culture supernatants was measured by ELISA and compared to that of the negative controls (cultures infected with dilutions of virus and maintained in the presence of 10$^{-6}$ M zidovudine [AZT]) to determine positive wells. Quadruplicate wells were used to determine the viral titer (50% tissue culture infective dose [TCID$_{50}$]) in the absence ($V_0$) and in the presence ($V_n$) of each dilution of the 515H7 Mab or Maraviroc or combination of both. The neutralizing titer was defined as the dilution of 515H7 Mab or Maraviroc or combination of both resulting in a 90% decrease of the viral titer ($V_n/V_0$=0.1).

The possible synergy between hz515H7 Mab and Maraviroc was assessed using a combination of various dilutions of the two molecules using dual tropic viruses 89.6 and UG93067. As shown in FIGS. 25 and 26, the inhibitory activity of Mab hz515H7 and Maraviroc was similar. The combination of these X4 (hz515H7 Mab) and R5 (Maraviroc) inhibitors allowed a 90% reduction of 89.6 and UG93067 dual X4/R5 virus titers in PBMC (FIGS. 25 and 26, respectively).

The invention claimed is:

1. A recombinant anti-CXCR4 antibody or a CXCR4-binding fragment thereof, wherein said antibody or binding fragment comprises a light chain comprising CDR-L1, CDR-L2 and CDR-L3 comprising respectively the amino acid sequence of SEQ ID Nos. 1, 2 and 30; and a heavy chain comprising CDR-H1, CDR-H2 and CDR-H3 comprising respectively the amino acid sequence of SEQ ID Nos. 31, 32 and 33.

2. The antibody of claim 1, or a CXCR4-binding fragment thereof, wherein said antibody or binding fragment comprises a light chain comprising the amino acid sequence of SEQ ID No. 34 and a heavy chain comprising the amino acid sequence of SEQ ID No. 35.

3. A composition comprising the antibody or binding fragment thereof according to one of claims 1 and 2, and a pharmaceutically acceptable excipient and/or a pharmaceutically acceptable carrier.

4. A composition comprising a binding fragment according to one of claims 1 and 2, and further comprising a pharmaceutically acceptable excipient and/or a pharmaceutically acceptable carrier.

5. A composition comprising the antibody or binding fragment according to claim 1, and a pharmaceutically acceptable excipient and/or a pharmaceutically acceptable carrier.

6. A composition comprising the antibody or binding fragment according to claim 2, and a pharmaceutically acceptable excipient and/or a pharmaceutically acceptable carrier.

7. The composition according to claim 4, further comprising a second anti-HIV compound selected among compounds capable of specifically inhibiting HIV entry and/or replication.

8. The composition according to any one of claims 5 and 6, further comprising a second anti-HIV compound selected among compounds capable of specifically inhibiting HIV entry and/or replication.

9. The composition according to claim 8, wherein said second anti-HIV compound is chosen from HIV protease inhibitors (PI), nucleoside /nucleotide HIV reverse-transcriptase inhibitors (NRTI/NtRTI), non-nucleoside HIV reverse-transcriptase inhibitors (NNRTI), HIV entry inhibitors, and HIV integrase inhibitors.

10. The composition according to claim 8, wherein said second anti-HIV compound is an anti-CCR5 compound.

11. The composition according to claim 10, wherein said anti-CCR5 compound is Maraviroc.

12. The composition of claim 4 further comprising a second anti-HIV agent, wherein the second anti-HIV agent is chosen from HIV protease inhibitors (PI), nucleoside /nucleotide HIV reverse-transcriptase inhibitors (NRTI/NtRTI), non-nucleoside HIV reverse-transcriptase inhibitors (NNRTI), HIV entry inhibitors, and HIV integrase inhibitors.

13. The antibody of claim 1, or a CXCR4-binding fragment thereof, wherein the antibody is humanized.

14. The antibody according to any one of claims 1 and 2, or a CXCR4-binding fragment thereof, wherein the antibody is chimeric.

15. The antibody of claim 13, or a CXCR4-binding fragment thereof, wherein the fragment is chosen from Fv, scFv, Fab, F(ab')$_2$, Fab', and scFv-Fc fragments.

16. The antibody of claim 14, or a CXCR4-binding fragment thereof, wherein the fragment is chosen from Fv, scFv, Fab, F(ab')$_2$, Fab', and scFv-Fc fragments.

17. A composition comprising the antibody according to any one of claims 13 and 15, or a CXCR4-binding fragment thereof, and a pharmaceutically acceptable excipient and/or a pharmaceutically acceptable carrier.

18. A composition comprising the antibody according to claim 14, or a CXCR4-binding fragment thereof, and a pharmaceutically acceptable excipient and/or a pharmaceutically acceptable carrier.

19. A composition comprising the antibody according to claim 16, or a CXCR4-binding fragment thereof, and a pharmaceutically acceptable excipient and/or a pharmaceutically acceptable carrier.

20. The composition according to claim 17, further comprising a second anti-HIV compound selected among the compounds capable of specifically inhibiting HIV entry and/or replication.

21. The composition according to claim 20, wherein said second anti-HIV compound is chosen from HIV protease inhibitors (PI), nucleoside /nucleotide HIV reverse-transcriptase inhibitors (NRTI/NtRTI), non-nucleoside HIV reverse-transcriptase inhibitors (NNRTI), HIV entry inhibitors, and HIV integrase inhibitors.

22. The composition according to claim 20, wherein said second anti-HIV compound is an anti-CCR5 compound.

23. The composition according to claim 22, wherein said anti-CCR5 compound is Maraviroc.

24. The composition according to claim 18, further comprising a second anti-HIV compound selected among the compounds capable of specifically inhibiting HIV entry and/or replication.

25. The composition according to claim 24, wherein said second anti-HIV compound is chosen from HIV protease inhibitors (PI), nucleoside /nucleotide HIV reverse-transcriptase inhibitors (NRTI/NtRTI), non-nucleoside HIV reverse-transcriptase inhibitors (NNRTI), HIV entry inhibitors, and HIV integrase inhibitors.

26. The composition according to claim 24, wherein said second anti-HIV compound is an anti-CCR5 compound.

27. The composition according to claim 26, wherein said anti-CCR5 compound is Maraviroc.

28. The composition according to claim 19, further comprising a second anti-HIV compound selected among the compounds capable of specifically inhibiting HIV entry and/or replication.

29. The composition according to claim 28, wherein said second anti-HIV compound is chosen from HIV protease inhibitors (PI), nucleoside /nucleotide HIV reverse-transcriptase inhibitors (NRTI/NtRTI), non-nucleoside HIV reverse-transcriptase inhibitors (NNRTI), HIV entry inhibitors, and HIV integrase inhibitors.

30. The composition according to claim 28, wherein said of second anti-HIV compound is an anti-CCR5 compound.

31. The composition according to claim 30, wherein said anti-CCR5 compound is Maraviroc.

32. A monoclonal antibody, or CXCR4-binding fragment thereof, wherein said antibody comprises a light chain comprising CDR-L1, CDR-L2 and CDR-L3 comprising respectively the amino acid sequence of SEQ ID Nos. 1, 2 and 30; and a heavy chain comprising CDR-H1, CDR-H2 and CDR-H3 comprising respectively the amino acid sequence of SEQ ID Nos. 31, 32 and 33.

33. The antibody of claim 32, or a CXCR4-binding fragment thereof, wherein said antibody or binding fragment comprises a light chain comprising the amino acid sequence of SEQ ID No. 34 and a heavy chain comprising the amino acid sequence of SEQ ID No. 35.

34. A composition comprising the antibody according to one of claims 32 and 33, or a binding fragment thereof, and a pharmaceutically acceptable excipient and/or a pharmaceutically acceptable carrier.

35. A composition comprising by way of active principle a compound consisting of an antibody according to one of claims 32 and 33, or a CXCR4-binding fragment thereof, and further comprising a pharmaceutically acceptable excipient and/or a pharmaceutically acceptable carrier.

36. A composition comprising the antibody according to claim 32, or a CXCR4-binding fragment thereof, and a pharmaceutically acceptable excipient and/or a pharmaceutically acceptable carrier.

37. The antibody according to claim 32, or a CXCR4-binding fragment thereof, wherein the antibody is humanized.

38. A composition comprising the antibody according to claim 33, or a CXCR4-binding fragment thereof, and a pharmaceutically acceptable excipient and/or a pharmaceutically acceptable carrier.

39. The composition according to claim 35, further comprising a second anti-HIV compound selected among the compounds capable of specifically inhibiting HIV entry and/or replication.

40. The composition according to any one of claims 36 and 38, further comprising a second anti-HIV compound selected among the compounds capable of specifically inhibiting HIV entry and/or replication.

41. The composition according to claim 40, wherein said second anti-HIV compound is chosen from HIV protease inhibitors (PI), nucleoside /nucleotide HIV reverse-transcriptase inhibitors (NRTI/NtRTI), non-nucleoside HIV reverse-transcriptase inhibitors (NNRTI), HIV entry inhibitors, and HIV inteqrase inhibitors.

42. The composition according to claim 40, wherein said second anti-HIV compound is an anti-CCR5 compound.

43. The composition according to claim 42, wherein said anti-CCR5 compound is Maraviroc.

44. The antibody of any one claims 32 and 33, or a CXCR4-binding fragment thereof, wherein the fragment is chosen from Fv, scFv, Fab, F(ab')$_2$, Fab', and scFv-Fc fragments.

45. The antibody of any one of claims 1 and 2, or a CXCR4-binding fragment thereof, wherein the fragment is chosen from Fv, scFv, Fab, F(ab')$_2$, Fab', and scFv-Fc fragments.

* * * * *